US012765955B2

(12) United States Patent
Cavalier et al.

(10) Patent No.: US 12,765,955 B2
(45) Date of Patent: Oct. 20, 2026

(54) ACTUATED GRIPS FOR CONTROLLER

(71) Applicant: Intuitive Surgical Operations, Inc., Sunnyvale, CA (US)

(72) Inventors: Matthew Cavalier, San Jose, CA (US); Brian Luptak, Santa Clara, CA (US); Gregory W. Dachs, II, San Mateo, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 100 days.

(21) Appl. No.: 18/999,617

(22) Filed: Dec. 23, 2024

(65) Prior Publication Data

US 2025/0120776 A1 Apr. 17, 2025

Related U.S. Application Data

(63) Continuation of application No. 18/189,651, filed on Mar. 24, 2023, now Pat. No. 12,213,755, which is a continuation of application No. 16/470,114, filed as application No. PCT/US2017/066465 on Dec. 14, 2017, now Pat. No. 11,633,246.

(60) Provisional application No. 62/434,904, filed on Dec. 15, 2016.

(51) Int. Cl.

| | |
|---|---|
| ***A61B 34/35*** | (2016.01) |
| ***A61B 34/00*** | (2016.01) |
| ***A61B 34/20*** | (2016.01) |
| ***A61B 34/32*** | (2016.01) |

(52) U.S. Cl.

CPC .............. *A61B 34/35* (2016.02); *A61B 34/32* (2016.02); *A61B 34/76* (2016.02); *A61B 2034/2059* (2016.02); *A61B 34/74* (2016.02)

(58) Field of Classification Search

CPC ......... A61B 34/32; A61B 34/35; A61B 34/74; A61B 34/75; A61B 34/76; A61B 17/29; A61B 90/60; A61B 90/06

See application file for complete search history.

(56) References Cited

U.S. PATENT DOCUMENTS

| | | | |
|---|---|---|---|
| 4,332,177 | A | 6/1982 | Andresen |
| 6,587,750 | B2 | 7/2003 | Gerbi et al. |
| 6,594,552 | B1 | 7/2003 | Nowlin et al. |
| 8,016,818 | B2 | 9/2011 | Ellis et al. |
| 8,418,073 | B2 | 4/2013 | Mohr et al. |

(Continued)

FOREIGN PATENT DOCUMENTS

WO WO-2013018933 A1 2/2013

OTHER PUBLICATIONS

Extended European Search Report for Application No. 17881116.2 mailed on Jul. 6, 2020. 07 pages.

(Continued)

*Primary Examiner* — Tuan V Nguyen

(74) *Attorney, Agent, or Firm* — IP Spring

(57) ABSTRACT

Implementations relate to actuated grips for a controller. In some implementations, a controller includes a central member, a grip member coupled to the central member and moveable in a grip degree of freedom, a shaft coupled to the grip member, and an actuator coupled to the shaft and operative to output an actuator force on the shaft. The actuator force causes a grip force to be applied via the shaft to the grip member in the grip degree of freedom.

20 Claims, 21 Drawing Sheets

(56) References Cited

U.S. PATENT DOCUMENTS

| | | | | |
|---|---|---|---|---|
| 8,918,207 | B2 * | 12/2014 | Prisco | B25J 9/1689 434/262 |
| 9,314,307 | B2 | 4/2016 | Richmond et al. | |
| 9,333,039 | B2 | 5/2016 | Kuchenbecker et al. | |
| 11,633,246 | B2 | 4/2023 | Cavalier et al. | |
| 12,070,291 | B2 | 8/2024 | Lutzow et al. | |
| 2008/0001559 | A1 | 1/2008 | Schena | |
| 2009/0030428 | A1 | 1/2009 | Omori et al. | |
| 2011/0087238 | A1 * | 4/2011 | Wang | B25J 9/1689 606/130 |
| 2012/0041595 | A1 | 2/2012 | Greeley et al. | |
| 2012/0051753 | A1 | 3/2012 | Labonville et al. | |
| 2012/0179169 | A1 | 7/2012 | Swarup et al. | |
| 2014/0148820 | A1 | 5/2014 | Ogawa et al. | |
| 2023/0240775 | A1 | 8/2023 | Cavalier et al. | |

OTHER PUBLICATIONS

International Search Report and Written Opinion for Application No. PCT/US2017/066465, mailed on Jun. 25, 2018, 14 pages (ISRG08070/PCT).

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

FIG. 8
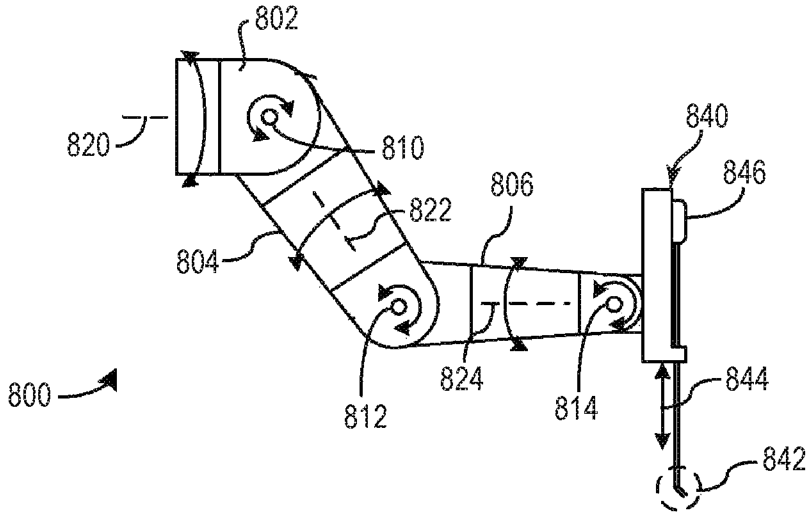
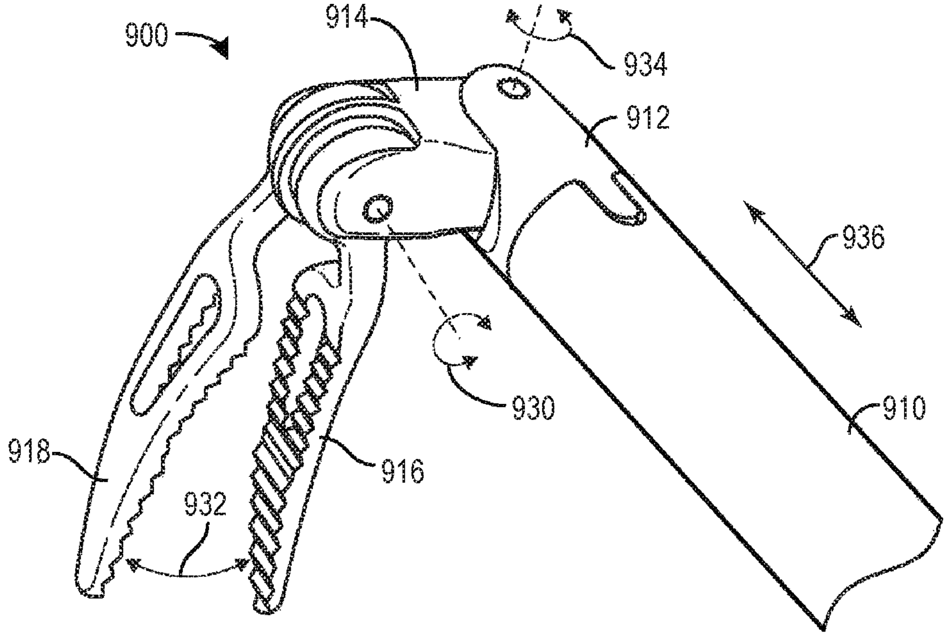
FIG. 9

ACTUATED GRIPS FOR CONTROLLER

CROSS-REFERENCE TO RELATED APPLICATIONS

This application is a continuation of U.S. patent application Ser. No. 18/189,651, filed on Mar. 24, 2023, which is a continuation of and claims the priority under 35 U.S.C. § 120 to U.S. patent application Ser. No. 16/470,114, filed on Jun. 14, 2019 (now U.S. Pat. No. 11,633,246), which is a U.S. National Stage Filing under 35 U.S.C. § 371 from International Application No. PCT/US2017/066465, filed on Dec. 14, 2017, and published as WO 2018/112227 on Jun. 21, 2018, which claims priority to U.S. Provisional Patent Application No. 62/434,904, filed Dec. 15, 2016, the entire contents of all of which are hereby incorporated by reference in their entirety.

BACKGROUND

Controller mechanisms allow a user to control various types of mechanisms and instruments. Teleoperated surgical devices, for example, can use various types of medical instruments to perform minimally invasive surgical procedures that reduce damage to healthy tissue of patients. The medical instruments can be connected to slave devices such as slave arms that can be manipulated to perform the surgical procedures. Control of the medical instruments at a slave device can be provided to an operator at one or more master controllers, e.g., at a remote operator terminal or station. Actuators of the slave device can be controlled by the master controller to cause motion of a medical instrument, camera, or other end effector at the slave device that interacts with the patient surgical site. In some examples, the master controller at the operator station can be physically manipulated by the operator in one or more degrees of freedom to control the end effector to be moved in coordination with the manipulation of the controller, e.g., to move in corresponding degrees of freedom at the operating site.

For example, in some teleoperated systems, controllers can include one or more grips that are pressed or rotated by the operator to control a similar motion on an end effector. For example, pincher grips on a master controller can provide a pinching motion that can control a similar pinching motion of forceps, tweezers, scissors, or other end effector instruments on a controlled slave device that can be used in surgery or other types of tasks. However, controlling the wide variety of different types of instruments that can be used in various surgical operations and other tasks with a controller having a fixed mechanical response to user manipulation can limit the effectiveness of utilizing such a variety of instruments in performed tasks.

SUMMARY

Implementations of the present application relate to actuated grips of a controller. In some implementations, a controller includes a central member, a grip member coupled to the central member and moveable in a grip degree of freedom, a shaft coupled to the grip member, and an actuator coupled to the shaft and operative to output an actuator force on the shaft. The actuator force causes a grip force to be applied via the shaft to the grip member in the grip degree of freedom.

Various implementations and examples of the controller are described. For example, in some implementations, the grip degree of freedom is a rotary degree of freedom, and the shaft is coupled to the grip member via at least one rotary coupling such that the grip member is rotatable relative to the shaft. In some examples, the shaft extends through at least a portion of the central member. In some implementations, the actuator is a linear actuator and the actuator force is an active force output to the shaft along a longitudinal axis of the shaft, where the shaft is decoupled in rotation from the actuator about the longitudinal axis of the shaft. In some implementations, a transmission is coupled between the actuator and the shaft, where the actuator is a rotary actuator and the actuator force is a rotational force, the transmission includes a mechanism configured to convert the rotational force to a linear force applied along a longitudinal axis of the shaft, and the shaft is decoupled in rotation from the actuator. For example, in various implementations, the transmission includes a ballscrew mechanism; a crank and a linkage, where the crank is coupled to the actuator and the linkage is coupled between the crank and the shaft; or a capstan drum coupled to the actuator and a carriage coupled to the shaft, where the capstan drum is coupled to the carriage by a cable. Some implementations include a cam between the grip member and the shaft, where the shaft and the cam are rotated by the actuator to cause the grip forces to be applied to the grip member based on an angular position of a portion of a surface of the cam.

In some examples, the grip member is a first grip member, the grip degree of freedom is a first grip degree of freedom, the controller includes a second grip member coupled to the central member and to the shaft, and the second grip member is moveable in a second grip degree of freedom. In some implementations, the actuator forces cause a first grip force to be applied via the shaft to the first grip member in the first grip degree of freedom and cause a second grip force to be applied via the shaft to the second grip member in the second grip degree of freedom. In some implementations, the first and second grip members are coupled to the shaft by one or more link members, where the one or more link members are configured to cause the first and second grip members to simultaneously move in the first and second grip degrees of freedom, respectively, in directions toward each other or away from each other. In some examples, the link members include a first link member having a first rotary coupling between a first end of the first link member and the shaft and having a second rotary coupling between a second end of the first link member and the first grip member, and a second link member having a first rotary coupling between a first end of the second link member and the shaft and having a second rotary coupling between a second end of the second link member and the second grip member. In some implementations, the first link member and the second link member each rotate in a respective plane of two parallel planes, where the first end of the first link member is coupled to the shaft at a first location of the shaft that is spaced farther from the first grip member than a second location of the shaft, and the first end of the second link member is coupled to the shaft at the second location of the shaft that is spaced farther from the second grip member than the first location of the shaft.

In further examples, the controller includes a second grip member coupled to the central member, where the second grip member is moveable in a second grip degree of freedom. In some implementations, a second shaft is coupled to the second grip member, and a second actuator is coupled to the second shaft, operative to output a second actuator force to the second shaft, where the second actuator force causes a second grip force to be applied via the second shaft to the second grip member in the second grip degree of freedom.

In some implementations, the controller further includes a spring coupled between one end of the shaft and the central member, where the spring is configured to compress in response to the grip member moving in a first direction in the grip degree of freedom and decompress in response to the grip member moving in a second direction in the grip degree of freedom. In some implementations, the grip member includes an additional grip degree of freedom that includes rotation of the grip member and the shaft about a longitudinal axis of the shaft, and where the controller further includes a second actuator operative to output a second actuator force to cause the rotation of the grip member and the shaft in the additional grip degree of freedom about the longitudinal axis of the shaft, where the rotation in the additional grip degree of freedom is decoupled in rotation from the first actuator. In some examples, the second actuator outputs the second actuator force on a belt that drives a pulley coupled to the shaft.

In some implementations, a method includes sensing, with one or more sensors, one or more positions of one or more grips of a controller in one or more respective degrees of freedom of the one or more grips, where the one or more positions are used to control movement of an end effector of a slave device in communication with the controller. The method applies force to the one or more grips using one or more actuators coupled to the controller, where the force is applied in the respective degrees of freedom of the one or more grips, and the force is applied according to at least one force profile associated with a type of the end effector controlled by the grips.

Various implementations and examples of the method are described. In some examples, at least one of the respective degrees of freedom of the one or more grips is a rotary degree of freedom, and applying force to the one or more grips includes controlling the one or more actuators that are coupled to a shaft coupled to the one or more grips, where the one or more actuators are controlled to output an actuator force that causes a linear force to be applied to the shaft along a longitudinal axis of the shaft. For example, in some implementations, the one or more grips are two grips provided in a pincher configuration, where the two grips move simultaneously toward each other or away from each other.

In some implementations, the force profile includes a plurality of different force output functions at different position ranges of the one or more grips. For example, the force profile is selected from a plurality of force profiles associated with a plurality of types of end effectors usable with the slave device. In some examples, the force profile includes a first linear force output function and a second linear force output function that has a different slope than the first linear force output function. In some examples, the one or more grips are two grips, and the force profile includes a force output function that controls the force applied to at least one grip of the two grips to bias the at least one grip to a limited range of positions in the one or more respective degrees of freedom, where the limited range of positions is smaller than a full range of positions of the at least one grip. In some examples, the force profile includes a force output function that controls the force applied to two grips to bias the two grips to a closed position of the two grips.

In some examples, the method further includes activating a controlling mode that enables controlling one or more actuators of the slave device to physically move at least a portion of the slave device in correspondence with physical manipulation of the one or more grips by a user in the one or more respective degrees of freedom. In some implementations, the method further includes moving the one or more grips to respective positions in the one or more respective degrees of freedom to match a position of one or more controlled components of an end effector of the slave device.

BRIEF DESCRIPTION OF THE DRAWINGS

FIG. 8 is a diagrammatic illustration of an example arm assembly or portion thereof, which can be used for one or more of the arm assemblies of the manipulator slave device of FIG. 1, according to some implementations;

FIG. 9 is a perspective view of one example of an end effector which can be used with the manipulator slave device of FIG. 1, according to some implementations;

DETAILED DESCRIPTION

Figure 1:
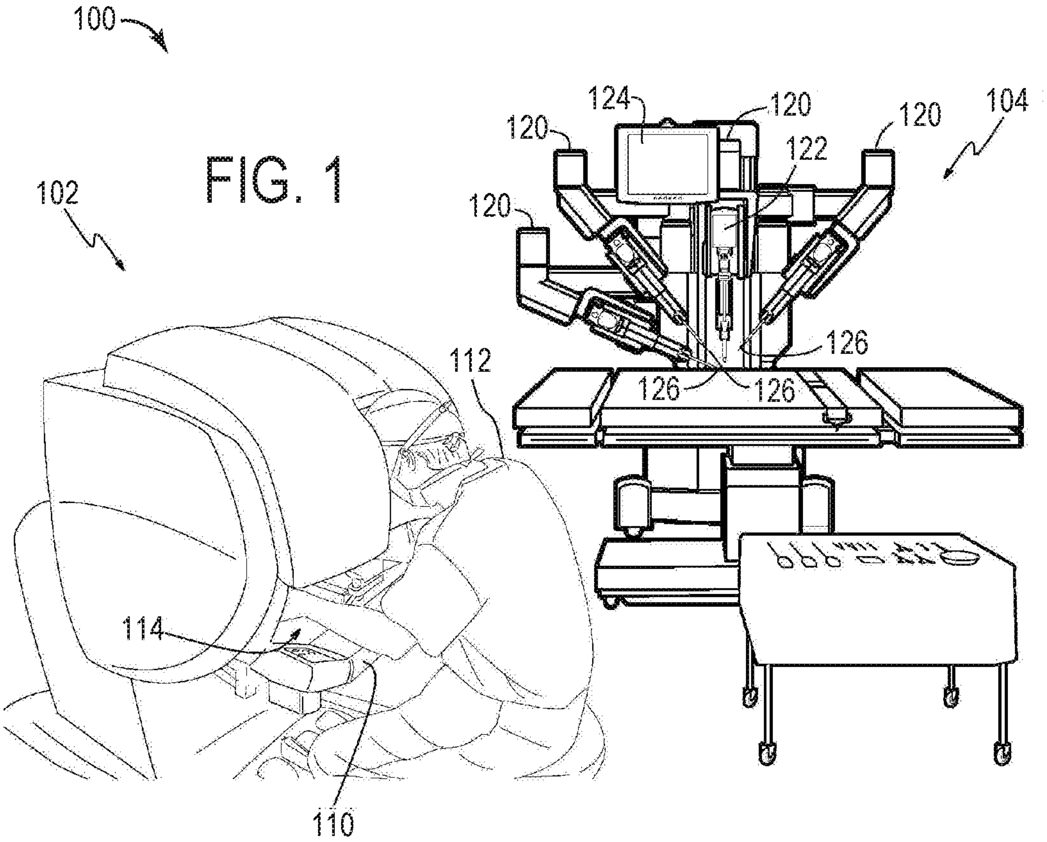
FIG. 1 is a diagrammatic illustration of an example implementation of a teleoperated surgical system which can be used with one or more features disclosed herein, according to some implementations.

One or more implementations described herein relate to actuated grips of a controller. In some implementations, a controller includes one or more grip members, each moveable in a respective degree of freedom, a shaft coupled to the one or more grip members, and an actuator coupled to the shaft and operative to output actuator forces on the shaft. The actuator forces cause grip forces to be applied via the shaft to the grip members in the respective degrees of freedom. For example, the degree of freedom of each grip member can be a rotary degree of freedom, and the shaft is coupled to the grip member via at least one rotary coupling such that the grip member is rotatable relative to the shaft. The actuator forces can be output to the shaft along a longitudinal axis of the shaft, and the shaft is decoupled in rotation from the actuator about the longitudinal axis of the shaft.

Various other features are also disclosed. For example, the actuator can be a linear actuator outputting active linear forces, or can be a rotary actuator outputting rotary forces. Rotary forces from a rotary actuator can be converted to linear forces through the use of a transmission, e.g., a ballscrew mechanism or a crank and linkage. Some implementations can include two grip members that rotate in respective degrees of freedom, e.g., toward each other or away from each other in a pincher-type of movement. In some examples, link members can couple the grip members to the shaft, and in some implementations the link members can be attached to the shaft at rotational couplings located a further distance from their respective linked grip member than the rotational coupling of the other link member. Some implementations can provide multiple grip members, where a grip member receives forces from an associated actuator independently of the other grip members. A spring can be coupled between the shaft and a controller body, which can provide resistive force to a closing motion of the grip members. In some examples, the grip members and the shaft can together be rotated about the lengthwise axis of the shaft, and forces can be applied in this degree of freedom by a second actuator, where the shaft is decoupled in rotation from the second actuator.

Described features also include sensing positions of one or more grips of a controller in one or more respective degrees of freedom, where the positions are used to control movement of an end effector of a slave device in communication with the controller, and applying force to the one or more grips in the grip degrees of freedom using one or more actuators. The force can be applied according to at least one force profile associated with a type of the end effector controlled by the grips. For example, a force profile can be selected from multiple force profiles associated with different types of end effectors usable with the slave device. The force profiles can define different grip forces for different grip positions, such as different linearly-changing forces at different grip positions. Some implementations can use the grip forces to constrain or hold one or more of the grips in a particular position, such as a closed position of the grip members, and/or to match the positions of the grips to current positions of components of the controlled end effector.

Features described herein provide forces on one or more grips of a controller and provide several advantages. For example, decoupling the rotation of a transmission shaft from an actuator providing linear forces on the shaft allows the grips to be rotated about an axis of rotation of the shaft without having to rotate the actuator. A spring can assist actuator forces on the grips, e.g., by resisting motion of the grip members in particular directions, allowing the active actuator to be sized smaller. The grip forces can provide different assistive forces on the controller grips for different types of end effectors of a controlled slave device, such as different types of surgical instruments. This can provide more effective control over these different types of instruments. For example, forces can guide the user with respect to particular grip positions that correspond to particular instrument positions for particular types of end effector instruments (e.g., a grip position to close a held clip in a clip applier, a closed or static grip position for an instrument not using grip motion, etc.). Positions of the grips can be matched to a current position of an instrument component of a controlled slave device, providing the user with an intuitive sense of control over the instrument immediately after contacting the grips. Forces can be output on the grips as informational assistance to the user, e.g., to indicate particular interactions of a controlled slave device and/or events occurring in during the control procedure. For example, vibrations can be output directly on grips contacted by a user's fingers using described features, rather than or in addition to outputting a vibration in other, less directly-experienced degrees of freedom of the controller or vibrating the entire master controller system.

Features thus allow a user to operate a controller more easily, accurately, and intuitively, thus providing more accurate results in procedures performed using the controller. For example, medical procedures performed using the controller and slave devices can be accurately performed with less user training required.

The terms "center," "parallel," "perpendicular," "aligned," or particular measurements in degrees, Hertz, or other units as used herein need not be exact and can include typical engineering tolerances.

FIG. 1 is a diagrammatic illustration of an example teleoperated surgical system 100 which can be used with one or more features disclosed herein. Teleoperated surgical system 100 includes a master control workstation (e.g., surgeon's console) 102 and a manipulator slave device 104.

In this example, the master control workstation (e.g., surgeon's console) 102 includes a viewer 213 (shown in FIG. 2) where an image of a worksite is displayed during an operating procedure using the system 100. For example, the image can be displayed by a display device such as one or more display screens, depict a surgical site during a surgical procedure. A support 110 is provided on which a user 112, e.g., an operator such as a surgeon, can rest his or her forearms while gripping two master controllers 210 and 212 (shown in FIG. 2), one in each hand. The master controllers are positioned in a workspace 114 disposed inwardly beyond the support 110. When using the workstation 102, the user 112 can sit in a chair in front of the workstation, position his or her eyes in front of the viewer and grip the master controllers, one in each hand, while resting his or her forearms on the support 110. Additional details are described below with reference to FIG. 2.

A manipulator slave device 104 is also included in the teleoperated system 100. During a surgical procedure, the slave device 104 can be positioned close to a patient (or simulated patient) for surgery, where it can remain stationary until a particular surgical procedure or stage of a procedure is completed. Manipulator slave device 104 can include one or more arm assemblies 120. In some examples, one or more of the arm assemblies 120 can be configured to hold an image capturing device, e.g., an endoscope 122, which can provide captured images of a portion of the surgical site. In some implementations, the captured images can be transmitted to the viewer of the workstation 102 and/or transmitted to one or more other displays, e.g., a display 124 coupled to the slave device 120. In some examples, each of the other arm assemblies 120 may include a surgical tool 126. Each surgical tool can include a surgical end effector, e.g., for treating tissue of the patient.

In this example, the arm assemblies 120 can be caused to move and articulate the surgical tools 126 in response to manipulation of the master controllers 210 and 212 at the workstation 102 by the user 112, e.g., so that the user 112 can direct surgical procedures at internal surgical sites through minimally invasive surgical apertures. For example, one or more actuators coupled to the arm assemblies 120 can output force to cause links or other portions of the arm assemblies to move in particular degrees of freedom in response to control signals received from the workstation 102. The workstation 102 can be used within a room (e.g., an operating room) with the slave device 104 or can be positioned more remotely from the slave device 102, e.g., at a different location than the slave device.

Some implementations of the teleoperated system 100 can provide different modes of operation. In some examples, in a non-controlling mode (e.g., safe mode) of the teleoperated system 100, the controlled motion of the manipulator slave device 104 is disconnected from the master controllers of the workstation 102 in disconnected configuration, such that movement and other manipulation of the master controls does not cause motion of the manipulator slave device 104. In a controlling mode of the teleoperated system (e.g., following mode), motion of the manipulator slave device 104 can be controlled by the master controls 210 and 212 of the workstation 102 such that movement and other manipulation of the master controllers causes motion of the manipulator slave device 104, e.g., during a surgical procedure.

Some implementations can be or include a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, California. However, features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Other, non-teleoperated systems can also use one or more described features, e.g., various types of control systems and devices, peripherals, etc.

In some implementations, a controlled slave manipulator device can be a virtual representation of device, e.g., presented in a graphical simulation provided by a computing device coupled to the teleoperated system 100. For example, a user can manipulate the master controls 210 and 212 of the workstation 102 to control a displayed representation of an end effector in virtual space of the simulation, similarly as if the end effector were a physical object coupled to a physical slave device.

Figure 2:
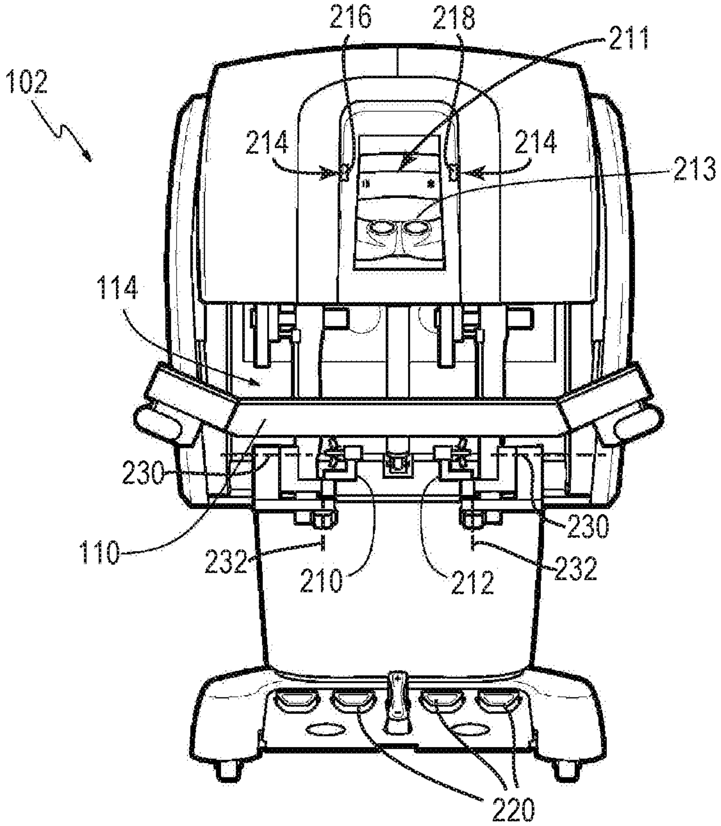
FIG. 2 is a front elevational view of an example master control workstation as shown in FIG. 1, according to some implementations.

FIG. 2 is a front elevational view of an example master control workstation 102 as described above for FIG. 1. Master control workstation 102 includes a viewer 213, where an image of a worksite can be displayed during a procedure using the teleoperated system 100. For example, images depicting a surgical site can be displayed during a surgical procedure. The viewer 213 can be positioned within a viewing recess 211 in which the user can position his or her head to view images displayed by the viewer 213. When using the workstation 102, the user 112 can sit in a chair in front of the workstation and position his or her head within the recess 211 such that his or her eyes are positioned in front of the viewer 213.

In some implementations, one or more user presence sensors 214 can be positioned at one or more locations of the master control workstation 102 to detect the presence of a user located next to or near to the workstation 102. In this example, the user presence sensors 214 can sense a presence of a user's head within the recess 211. For example, an optical sensor can be used for a presence sensor, where the optical sensor includes an emitter 216 and a detector 218. A beam of infrared or other wavelength of light is emitted from one side of the recess 211 by the emitter 216, and the beam is detected on the other side of the recess by the detector 218. If the beam is interrupted from detection by the detector, the system determines that a user's head is within the recess and that the user is in a proper position to use the master controllers of the master control workstation 102. Additional or alternative types of presence sensors can be used in various implementations.

Two master controllers 210 and 212 are provided for user manipulation. In some implementations, each master controller 210 and 212 can be configured to control motion and functions an associated arm assembly 120 of the manipulator slave device 104. For example, a master controller 210 or 212 can be moved in a plurality of degrees of freedom to move a corresponding end effector of the slave device 104 in corresponding degrees of freedom. The master controllers 210 and 212 are positioned in workspace 114 disposed inwardly beyond the support 110. For example, a user 112 can rest his or her forearms while gripping the two master controllers 210, 212, with one controller in each hand. The user also positions his or her head within the viewing recess 211 to view the viewer 213 as described above while manipulating the master controllers 210 and 212. Various examples of master controller portions are described below.

Some implementations of workstation 102 can include one or more foot controls 220 positioned below the master controls 210 and 212. The foot controls 220 can be depressed, slid, and/or otherwise manipulated by a user's feet to input various commands to the teleoperated system while the user is sitting at the master control workstation 102.

Figure 3:
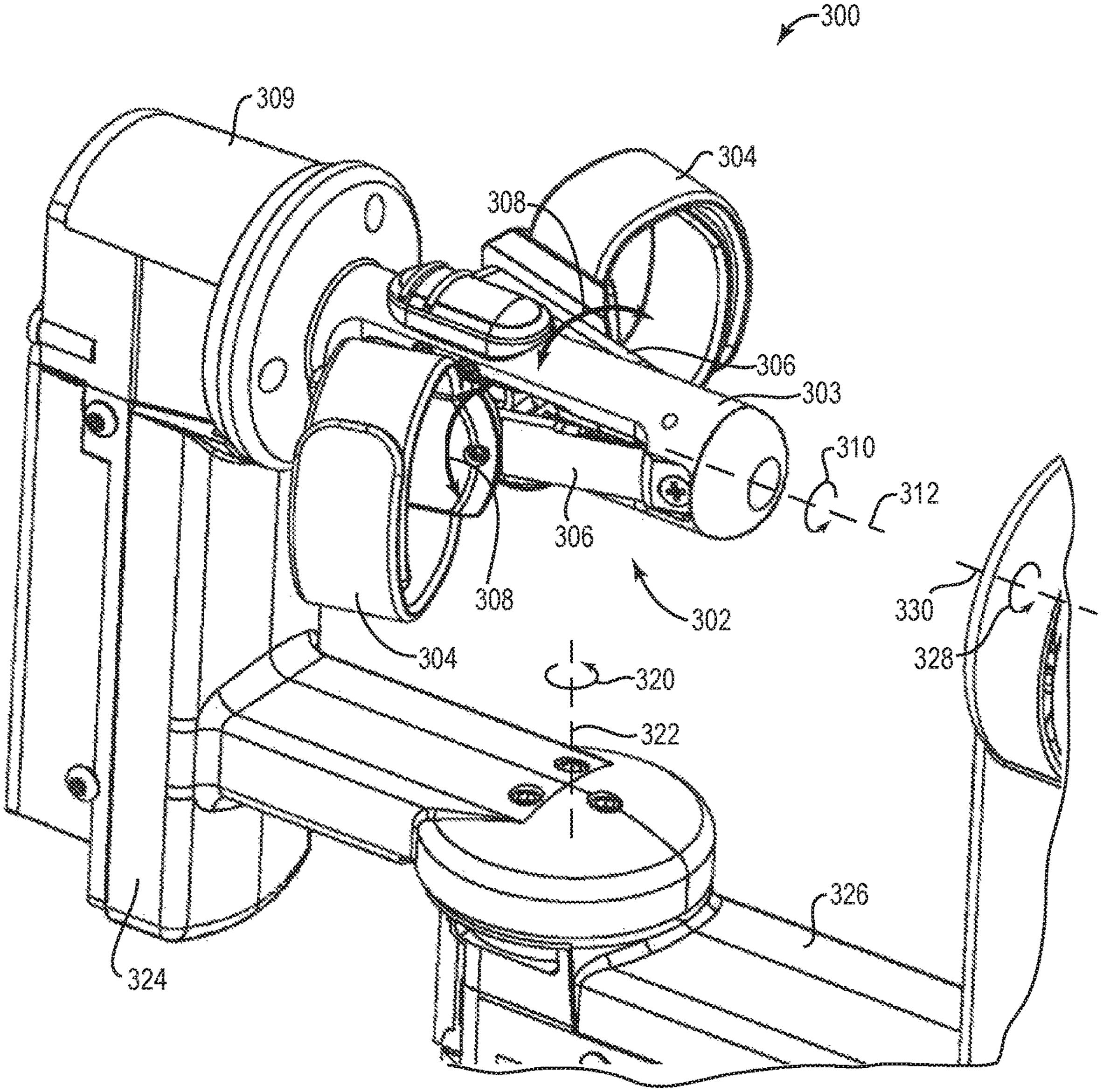
FIG. 3 is a perspective view of an example portion of a master controller which can include one or more features described herein, according to some implementations.

FIG. 3 is a perspective view of an example portion 300 of a master controller which can include one or more features described herein. In some implementations, master controller portion 300 can be used as a portion of a master controller 210 or 212 as described above with reference to FIGS. 1 and 2. In some implementations, the master controller portion 300 includes one or more gimbal mechanisms.

Master controller portion 300 includes a handle 302 which is contacted by a user to manipulate the master controller 300. In this example, the handle 302 includes two grips that each include a finger loop 304 and a grip member 306. The two grip members 306 are positioned on opposite sides of a central portion 303 of the handle 302, where the grip members 306 can be grasped, held, or otherwise contacted by a user's fingers. The two finger loops 304 are attached to grip members 306 and can be used to secure a user's fingers to the associated grip members 306. The user may also contact other portions of handle 302 while grasping the grip members 306. The grip members 306 are pivotally attached to the central portion 303 of the handle 302. Each grip member 306 and finger loop 304 can be moved in an associated degree of freedom 308 by a user. For example, the grip members 306 can be moved simultaneously in a pincher-type of movement (e.g., toward or away from each other). In various implementations, a single grip member 306 and finger loop 304 can be provided, or only one of the grip members 306 can be moved in the degree of freedom 308 while the other grip member 306 can be fixed with reference to the handle 302.

One or more sensors (not shown) coupled to the handle 302 can detect the positions of the grip members 306 in their degrees of freedom 308 and send signals describing the positions to one or more control circuits of the teleoperated system 100. The control circuits can provide control signals to the slave manipulator device 104, an example of which is described with reference to FIG. 23. For example, the positions of the grip members 306 in degrees of freedom 308 can be used to control any of various degrees of freedom of an end effector of the slave manipulator device 104, some examples of which are described below. Some implementations of the controller 300 can provide one or more passive actuators (e.g., springs) between the grip members 306 and the central portion 303 of the handle 302 to provide resistance in particular directions of the grips (e.g., movement in directions toward each other in degree of freedom 308). Various implementations can provide one or more active actuators (e.g., motors, voice coils, etc.) to output active forces on the grip members 306 in the degree of freedom 308. For example, a sensor and/or actuator can be housed in central portion 303 or in housing 309 and coupled to the grip members 306 by a transmission.

The handle 302 of example master controller portion 300 can additionally be provided with a rotational degree of freedom 310 about an axis 312 extending approximately along the center of the central portion 303 of handle 302. A user can rotate the grip members 306 as a single unit around the axis 312 to provide control of, e.g., an end effector of the manipulator slave device 104 or other element of the slave device.

One or more sensors (not shown) can be coupled to the handle 302 to detect the rotation and/or position of the handle 302 in the rotational degree of freedom 310. For example, the sensor can send signals describing the position to one or more control circuits of the teleoperated system 100 which can provide control signals to the slave device 104 similarly as described above. For example, degree of freedom 310 can control a particular degree of freedom of an end effector of the slave device that is different than a slave degree of freedom controlled by degree of freedom 308 of the grip members 306.

Some implementations of the controller 300 can provide one or more actuators to output forces on the handle 302 (including grip members 306 and finger loops 304) in the rotational degree of freedom 310. For example, a sensor and/or actuator can be housed in housing 309 and coupled to the handle 302 by a shaft extending through the central portion 303 of the handle 302.

In various implementations, the handle 302 can be provided with additional degrees of freedom. For example, a rotational degree of freedom 320 about an axis 322 can be provided to the handle 302 at a rotational coupling between an elbow shaped link 324 and a link 326, where the elbow shaped link 324 is coupled to the handle 302 (e.g., at housing 309). For example, axis 322 can be similar to axis 232 shown in FIG. 2. Additional degrees of freedom can similarly be provided. For example, link 326 can be elbow-shaped and a rotational coupling can be provided between the other end of link 326 and another link (not shown). A rotational degree of freedom 328 about an axis 330 can be provided to the handle 302 at the rotational coupling. For example, axis 330 can be similar to axis 230 shown in FIG. 2. In some examples, the master controller 300 can allow movement of the handle 302 within the workspace 114 of the master control workstation 102 with a plurality of degrees of freedom, e.g., six degrees of freedom including three rotational degrees of freedom and three translational degrees of freedom. This allows the handle 302 to be moved to any position and any orientation within its range of motion. One or more additional degrees of freedom can be sensed and/or actuated similarly as described above for the degrees of freedom 308 and 310. In some implementations, each additional degree of freedom of the handle 302 can control a different slave degree of freedom (or other motion) of an end effector of the slave device 104.

One or more features described herein can be used with other types of master controllers. For example, ungrounded master controllers can be used, which are free to move in space and disconnected from ground. In some examples, one or more handles similar to handle 302 and/or grip members 306 can be coupled to a mechanism worn on a user's hand and which is ungrounded, allowing the user to move grips freely in space. In some examples, the positions of the grips relative to each other and/or to other portions of the handle can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Some examples of ungrounded master controllers are described in U.S. Pat. Nos. 8,543,240 and 8,521,331, both incorporated herein by reference. The detection of user touch described herein can be used with ungrounded master controllers. For example, vibration can be applied to a handle (e.g., grip) by one or more actuators coupled to the handle, and this vibration can be sensed similarly as described herein to determine if the handle is contacted or grasped by the user.

Figure 4:
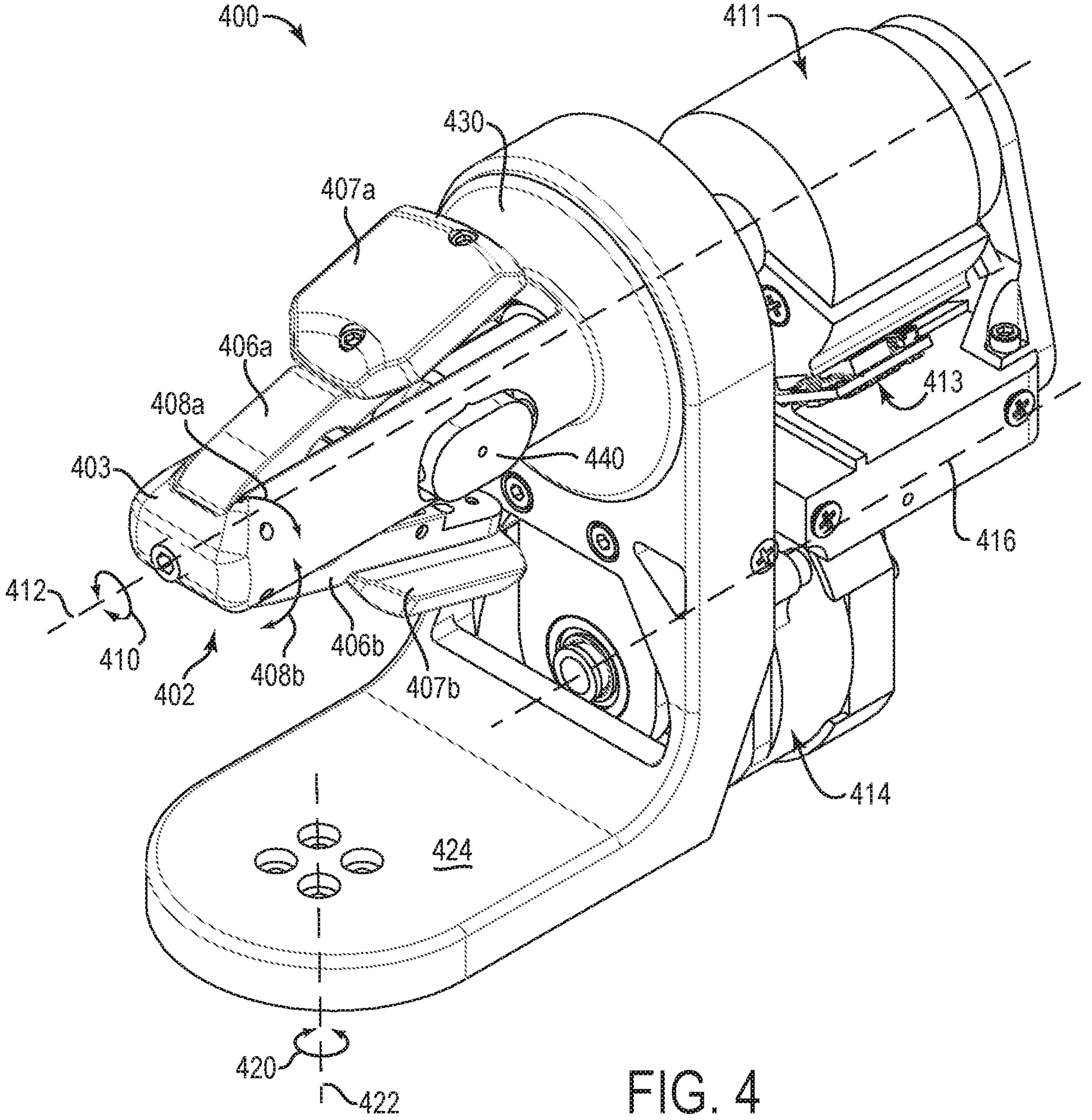
FIGS. 4, 5, and 6 are different views of an example implementation of a portion of a controller including one or more features described herein, according to some implementations.
Figure 5:
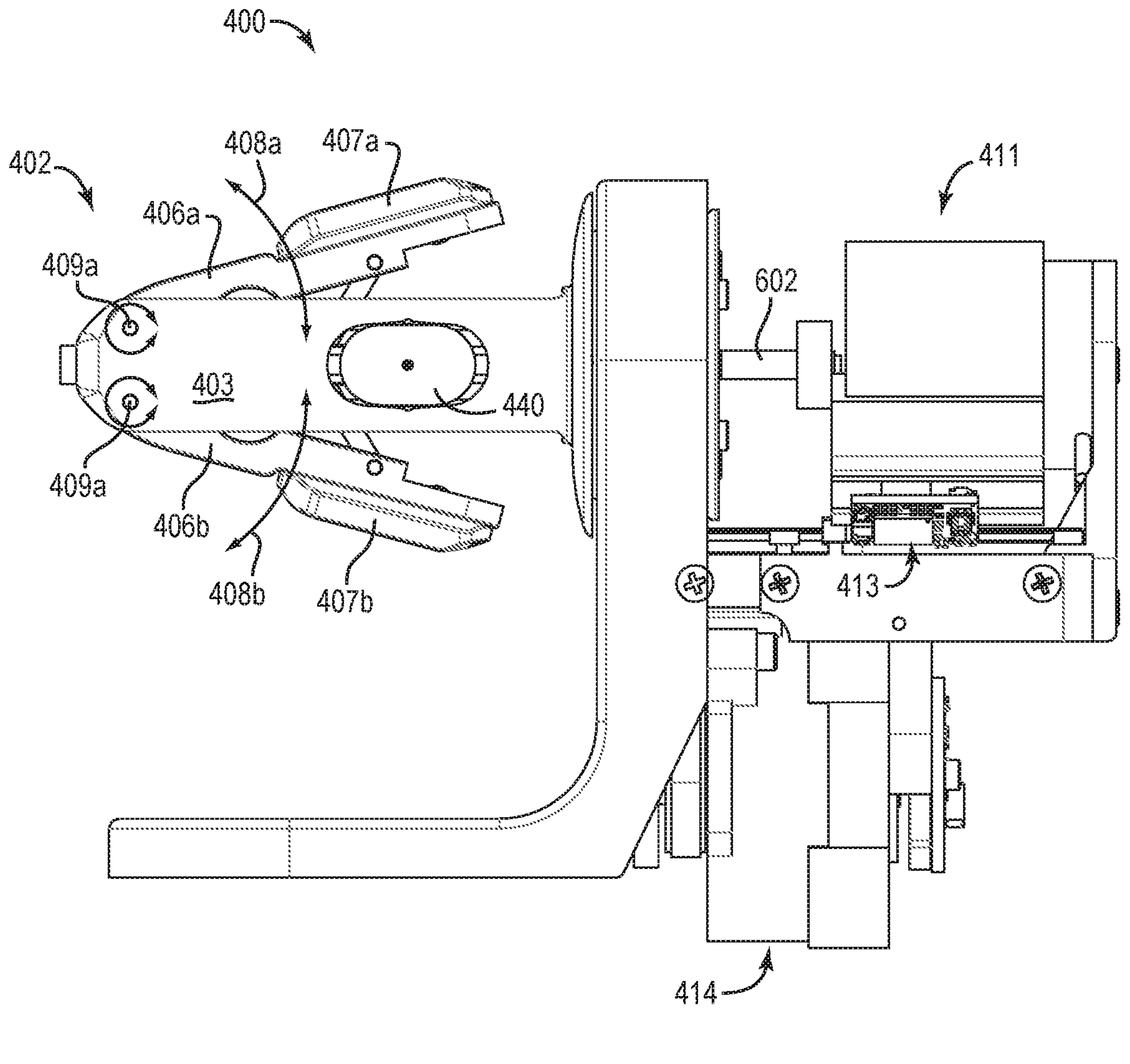

FIG. 4 is a perspective view and FIG. 5 is a side elevational view of an example implementation of a portion 400 of a controller including one or more features described herein. In some implementations, controller portion 400 can be used as a portion of a master controller 210 or 212 as described above with reference to FIGS. 1 and 2. In some implementations, the controller portion 400 includes one or more gimbal mechanisms. In this example implementation, the controller portion 400 can provide forces in the degrees of freedom of the grips of the controller.

Controller portion 400 can include several elements similar to controller portion 300 shown in FIG. 3. For example, a handle 402 can be contacted by a user to manipulate the master controller 400. In this example, the handle 402 includes two grips that each include a grip member 406*a* or 406*b*. The two grip members 406*a* and 406*b* are positioned on opposite sides of a central portion 403 of the handle 402, where the grip members 406*a* and 406*b* can be grasped, held, or otherwise contacted by a user's fingers. For example, finger contacts 407*a* and 407*b* can be connected or formed at the unconnected end of the grip members 406*a* and 406*b*, respectively, to provide surfaces to contact the user's fingers. Finger loops (not shown) similar to finger loops 304 of FIG. 3 can be attached to the grip members in some implementations, e.g., to secure a user's fingers to the associated grip members 406*a* and 406*b*.

The grip members 406*a* and 406*b* are coupled to the central portion 403 of the handle 402 at rotational couplings 409*a* and 409*b*, respectively, allowing rotational movement of the grip members with respect to the central portion. Each grip member 406*a* and 406*b* can be moved in an associated degree of freedom 408*a* and 408*b*, respectively (see FIG. 5), e.g., by a user contacting the grip members. For example, in some implementations the grip members 406*a* and 406*b* can be moved simultaneously in a pincher-type of movement (e.g., toward or away from each other). For example, the first and second grip members can move simultaneously and in coordination, e.g., move in opposing directions and by the same angular amount in their respective degrees of freedom in response to motion of the main shaft. In various implementations, a single grip member 406*a* or 406*b* can be provided, or only one of the grip members 406*a* or 406*b* can be moved in the associated degree of freedom 408*a* or 408*b* while the other grip member 406*b* or 406*a* can be fixed with reference to the handle 402. In other implementations, the grip members can be coupled to the handle with other mechanisms and can be moved in linear degrees of freedom, e.g., in linear directions toward and away from the central portion 403 of the handle 402.

One or more sensors (not shown in FIGS. 4-6) can be coupled to the handle 402 and/or other components of the controller portion 400 and can detect the positions of the grip members 406*a* and 406*b*. The sensors can send signals describing sensed positions and/or motions to one or more control circuits of the teleoperated system 100. In some modes or implementations, the control circuits can provide control signals to the slave manipulator device 104. For example, the positions of the grip members 406*a* and 406*b* in degrees of freedom 408*a* and 408*b* can be used to control any of various degrees of freedom of an end effector of the slave manipulator device 104, some examples of which are described herein.

An active actuator (e.g., motor, voice coil, etc.) 411 can be coupled to the grip members 406*a* and 406*b* and can output active forces on the grip members in the either or both of degrees of freedom 408*a* and 408*b* based on control signals received by the actuator 411. For example, the actuator 411 can be coupled to the grip members 406*a* and 406*b* by a main shaft and/or a transmission. Some examples of such couplings are described below.

A sensor 413 can be used to sense motion of the grip members 406*a* and 406*b*. Sensor 413 can sense the position of a moving portion of actuator 411 in its linear range of motion (described below), which indicates the position of the grip members 406*a* and 406*b* in their rotary degrees of freedom. The sensor 413 can be any of a variety of types of sensors, e.g., a magnetic sensor (e.g., magnetic incremental linear position sensor, Hall Effect sensor, etc.), optical sensor, encoder, resistance sensor, etc.

Some implementations of the controller 400 can provide one or more passive actuators (e.g., springs, brakes, etc.) coupled to the grip members 406*a* and 406*b* and the central portion 403 of the handle 402 to provide greater resistance in particular directions of the grips (e.g., movement in directions toward each other in degrees of freedom 408*a* and 408*b*) than in other directions (e.g., movement in directions away from each other in degrees of freedom 408*a* and 408*b*). Passive actuators can provide resistance in rotation of handle 402 about axis 412. Some examples of a passive actuator are described below.

The handle 402 of example master controller portion 400 can additionally be provided with a rotational degree of freedom 410 about an axis 412 extending approximately along the center of the central portion 403 of handle 402. A user can rotate the grip members 406*a* and 406*b* as a single unit around the axis 412 to provide control of, e.g., an end effector of the manipulator slave device 104 or other component of the slave device.

An active actuator 414 can be coupled to the handle 402 and output forces on the handle 402 (including grip members 406) in the rotational degree of freedom 410. Some examples of the transmission of force from actuator 414 to the handle 402 are described with respect to FIG. 6. One or more sensors can be coupled to the handle 402 to detect the rotation and/or position of the handle 402 in the rotational degree of freedom 410. For example, the sensor can send signals describing the position to one or more control circuits of the teleoperated system 100 which can provide control signals to the slave device 104 similarly as described above. In some examples, a sensor (e.g., a rotary encoder) can be coupled with actuator 414 to sense rotation of the actuator shaft of actuator 414 and sense rotation of the handle about axis 412.

In various implementations, the handle 402 can be provided with additional degrees of freedom. For example, a rotational degree of freedom 420 about an axis 422 can be provided to the handle 402 at a rotational coupling between an elbow shaped link 424 and another link (not shown), similarly as shown for elbow shaped link 324 and link 326 of controller portion 300 of FIG. 3. Additional degrees of freedom can similarly be provided as described above for FIG. 3. In some examples, the master controller 400 can allow movement of the handle 402 within the workspace 114 of the master control workstation 102 with a plurality of degrees of freedom, e.g., six degrees of freedom including three rotational degrees of freedom and three translational degrees of freedom. This allows the handle 402 to be moved to any position and any orientation within its range of motion. One or more additional degrees of freedom can be sensed and/or actuated similarly as described above for the degrees of freedom. In some implementations, each additional degree of freedom of the handle 402 can control a different slave degree of freedom of an end effector of the slave device 104.

In some implementations, handle 402 can also include one or more switches or buttons 440, e.g., coupled to the central portion 403 or to mechanisms within central portion 403. For example, two buttons 440 can each be positioned on opposite sides of axis 412, or additional buttons can be provided. In some examples, button 440 can slide parallel to the axis 412, e.g., as directed by a user's finger, or the button can be depressed. The button 440 can be moved to various positions to provide particular command signals, e.g., to select functions, options, or modes of the control console and/or master controller (e.g., a controlling mode or non-controlling mode as described below), to command a slave device or other system in communication with the master controller, etc. In an example implementation, button 440 can be coupled to a magnet. For example, button 440 can be coupled to a rod that extends parallel to the axis 412, where the rod can include a magnet at its end. The magnet is sensed by a magnetic sensor coupled to a plate 430, where the plate 430 is rigidly coupled to the central portion 403 of the handle 402. When the button 440 is activated by the user, e.g., slid by a user parallel to axis 412, the magnet is moved into a range sensed by the magnetic sensor. Other types of sensors can alternatively be used, such as optical sensors, mechanical switches, etc.

In some implementations, a touch-sensitive sensing surface can be provided on the handle 402 to sense a user's touch using any of a variety of types of sensors such as capacitive sensors, resistive sensors, optical sensors, etc. In some examples, one or more such sensing surfaces can be provided on the central portion 403 of the handle 402. In another example, a sensing surface can be provided on a portion of plate 430. The sensing surface can be tapped by a user's finger to provide selections or commands, and/or various gestures of the user's finger(s) over the sensing surface can be sensed to provide different selections or commands (e.g., a swipe, pinch, fingers moving away from each other, etc.).

Figure 6:
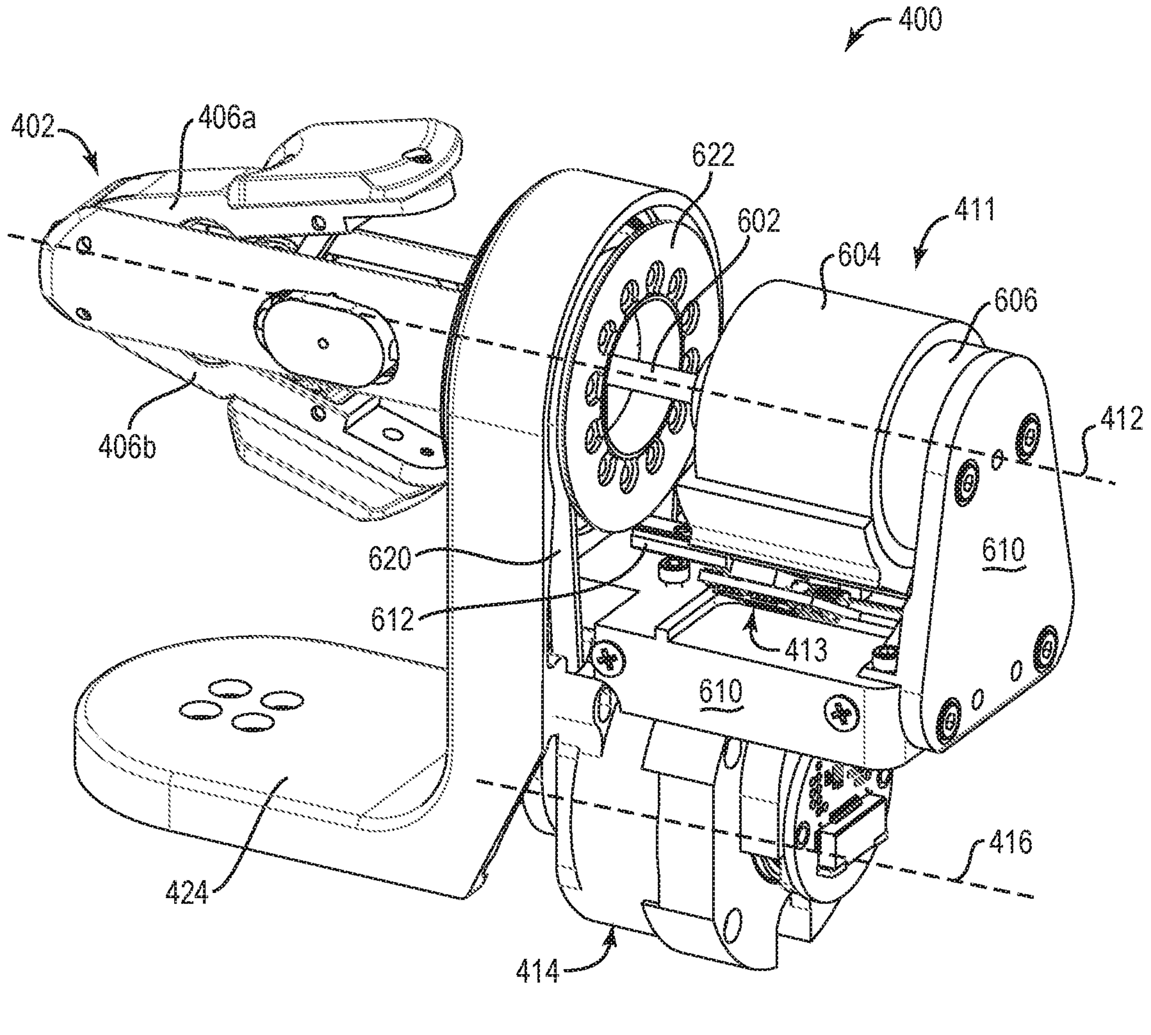

FIG. 6 is a perspective view of master controller portion 400 of FIG. 4 showing the controller portion from a different perspective. In this example, actuator 411 is shown coupled to a main shaft 602 which is linearly moved by the actuator to provide forces to the grip members 406*a* and 406*b*. The axis 412 can be the longitudinal axis of the main shaft 602, for example. In this example implementation, actuator 411 is a linear voice coil actuator outputting linear forces. A moving portion 604 of the actuator 411 is forced linearly along the axis 412 with respect to the grounded portion 606 of the actuator 411. The grounded portion 606 is coupled to the structure 610, which is rigidly coupled to the link 424. For example, in some implementations the moving portion 604 can include a coil holder having a coil. When electric current is provided in the coil, the moving portion 604 is caused to move based on the magnetic field induced with a magnet of the grounded portion 606. Alternatively, the coil can be provided in the grounded portion 606 and the magnet provided in the moving portion 604.

Moving portion 604 of the actuator 411 can move linearly along a guide rail 612 that is coupled to the grounded structure 610. A groove or slot (not shown) is provided in the moving portion 604 to engage with the guide rail 612 and align its movement with the guide rail 612. Other mechanisms can be used in other implementations to guide the moving portion 604 along axis 412. For example, a linear rail can be provided on the moving portion 604 and a groove or slot can be provided in the grounded structure 610. Sensor 413 can sense the position and/or motion of the moving portion 604 to determine the position or motion of the grip members 406*a* and 406*b*, which are coupled to the linear motion of moving portion 604 through main shaft 602.

The second actuator 414 can be a rotary actuator coupled to the structure 610. In this example, the actuator 414 is positioned such that its axis of rotation 416 is offset from the central axis 412. The actuator 414 can output rotational forces on its shaft to drive the rotation of the handle 402 about axis 412. For example, a belt 620 can grip the rotating shaft of the actuator 414 and can also grip a pulley 622 that is configured to rotate about axis 412. This configuration allows the actuator 414 to rotate the pulley 622. The pulley 622 can be rigidly coupled to a member including plate 430 (shown in FIG. 4), where the member and plate 430 are rigidly coupled to the central portion 403 of the handle 402. Thus, the pulley 622 can transmit rotational forces to the handle 402 around axis 412. In some implementation, the belt 620 can be a toothed belt that engages a toothed circumferential surface of pulley 622 to provide traction between belt and pulley.

Figure 7A:
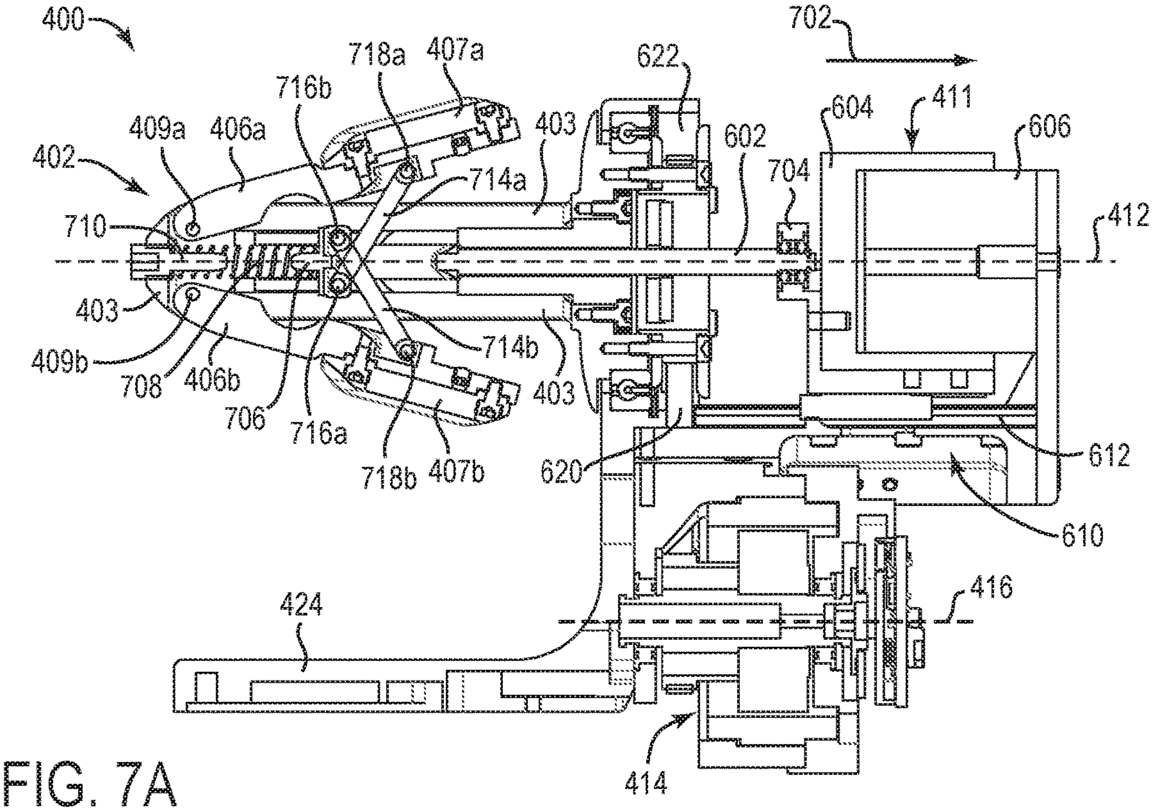
FIGS. 7A and 7B are side elevational cross-sectional views of the controller portion of FIG. 4, according to some implementations.
Figure 7B:
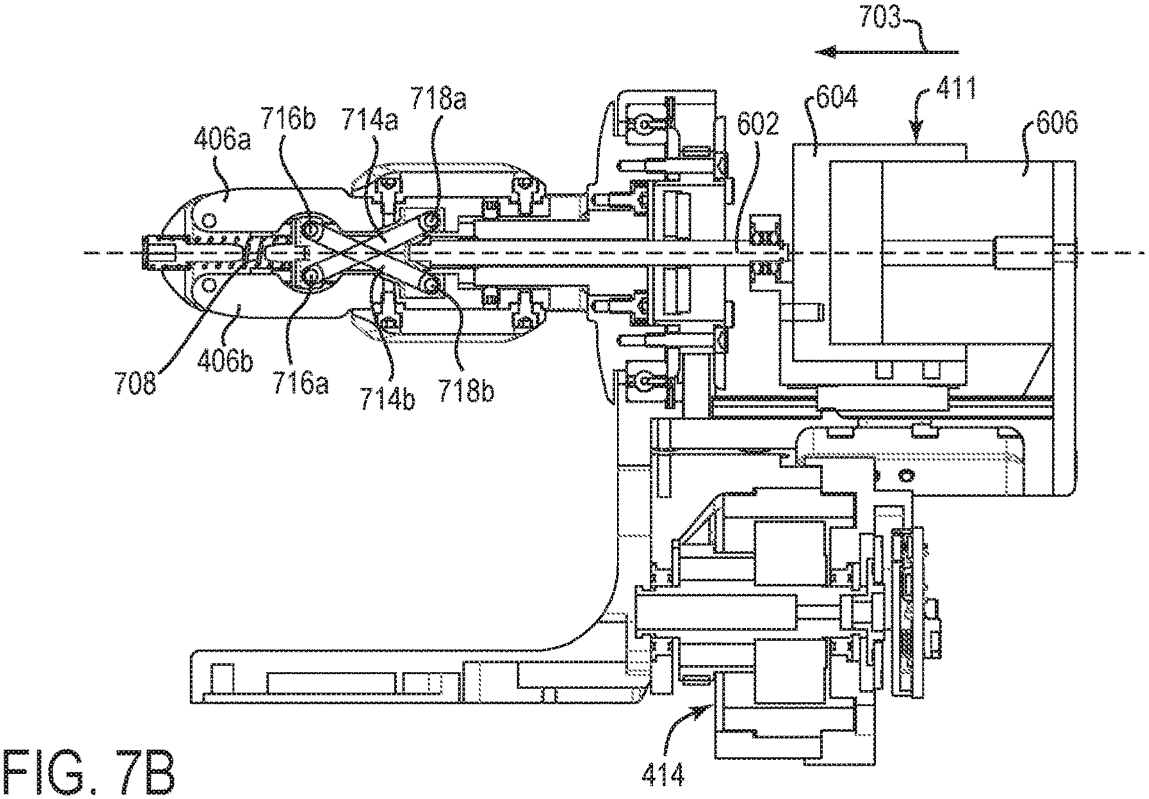

FIGS. 7A and 7B are side elevational views of the interior of controller portion 400 of FIG. 4 and showing different positions of the grip members 406*a* and 406*b*.

In FIG. 7A, the grip members 406*a* and 406*b* are in an "open" position, e.g., the grip members are at a position in which their disconnected ends are furthest away from each other as allowed by the coupled mechanism. To obtain this position from a position in which the links are closer to each other, the actuator 411 provides a force in the direction 702 away from the grip members 406*a* and 406*b*. For example, the moving portion 604 of the actuator 411 can be moved in direction 702. Moving portion 604 is coupled to the main shaft 602 at a coupling 704. Coupling 704 couples the main shaft 602 to the moving portion 604 of the actuator 411 along the linear directions of axis 412, and decouples the shaft 602 and moving portion 604 in the rotational directions around axis 412 so that the shaft 602 can rotate without rotating the moving portion 604.

The main shaft 602 is also decoupled in rotation from the pulley 622 and the central portion 403 of the handle 402 so that the shaft can rotate without rotating these elements. The tip 706 of the main shaft 602 is connected to one end of a spring 708 that extends along the axis 412, where the other end of the spring 708 is connected to a pin 710 that is connected to the central portion 403 of the handle 402. Spring 708 compresses in the direction opposite to direction 702. Depending on the rest position of the spring 708 in different implementations and the current position of the shaft 602 along axis 412, the spring 708 can bias the movement of the main shaft 602 in either direction 702 or in the opposite direction. In some implementations, pin 710 can be made adjustable by a user. For example, the pin 710 can include screw threads to move the pin 710 along the axis 412 when rotated, thus adjusting the tension in spring 708.

Two intermediate links 714*a* and 714*b* are connected at one of their ends to the main shaft 602 at rotational couplings 716*a* and 716*b*, respectively, allowing the intermediate links to rotate with respect to the main shaft 602. The intermediate links 714*a* and 714*b* are connected at their other ends to the grip members 406*a* and 406*b* at rotational couplings 718*a* and 718*b*, allowing the intermediate links to rotate with respect to the grip members 406*a* and 406*b*.

In response to the main shaft 602 being moved along axis 412, force is transmitted from the shaft 602 along the intermediate links 714*a* and 714*b* to the grip members 406*a* and 406*b*. This causes force in the rotational degrees of freedom of the grip members 406*a* and 406*b*, e.g., around the axes at couplings 409*a* and 409*b*, respectively. In the described implementation, the rotational coupling 716*a* is positioned on the opposite side of axis 412 from the grip member 406*a* that receives force from the link 714*a* connected to that rotational coupling 716*a*. Similarly, the rotational coupling 716*b* is positioned on the opposite side of axis 412 from the grip 406*b* that receives force from the link 714*b* connected to that rotational coupling 716*b*. These connections cause the intermediate links 714*a* and 714*b* to cross in a scissor configuration when viewed from the side as in FIGS. 7A and 7B. In some implementations, the shaft end of intermediate link member 714*a* is coupled to the shaft 602 at a first location of the shaft at coupling 716*a* that is spaced further from the grip member 406*a* than a second location of the shaft at coupling 716*b*. The shaft end of the intermediate link member 714*b* is coupled to the shaft 602 at the second location of the shaft at coupling 716*b* that is spaced further from the grip member 406*b* than the first location of the shaft at coupling 716*a*.

In some implementations, the intermediate links 714*a* and 714*b* can rotate in respective planes approximately parallel to each other, e.g., close to and not touching each other. For example, the intermediate links 714*a* and 714*b* can be positioned in planes offset to one side of the axis 412 such that these planes do not intersect the axis 412. In some implementations, the intermediate links 714*a* and 714*b* can be positioned on opposite sides of the axis 412.

In FIG. 7B, the grip members 406*a* and 406*b* have been positioned in a "closed" position, e.g., the grip members are at a position in which their disconnected ends are closest to each other. To obtain this position from the position shown in FIG. 7A, the actuator 411 provides a force in the direction 703 toward the grip members 406*a* and 406*b*. For example, the moving portion 604 of the actuator 411 can be moved in direction 703. Moving portion 604 causes the main shaft 602 to move in direction 703.

The movement of main shaft 602 in direction 703 causes the rotational couplings 716*a* and 716*b* to be moved in that same direction. This causes the intermediate links 714*a* and 714*b* to exert force on the grip members 406*a* and 406*b* in the directions in which they are rotated towards each other. The grip members 406*a* and 406*b* can be rotated in this manner until reaching the closed end position as shown in FIG. 7B.

The spring 708 can be tensioned to have a rest position such that force is exerted on the main shaft 602 in the direction 702 (shown in FIG. 7A) when the grip members are in the closed position shown in FIG. 7B. This causes a force that biases the grip members 406*a* and 406*b* to move away from each other in some or all of the movement range of the grip members 406*a* and 406*b*. In some implementations, multiple springs can be connected to the main shaft 602 to provide multiple different resistances for the degrees of freedom of the grip members 406*a* and 406*b*. For example, concentric springs can be provided, where one of the springs is providing resistance in an initial position range of the grip members, until a second position range of the grip members in which the second spring is encountered such that both springs provide resistance to the grip member motion. Additional springs can also be used for additional resistance at other position ranges.

In some implementations, other mechanisms can be used. For example, the intermediate links 714*a* and 714*b* can be provided in different configurations connecting the main shaft 602 to the grip members 406*a* and 406*b*. In some examples, the rotational couplings 716*a* and 716*b*, and/or 718*a* and 718*b*, can be positioned in different locations on their respective components. In some implementations, rotational couplings 716*a* and 716*b* can be co-located to rotate about the same axis.

FIG. 8 is a diagrammatic illustration of an example arm assembly 800 or portion thereof, which can be used for one or more of the arm assemblies 120 of the manipulator slave device 104 shown in FIG. 1, and which in some implementations can be controlled by master controller implementations described herein. Arm assembly 800 can include multiple links 802, 804, and 806 coupled to each other by rotational couplings. For example, link member 802 can be coupled to a grounded structure, link member 804 can be coupled to link member 802, and link member 806 can be coupled to link member 804. Each link member can be coupled to the other link member(s) at rotational axes sensed and driven by sensors and actuators, allowing portions of arm assembly 800 to be actuated and sensed about rotational axes 810, 812, and 814. Some implementations can provide additional actuated and/or sensed motion of the arm assembly, e.g., about axes extending lengthwise through the links 802, 804, and 806, thus allowing rotation about axes 820, 822, and 824. One example of a surgical manipulator arm is a da Vinci® surgical system instrument manipulator arm available from Intuitive Surgical, Inc. of Sunnyvale, Calif.

An end effector mechanism 840 can be coupled to the end of link member 806 and provides an end effector 842 at its distal end. The end effector 842 is provided the degrees of freedom provided by the rotation of the link members 802, 804, and 806 as described above. End effector mechanism 840 additionally can provide linear motion to the end effector 842 along a linear axis 844. Furthermore, end effector mechanism 840 can provide rotational and other degrees of freedom to the end effector 842 as described below with reference to FIG. 9. In some examples, actuators and sensors included in a mechanism 846 of the end effector mechanism 840 can provide such degrees of freedom to the end effector 842.

In some implementations, components in the arm assembly 800 can function as force transmission mechanisms to receive teleoperated servo actuation forces and redirect the received forces to operate components of the end effector 842. In some examples, end effector 842 receives multiple separate actuation inputs from the end effector mechanism 840 and/or other arm assembly components, e.g., where the number of actuation inputs depend on the number of instrument features to be controlled. In other examples, the end effector 842 can include one or more motors or other actuators that operate associated features of the end effector. Some implementations can control end effector features such as the pitch, yaw, and/or roll of the end effector 842, opening jaws of the end effector 842, the output of material transported through a connecting tube and out of end effector 842 (e.g., liquid or other fluids), suction forces provided by end effector 842, and/or any of a multiple of other end effector functions (e.g., moving a blade, etc.).

FIG. 9 is a perspective view of one example of an end effector 900. For example, end effector 900 can be used as end effector 842 of the arm assembly 800 as referenced above with respect to FIG. 8. End effector 900 is an example surgical instrument that can operate as forceps in a surgical procedure to grasp tissue, objects, etc. Other types of surgical instruments and end effectors can be used in other implementations as described elsewhere herein.

End effector 900 can be provided at a distal end of a main tube 910 which can be coupled to another portion of the end effector mechanism 840 shown in FIG. 8, for example. A proximal clevis 912 is coupled to the distal end of main tube 910, and a distal clevis 914 is coupled to the proximal clevis 912 by a rotational coupling. The forceps end effector 900 includes jaws 916 and 918 that are coupled to the distal clevis 914 by a rotational coupling.

The jaws 916 and 918 are provided with several physical degrees of freedom that can be manipulated by the master controllers 210 and 212 of the master control workstation 102 (shown in FIGS. 1 and 2). For example, the jaws 916 and 918 can be rotated about axis 930 of the link between the jaws and the distal clevis 914, e.g., to open and close the jaws with respect to each other as shown by arrow 932, and/or to rotate the jaws in conjunction to a different rotational position. In addition, the jaws 916 and 918 can be rotated about axis 934 of the link between distal clevis 914 and proximal clevis 916, e.g., to rotate the jaws in space. In addition, the jaws 916 and 918 can be translated along linear axis 936, which in some implementations can correspond to the linear axis 844 shown in FIG. 8.

When using the example master controller portion 400 of FIGS. 4-6, movement of the end effector 900 in one or more degrees of freedom can correspond to movement in one or more degrees of freedom of the master controller handle 402 by a user. For example, the positions of grip members 406*a* and 406*b* of controller portion 400 in their degrees of freedom can control corresponding rotational positions of the jaws 916 and 918 about axis 930. The motions of the jaws 916 and 918 in other degrees of freedom of the end effector can be controlled by particular associated degrees of freedom of a master controller 210 or 212.

In some implementations, one or more of the degrees of freedom of the end effector 900 can be controlled using tendons, e.g., cables (not shown), that are mechanically coupled to one or more of the elements 914, 916, and 918 and extend through tube 910 to a transmission or other mechanism. For example, the tendons can be coupled to pulleys and/or other transmission elements driven by actuators and sensed by sensors provided in mechanism 846 coupled to arm assembly 800 as shown in FIG. 8.

In some examples, the end effector 900 can be inserted through a patient's body wall (or simulated body wall) to reach a surgical site. In some implementations, main tube 910 may include a cavity that can provide material transfer along the tube. For example, material may be transferred between a distal end and a proximal end of tube 910, or points near the proximal end and near the distal end of tube 910. For example, main tube 910 (or other tube) can couple a surgical irrigation fluid (liquid or gas) source (not shown) to the end effector 900 so that irrigation fluid can be routed from a source through the main tube to exit via end effector 900. Similarly, main tube 910 can couple a surgical suction source (not shown) to end effector 900 so that material from a surgical site can be drawn into end effector 900 and through tube 910 to the source. Other types of connection features can be provided in other implementations.

Other types of arm assemblies and types of end effectors can be used in other implementations. For example, end effector mechanisms and instruments can include flexible elements, articulated "snake" arms, steerable guide tubes, catheters, scalpels or cutting blades, electro-surgical elements (e.g., monopolar or bipolar electrical instruments), harmonic cutters, scissors, forceps, retractors, dilators, clamps, cauterizing tools, needles, needle drivers, staplers, drills, probes, scopes, light sources, guides, measurement devices, vessel sealers, laparoscopic tools, or other tip, mechanism or device.

Figure 10:
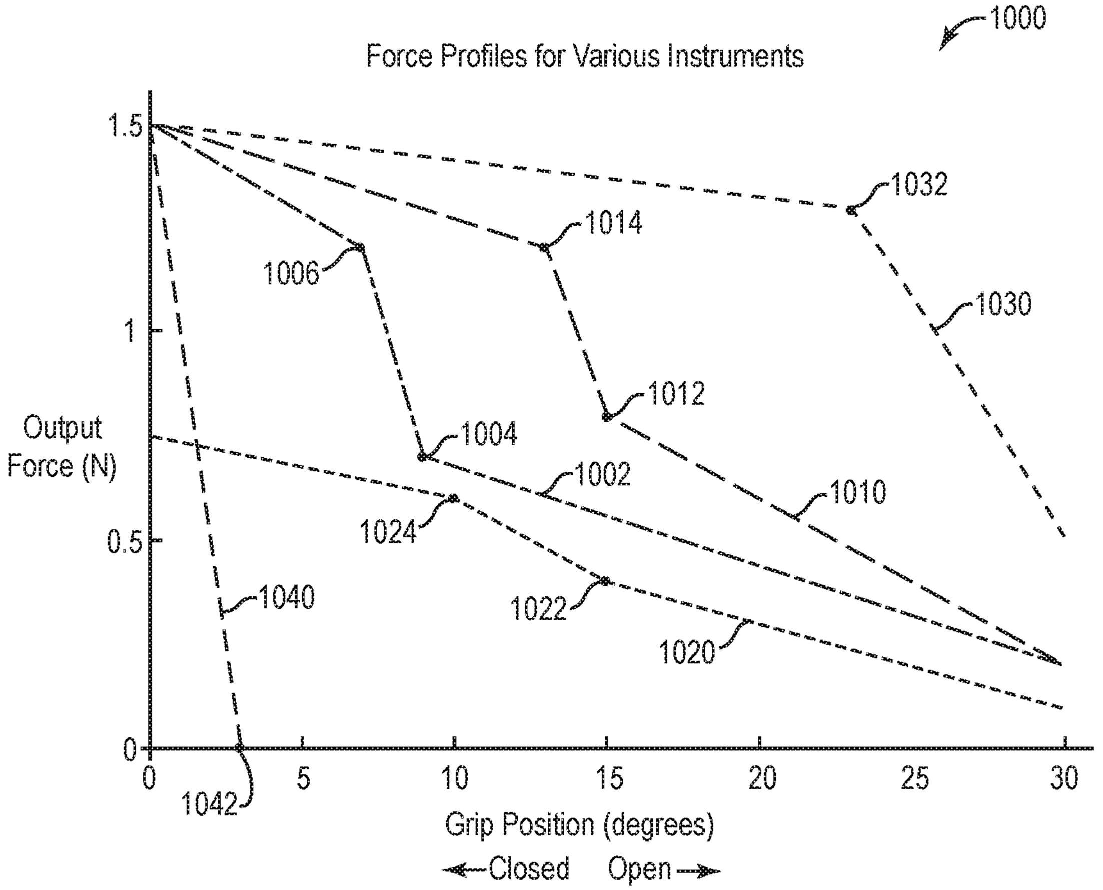
FIG. 10 is a diagrammatic illustration of a graph of example output force profiles that can be used with one more features described herein, according to some implementations.

FIG. 10 is a diagrammatic illustration of a graph 1000 of example output force profiles that can be used with one or more features described herein. Graph 1000 has a vertical dimension indicating a scale of an output force that is provided on a handle, e.g., the master controller handle 402 as described above with reference to FIGS. 4-7B. For example, the output force can be output on each of the grip members 406*a* and 406*b* in the rotary degrees of freedom 408*a* and 408*b*, respectively, using the active actuator 411 and a transmission mechanism including main shaft 602 and intermediate links 714*a* and 714*b*. In some examples, the output force (grip force) can be output in directions on the grip members 406*a* and 406*b* to bias the grip members towards or away from each other, as provided by the link structure shown in FIGS. 7A and 7B.

Graph 1000 has a horizontal dimension indicating a range of grip positions, e.g., the angular position of a grip member 406*a* or 406*b* in its rotary degree of freedom. In this example, the horizontal dimension ranges from the left edge of the graph that corresponds to the closed position of the grip member (e.g., as in FIG. 7B) to the right edge of the graph that corresponds to the open position of the grip member (e.g., as in FIG. 7A).

A number of different force profiles are shown which, in some implementations, can be used in association with the grip members 406*a* and 406*b* to provide different forces for different grip member positions. For example, different force profiles can be used to apply different forces when controlling different types of end effectors of a slave device. A force profile indicates the particular force output on a grip member 406*a* or 406*b* at a particular position of the grip member in its rotary degree of freedom. In some implementations, a force profile can indicate the force output on both grip members 406*a* and 406*b* at corresponding positions in their degrees of freedom, e.g., using the mechanisms of FIGS. 4-7B. In some implementations, the force profile can be the result of an actuator force output from an active actuator (e.g., actuator 411) in combination with a passive force provided by a passive actuator such as spring 708. In some examples, to achieve a particular force profile output, the actuator force output may vary based on the linearity of the mechanical system between the actuator and the grip members and based on the involved forces from spring 708, e.g., as indicated below in examples of FIGS. 11A-11B.

In some examples, a force profile can be defined by a force output function that indicates the output force on the grip member based on the position of the grip member, e.g., a linear function, an exponential function, etc. In further examples, one or more of the force profiles can describe a multiple-stage force output, where different force output functions can be used at different ranges of positions of a grip member to provide different force sensations on the grip member at the different position ranges. For example, a multiple-stage force profile can include multiple different linear force output functions that indicate the amount of force output on a grip member at the positions of the grip member in an associated range of positions in the degree of freedom. In some examples, multiple linear functions of a force profile can have different slopes, or other characteristics or shapes so as to provide different sensations to the user at different position ranges of the grip member. For example, a more resistant spring force can be output in one position range, a force bump can be output in a different position range, etc.

In some examples, a force profile 1002 can describe a multiple-stage force output on the grip members 406*a* and 406*b* which can be enabled by implementations of actuators and mechanisms described herein. Three different example stages are shown, each using a linear force output function. For example, at an open position of the grip members, represented at the right edge of the graph 1000, force profile 1002 indicates that a smaller output force applied in the directions of the degrees of freedom that force the grip members apart from each other, thus allowing a user to move the grip members together more easily. As the grip members are moved closer toward each other, corresponding to a direction from right to left on the graph 1000, the force opposing this motion is increased linearly as shown on the right linear section of profile 1002. At a point 1004 of the profile 1002, the opposing output force is ramped up with a higher slope (e.g., higher increase in opposing force from left to right on graph 1000) for positions closer to the closed position of the grip members. This increase in opposing force can be a "bumper" that notifies the user of a particular position in the range of motion of the grip members 406*a* and 406*b*. In some examples, this increased force is provided for a short range of positions between points 1004 and 1006, and then at point 1006 the opposing force is increased at a more gradual (lower) rate for positions of the grip members closer to each other (to the left of point 1006 on profile 1002), e.g., the increase in opposing force is less to the left of point 1006 than the increase in opposing force between points 1004 and 1006, in a direction from left to right. In some examples, the change in force to the left of point 1006 to a more gradually-increasing force can cause the higher-sloped increase in force output from point 1004 to point 1006 to be more noticeable to the user. For example, in some implementations, a user may be more sensitive in feeling changes or transitions in the rate of force output (e.g., at points 1004 and 1006) than in changes of force provided at a constant rate (e.g., between points 1004 and 1006).

In some examples, the force bumper provided by the changes in force output to the left of point 1004 can describe resistance to closing the grip members 406*a* and 406*b* which can to notify the user. For example, a particular instrument used for a controlled end effector may cause a particular action or effect if commanded by the grip members to close past the point 1004 from left to right in the graph 1000. In one example, a forceps-like instrument (e.g., forceps end effector 900) may hold a particular item between its jaws. If the grip members 406*a* and 406*b* are moved closer to each other than (to the left of) the position at point 1006, the jaws will be fully closed. The increase in force output at point 1004 can thus reduce the likelihood that the user will inadvertently move the grip members 406*a* and 406*b* closer together than the position at point 1006. In addition, the increase in force output can notify the user that the grip members 406*a* and 406*b* have reached the position beyond which the forceps will be closed. In this and other examples, a sudden change in stiffness followed by an increase in stiffness as the grip members are moved in particular directions (e.g., toward the closed position) can signify to the user a controller movement zone to be entered with user intent.

In some implementations, the force profile 1002 can simulate the use of two physical springs concentrically positioned, one inside the other, that provide resistance to the grip members 406*a* and 406*b*. For example, the force output to the right of point 1002 of force profile 1002 can simulate the simulated compression of a first spring before a second spring has been contacted. The force output between points 1004 and 1006 can be the simulated compression of both the first spring and a second spring that has a partial preloaded compression, which causes a greater rate of resistance to closing the grip members between points 1004 and 1006. The force output to the left of point 1006 can be the simulated compression of the first spring and the second spring, where the second spring is compressing after having moved through its preload in the region between points 1004 and 1006.

A force profile 1010 can describe a multiple-stage force to be output on the grip members 406*a* and 406*b*. Force profile 1010 can be similar to force profile 1002 by having three stages with linear force output functions. For example, the force output for positions to the right of point 1012 on the force profile 1010 provide resistance to closing the grip members 406*a* and 406*b* from a fully open position (represented at the right limit to profile 1010). For grip positions between point 1012 and point 1014 on the profile 1010, an increased force is output, resisting closure of the grip members 406*a* and 406*b*. For grip positions closer to the closed position than (to the left of) point 1014 on profile 1010, the rate of increase in output force resisting closure is reduced relative to the stage between points 1012 and 1014.

In some examples, the force profile 1010 can be provided when controlling an end effector that is different than an end effector controlled using the force profile 1002. For example, the point 1012 on profile 1010 occurs closer to the fully open position of the grip members 406*a* and 406*b* than the corresponding point 1004 of force profile 1002. This causes a force "bumper" at a different position of the grip members. For example, this can be useful for particular types of end effectors. In one example, a bipolar cautery instrument may require that the jaws of the controlled instrument be apart by a particular distance or less in order for cauterizing energy to pass between the jaws of the instrument. The point 1012, and the change in force output at that point, can indicate that particular distance, e.g., can indicate the position of the grip members 406*a* and 406*b* that will cause the jaws of the instrument to be positioned at that particular distance.

A force profile 1020 can describe a multiple-stage force to be output on the grip members 406*a* and 406*b*. For example, force profile 1020 can provide three different force output stages similarly to force profiles 1002 and 1010, where point 1022 on force profile 1020 is similar to points 1004 and 1012 of force profiles 1002 and 1010, and point 1024 on force profile 1020 is similar to points 1006 and 1014 of force profiles 1002 and 1010. In some examples, force profile 1020 can be used in the control of a different type of instrument at the end effector. For example, the force output at grip positions between points 1022 and 1024 has a lower slope and is closer to the rightmost stage of force profile 1020 than corresponding output forces used for profiles 1002 and 1010. This causes the force bumper between points 1020 and 1022 on profile 1020 to be less noticeable to the user operating the grip members 406*a* and 406*b*. For example, some instruments may not need a strong force bumper to indicate a particular position of the grip members or particular instrument state. In some implementations, the less-noticeable force bumper of the force profile 1020 can be used to more subtly indicate a particular grip position to the user.

A force profile 1030 can describe a two-stage force applied to the grip members 406*a* and 406*b*. The force output for grip positions to the right of point 1032 on the force profile 1030 provide resistance to closing the grip members 406*a* and 406*b* from a fully open position. For grip positions to the right of point 1032 on the profile 1030, a force is output on the grip members 406*a* and 406*b* that increases at a greater rate (e.g., greater slope) from right to left than in the rightmost stages of the force profiles 1002, 1010, and 1020. For grip positions to the left of point 1032 on profile 1030, the change in output force is reduced so that it is almost flat, e.g., an almost constant force output at the grip positions from point 1032 to the closed position at the left.

In some examples, the force profile 1030 can be used in the control of a particular type of end effector. For example, a particular end effector instrument may provide a particular action or effect if commanded with grip positions to the left of the point 1032. In one example, the end effector instrument can be a clip applier that has jaws similar to a forceps instrument, and which are specialized to hold an open clip between its jaws. The clip applier jaws can be closed to permanently close the clip, where a closed clip can be used to join or attach portions of surgical tissue, for example. In the force profile 1030, the point 1032 can indicate a closing grip position, where grip positions to the left of the point

1032 will cause the controlled clip applier to close, which in turn causes the held clip to close. The grip positions to the right of point 1032 can thus receive increased resistance as shown for profile 1030. The user has to overcome a stronger resistance to move the grips past the point 1032, thus reducing the likelihood that the user operator will inadvertently close the grips past the point 1032 and thus inadvertently close a held clip. Some implementations can position the point 1032 further to the left on the force profile 1030, e.g., to provide more movement range for the grip members when moving from the open position before the grip members encounter a bumper indicating the position to close the clip.

A force profile 1040 can describe a single-stage force applied to the grip members 406*a* and 406*b*. For example, a linearly-increasing spring force can be applied to the degrees of freedom of the grip members 406*a* and 406*b*, or to a portion of the degrees of freedom. In the example of force profile 1040, a linearly-increasing force is applied to the grip members within a small range of grip positions adjacent to the closed position of the grip members at the left side of the graph 1000 (e.g., about 3 degrees of the 30 degree range of grip positions). This force output allows the grip members to feel a steeply-increasing force resistance the closer they are moved to the closed position.

In some implementations, the grip members can be held, or can be biased to be held, to maintain a position within a controlled and/or predefined range portion of their degrees of freedom, e.g., a limited range of positions, due to actuator forces provided by the active actuator. The predefined range portion can be a subset of positions of the full range of positions allowed in the degree of freedom of the grip member. For example, in some implementations using force profile 1042, the grip members 406*a* and 406*b* can be held to an approximate position 1042 (or within a small range of positions approximately centered on position 1042), e.g., at about 3 degrees from the closed position. In the example of FIGS. 4-7B, to hold the grip positions, the actuator 411 outputs force on the main shaft 602 in the opposite direction to the force output shown in graph 1000 so that the grip members 406*a* and 406*b* resist being opened further by the force provided from the physical spring 708. The actuator 411 can hold this position of the grip members whether or not the user is touching or holding the grip members. If a user moves the grip members closer to a closed position from the held position 1042, the grip members are allowed to close, with a force resisting the closing motion as indicated by force profile 1040. In some examples, this small range of motion of the grip members allowed near the closed position can be used in some implementations to relieve stress or tension on a user's fingers or hands during use of the grip members by the user, e.g., caused by the user holding the grips tightly.

Some implementations can hold the grip members to a single position or a small sub-range of the grip member's movement when controlling particular types of instruments as the end effector. For example, a hook (e.g., cautery hook), probe, spatula, or other type of instrument that has a single tip or monopole can be controlled by the handle 402 having the grip members 406*a* and 406*b* held in a closed position, or held close to a closed position, e.g., using a force profile similar to profile 1040. The degrees of freedom of the controller portion 400 other than the grip member degrees of freedom can be used to control and move the end effector in corresponding degrees of freedom in space.

In other implementations, the grip members 406*a* and 406*b* can be held at other positions or sub-ranges of positions in the degrees of freedom of the grip members, e.g., in the middle of the degree of freedom, near the open position of the grip members 406*a* and 406*b*, etc. In some implementations, if a force profile indicates that an amount of force should be quickly changed by a large magnitude (e.g., more than a particular threshold amount of force), then the force can be gradually changed from its current output to the indicated level of output, e.g., ramping the forces. For example, a user may suddenly be detected using the controller, causing a sudden change of output from zero force to a high magnitude force indicated by the force profile. Such a force can be gradually ramped up to the indicated high magnitude. In another example, the grip members may be being held at a closed position by the actuator force during use, and then a condition occurs to cause the force to be removed from the grips. If the force is quickly removed, this may allow the spring to force open the grips quickly, which may be alarming to the user. Thus, the actuator force can be ramped down by the actuator and gradually removed from the grip members to reduce this effect.

Some implementations can allow user or operator customization of force profiles. For example, if a particular user prefers that a large range of motion be provided to the grip members to control a particular instrument, then a force profile providing a normal (smaller) range of motion of the grip members can be changed to a different force profile that allows a larger range of motion to be more easily used (e.g., by moving a force change point such as point 1004 further to the left in the graph of FIG. 10). In some implementations, a different set of customized force profiles can be associated with different users. For example, the identity of the user using the master controller can be determined, e.g., using any of known techniques such as user login with password, user biometrics recognition (voice, fingerprint, retina, etc.), and other techniques. A stored set of customized force profiles associated with that user can then be selected and used during controller operation. These force profiles can also be selected based on the type of end effector being used, as described herein.

In some implementations, a single grip member 406*a* or 406*b* can be moved and actuated independently of the other grip members. For example, each a grip member 406*a* and 406*b* can receive force derived from output of a respective associated actuator. One of such independent grip members 406*a* and 406*b* can receive forces to achieve a different force profile than the other grip member 406. In some examples, one grip member 406*a* or 406*b* can be held at or close to a closed position, e.g., based on force profile 1040, and the other grip member 406*b* or 406*a* can be provided with forces based on a different force profile, e.g., force profile 1002, 1010, etc. In some implementations, an end effector can be controlled based on movement of one grip member 406*a* or 406*b* in its degree of freedom, e.g., the grip member controlled by force profile 1002 or 1010.

In some implementations, other types of force profiles can be used. For example, force profile curves can include bumps or spikes, e.g., where the profile goes higher to a point and then lower than the point in the direction from left to right. Some implementations can use force profiles that are discontinuous or otherwise have large jumps in force output. For example, in the direction from left to right on graph 1000, the profile can stop at a first grip position and resume for further positions at a different output force that is higher or lower than the output force at the first grip position.

Figure 11A:
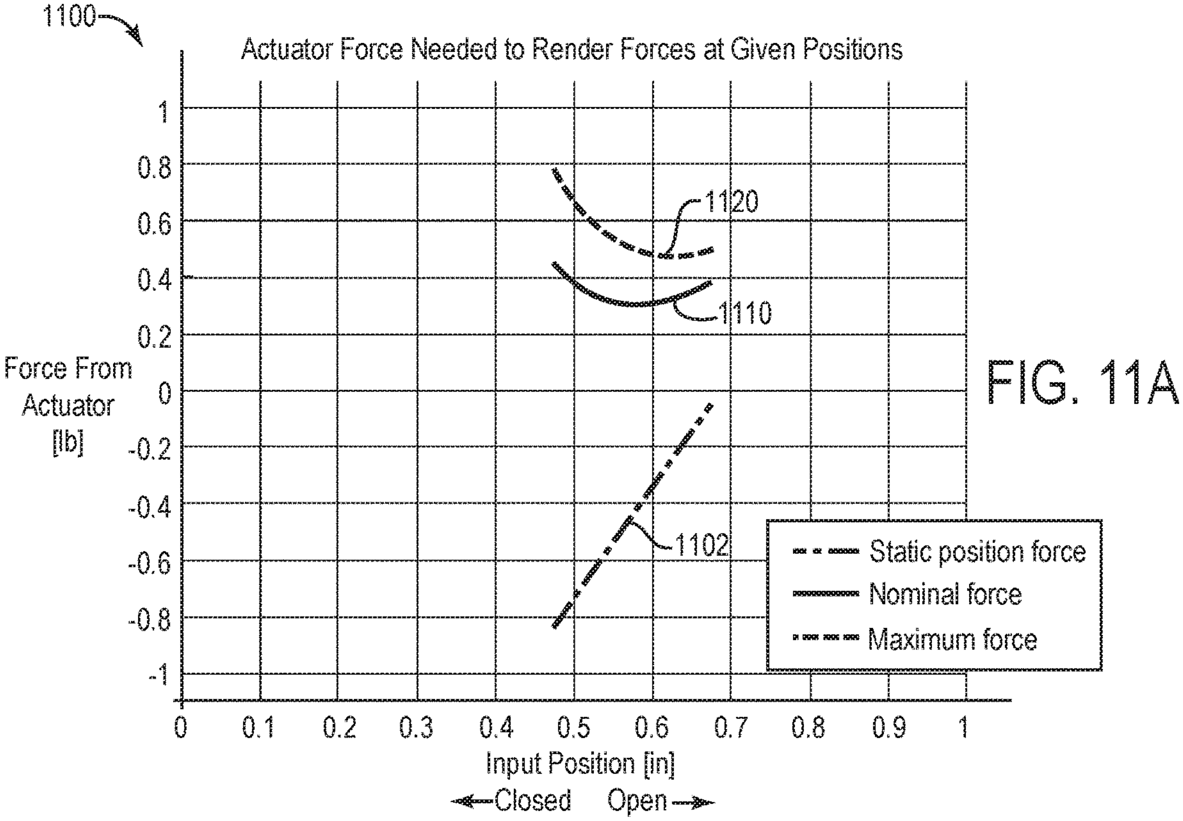
FIGS. 11A and 11B are diagrammatic illustrations of graphs of example actuator force profiles, according to some implementations.

FIG. 11A is a diagrammatic illustration of a graph 1100 of example actuator force profiles that show example forces output by an actuator over a position range of a controller handle. In this example, graph 1100 has a vertical axis indicating an example scale of an output force that is provided by the actuator 411 onto the main shaft 602 as shown in FIGS. 6 and 7A-7B. A positive force on this axis indicates a force in the linear direction on the main shaft that biases the grip members 406*a* and 406*b* toward their open position, and a negative force on this axis indicates a force that biases the grip members 406*a* and 406*b* toward their closed position. Graph 1100 has a horizontal dimension indicating an example range of positions of a component of the controller receiving force from the actuator, e.g., the positions occupied by the main shaft 602 or a moving portion of an actuator. In this example, the horizontal dimension ranges from the left edge of the graph that corresponds to the shaft position at the closed position of the grip members (e.g., as in FIG. 7B) to the right edge that corresponds to the shaft position at the open position of the grip members (e.g., as in FIG. 7A). The force curves shown in graph 1100 can be similar to force curves for mechanisms other than the implementations of FIGS. 4-7B.

A force curve 1102 indicates forces required to be output by the actuator 411 to causing a resulting force that maintains the grip members 406*a* and 406*b* at approximately a static position in their degrees of freedom. The actuator 411 outputs a force that maintains the grip members 406*a* and 406*b* in opposition to the force provided by the spring 708. The spring biases the grip members 406*a* and 406*b* toward the open position, so the forces of curve 1102 are in the negative direction that bias toward the closed position. The curve 1102 shows a linear output required over the range of positions of the main shaft 602, in opposition to the linear force provided by the spring over that range of positions.

A force curve 1110 indicates forces required to be output by the actuator 411 to cause a consistent resulting nominal force on the grip members 406*a* and 406*b*. In one example, the particular nominal force can be a force magnitude at a position of a force profile such as any of the force profiles shown in FIG. 10. Curve 1110 shows positive forces so that the actuator output force works in conjunction with the force provided by the spring 708 to resist closing of the grip members toward the closed position.

The force curve 1110 shows a particular actuator force at the right end of the curve 1110 (e.g., about 0.4 pounds in one example) which is output by the actuator at the open position of the grip members 406*a* and 406*b*. The curve 1110 dips slightly over the curve toward the left of the open position (as the grip members 406*a* and 406*b* are at positions closer to the closed position), and rises again at the left end of the curve 1110 at the closed position of the grip members, corresponding to a force value slightly above the value at the right end of the curve 1110. Thus, force curve 1110 indicates an approximately linear output required by the actuator over the range of positions of the grip members to provide the desired nominal force on the grip members. The actuator output need not be compensated significantly to provide a consistent output force on the grip members 406*a* and 406*b* over the range of motion of the grip members.

A force curve 1120 indicates forces required to be output by the actuator 411 to cause a consistent resulting higher force on the grip members 406*a* and 406*b* than indicated by force curve 1110. For example, the force indicated by curve 1120 can be output by the actuator to provide a particular maximum force level to the grip members (e.g., 1.5 Newtons in some examples). Force curve 1120 can be similarly shaped to force curve 1110, except at higher values of force output by the actuator. A particular actuator force at the right end of the curve 1120 (e.g., about 0.5 pounds in one example) is output at the open position of the grip members 406*a* and 406*b*. The curve 1120 is approximately flat over the curve toward the left of the open position, and then rises near the closed position of the grip members, ending at a force value above the value at the right end of the curve 1110 (e.g., about 0.8 pounds in the example). Thus, force curve 1120 indicates a rising output force required to be output by the actuator as the grip members are moved toward the closed position, in order to provide the desired maximum force on the grip members.

The force curves 1102, 1110 and 1120 also indicate that the range of output of the actuator 411 is being utilized efficiently. For example, force curve 1110 requires a maximum of about −0.8 pounds output force, and force curve 1120 requires a maximum of about 0.8 pounds output force, which are approximately the same in opposite directions.

The shape and range of the curves 1102, 1110, and 1120 can be determined based on the particular mechanisms used in the master controller to provide forces on the grip members. For example, the lengths of the main shaft 602 and other links used in the transmission mechanism, the locations of the couplings between the shaft and links, the properties of the spring 708 (e.g., spring constant, preload), and/or the force output capability of the actuator 411 over its output range can all be tuned to provide curves similar to the force curves shown in FIG. 11A, or other desired force curves. For example, nonlinearity of actuator forces and/or of forces provided by the spring 708 can be compensated in other characteristics of the system, including link lengths and coupling locations between links. Non-linearity of the components can be leveraged to provide a realistic experience of spring forces and other forces on the grip members, and, for example, can allow the user to feel as if he or she is manipulating a controlled object realistically.

Figure 11B:
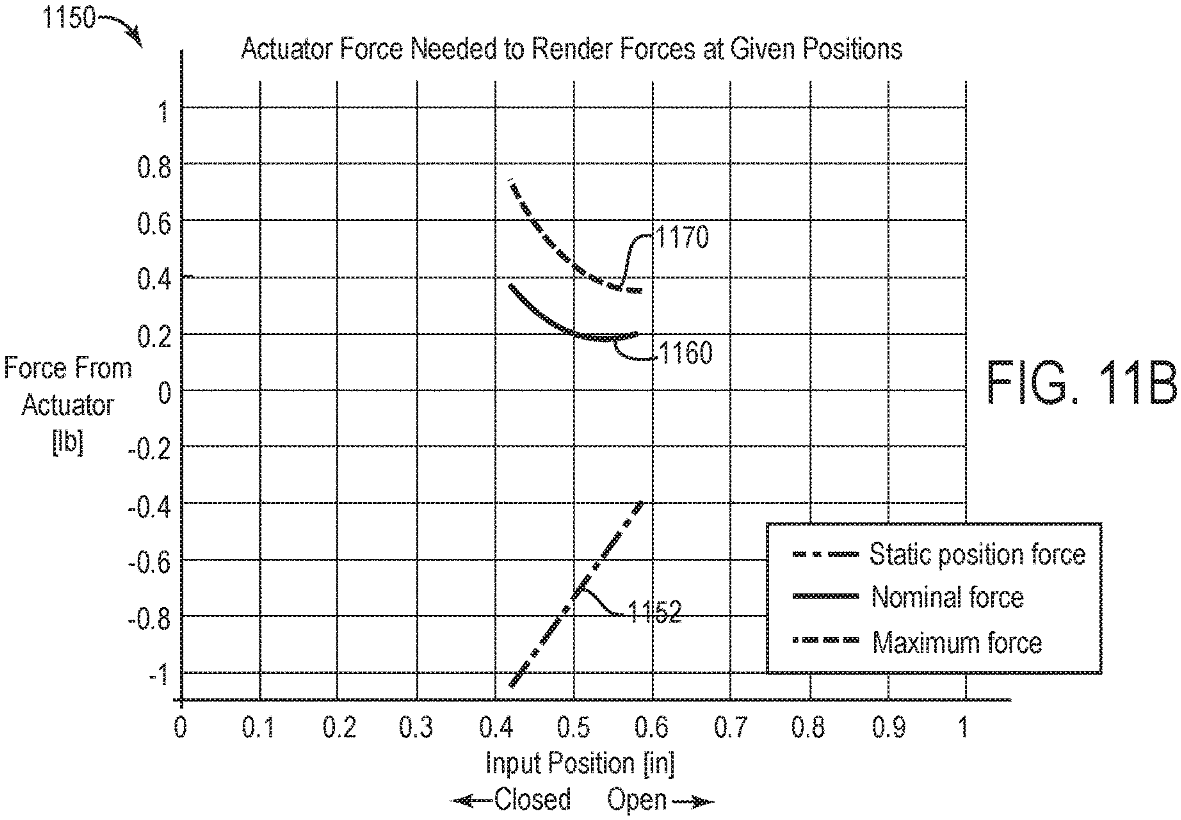

FIG. 11B is a diagrammatic illustration of a graph 1150 of additional example actuator force profiles that show another example effect of force output on grip members 406*a* and 406*b* by an actuator, similarly to FIG. 11A. In some examples, the force curves of FIG. 11B result from a more poorly-matched controller system than the controller system providing the force curves of FIG. 11A.

A force curve 1152 indicates forces required to be output by the actuator 411 to causing a resulting force that maintains the grip members 406*a* and 406*b* at a static position in their degrees of freedom, similarly to force curve 1102 of FIG. 11A. The curve 1152 is different than the curve 1102 in that it requires a different range of output forces from the actuator, e.g., a smaller range, and a more extreme force output at the closed position of the grip members (e.g., about −1 pounds instead of about −0.8 pounds in FIG. 11A). Thus, the mechanism transmitting the forces to the grip members does not spread out the required forces into a greater portion of the range of actuator force output as much as the mechanism used for the force curves of FIG. 11A.

A force curve 1160 indicates forces required to be output by the actuator 411 to cause a consistent resulting nominal force on the grip members 406*a* and 406*b*, similarly to force curve 1110 of FIG. 11A. Curve 1160 is less consistent than curve 1110. For example, the force for the open position is about 0.2 pounds, and the required force for the closed position is about 0.4 pounds, which is a more extreme difference than in curve 1110. The mechanism used for curves 1160 and 1170 does not perform consistently over the position range of the grip members, and requires significant compensation from the actuator.

A force curve 1170 indicates forces required to be output by the actuator 411 to cause a consistent maximum force level force on the grip members 406*a* and 406*b* that is higher than the forces for force curve 1160. This is similar to force curve 1120 of FIG. 11A. Curve 1170 is less consistent than curve 1120 or curve 1160. For example, the required force for the open position is less than 0.4 pounds, and the required force for the closed position is about 0.7 pounds, which is a more extreme difference than in curve 1120. The mechanism used for curve 1170 does not perform as consistently over the position range of the grip members as the mechanism used for curve 1120, requiring more compensation from the actuator.

In some implementations, the mechanism used to determine the force curves 1152, 1160, and 1170 can be considered more poorly executed than the mechanism used to determine the force curves of FIG. 11A. In a poorly-executed system, for example, the force on the grips may drop off as the user closes the grips or the force output may otherwise act erratically, resulting in a controller that may feel uncontrollable and unnatural. In some examples, the controller used for FIG. 11B can differ from the controller used for FIG. 11A by having one or more different lengths for grip members 406*a* or 406*b*, one or more different lengths for intermediate link members 714, different spring properties for spring 708, different location of the rotational couplings between the grip members 406 and the link members 714, etc.

Figure 12:
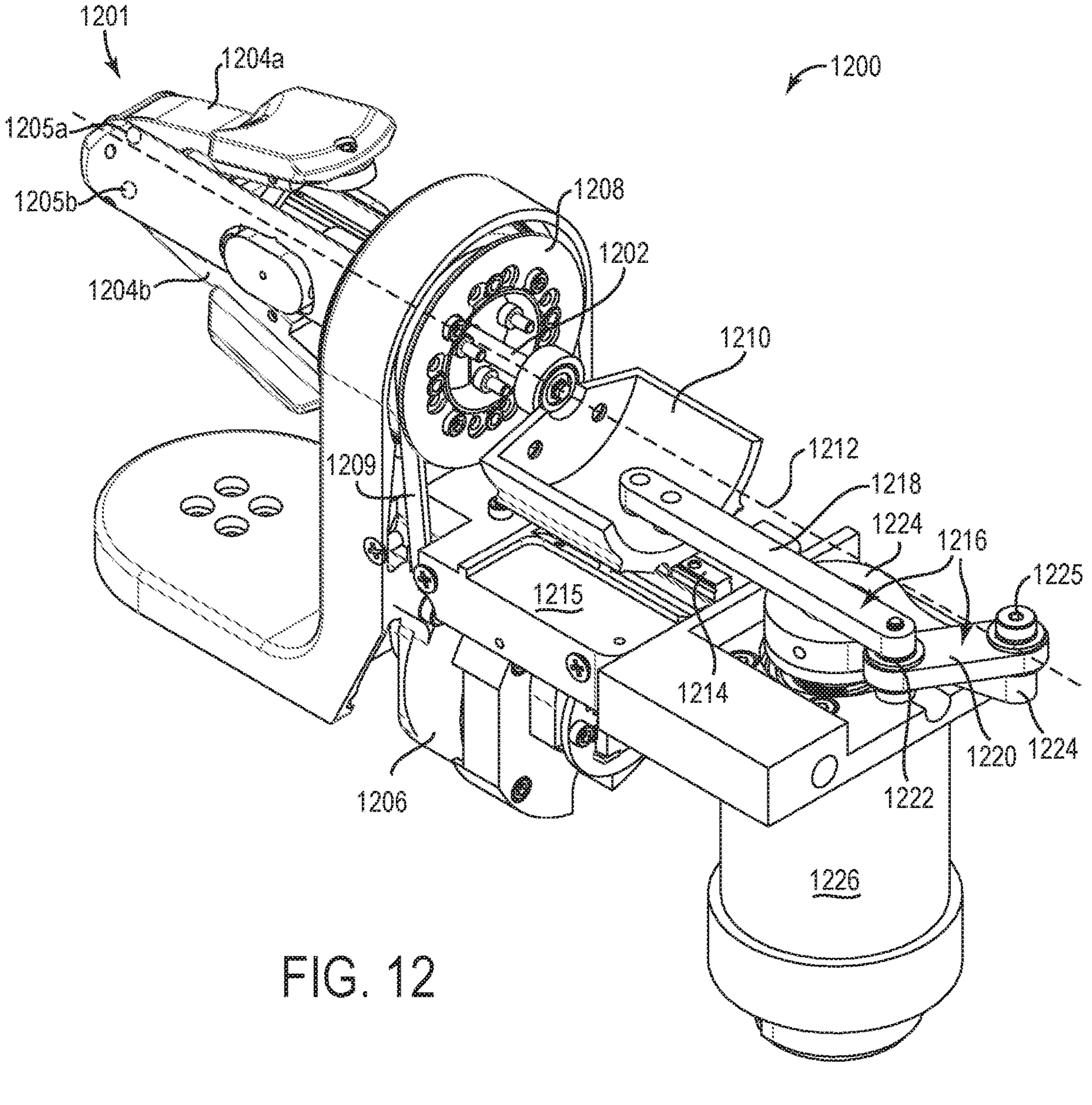
FIG. 12 is a perspective view of an example controller portion including a crank arm transmission providing a linear force output from a rotary actuator, according to some implementations.

FIG. 12 is a perspective view of an example implementation of a controller portion 1200 including a crank arm transmission providing a linear force output from a rotary actuator. For example, a master controller handle 1201 can be similar to the master controller handle 402 described above with respect to FIGS. 4-7B, or a different handle can be used. Handle 1201 and controller portion 1200 can include one or more of the features described for handle 402 and other implementations described herein.

Controller portion 1200 can include a main shaft 1202 connected to and driving grip members 1204*a* and 1204*b* similarly to corresponding components in the implementations described above for FIGS. 4-7B. In some implementations, an actuator 1206 can be coupled to a pulley 1208 by a belt 1209 to provide rotation of the controller handle 1201 similarly as described above with reference to FIG. 6.

Main shaft 1202 can be connected to the crank arm transmission that includes a rail piece 1210, linkage 1216, and crank 1224. The main shaft 1202 is decoupled in rotation to the carriage piece 1210 so that the shaft can rotate about axis 1212 (e.g., longitudinal axis of main shaft 1202) independently of the carriage piece 1210 and is linearly coupled to the carriage piece 1210 along the lengthwise axis 1212. In some implementations, the carriage piece 1210 can be constrained linearly along or parallel to the axis 1212 of the main shaft 1202 by a slot on the bottom of the carriage piece 1210 that engages a guide rail 1214 that is coupled to the link 1215, similarly as described above for the moving portion of the voice coil actuator 411 of FIGS. 4-6. A linkage 1216 includes a first link 1218 that is rigidly coupled to the carriage piece 1210 at a first end of the first link 1218, and a second link 1220 that is coupled at a first end to a second end of the first link 1218 at a coupling 1222. A second end of second link 1220 is coupled to a first end of a crank 1224 by a rotational coupling 1225. A second end of crank 1224 is rigidly coupled to the rotating shaft of a rotary actuator 1226, where the rotating shaft of actuator 1226 can be perpendicular to the shaft 1212 of the main shaft 1202. For example, actuator 1226 can be an active actuator in some implementations, e.g., a motor.

The actuator 1226 can output a force on its rotatable shaft to provide rotary force on and motion of the crank 1224. The force on and motion of the crank 1224 causes motion in second link 1220, which causes first link 1218 to move linearly due to the rail 1214 engaged by the carriage piece 1210. The linear motion of first link 1218 and carriage piece 1210 provides linear force on and motion of the main shaft 1202, causing force on and/or motion of the grip members 1204*a* and 1204*b*.

The described mechanism can convert the rotary force output of the actuator 1226 to linear force by mirroring the mechanism used for the grip members 1204*a* and 1204*b*. For example, the first link 1218, second link 1220, and crank 1224 can have rotary couplings that are spaced relative to each other proportionally the same distance as the distance between rotational couplings between the main shaft 1202, an intermediate link (similar to the intermediate links 714*a* or 714*b* shown in FIGS. 7A-7B), and a grip member 1204*a* or 1204*b*, respectively. For example, the crank 1224 can mirror a grip member 1204*a* or 1204*b* and can rotate about the actuator shaft similarly to a grip member 1204*a* or 1204*b* rotating at the coupling 1205*a* or 1205*b*, respectively. The first link 1218 can mirror the main shaft 1202 and the second link 1220 can mirror an intermediate link connecting the main shaft 1202 and a grip member 1204*a* or 1204*b* (e.g., similar to intermediate link 714*a* or 714*b*). The mirrored mechanism allows the actuator 1226 to provide force at the grip members 1204*a* and 1204*b* in a linear relationship. This removes or reduces a need for compensation of actuator output with different output forces at different grip member positions to maintain a consistent force at the grip members 1204*a* and 1204*b* as described above for FIGS. 11A and 11B.

Actuators 1206 and/or 1226 can be any of a variety of types of actuators similarly as described herein for other implementations. For example, active actuators can be used, e.g., motors (e.g., DC motors), voice coils, or other types of active actuators. Passive actuators (e.g., springs, brakes, etc.) can be used in some implementations to provide resistance in particular directions of the grip members, in rotation of the handle 1201 about axis 1212, etc.

Similarly as described in the other implementations herein, one or more sensors can be coupled to the handle 1201 and/or other components of the controller portion 1200 and can detect the positions of the grip members 1204*a* and 1204*b*. For example, in some implementations, a rotary encoder can be included in the housing of actuator 1226 to detect rotation of the shaft of actuator 1226. In some implementations, a linear sensor can be coupled to the link 1215 to sense linear motion of the carriage piece 1210 or link 1218. Similarly, one or more sensors can be coupled to one or more components of the controller portion 1200 and can detect the roll position of the handle 1201 about axis 1212. For example, in some implementations, a rotary encoder can be included in the housing for actuator 1206 to detect rotation of the shaft of actuator 1206. The sensors can send signals describing sensed positions or motion to one or more control circuits of the teleoperated system 100. In some modes or implementations, the control circuits can provide control signals indicating sensed positions or motion to the slave manipulator device 104. The sensors can be any of a variety of types of sensors, e.g., a magnetic sensor (e.g., magnetic incremental linear position sensor, Hall Effect sensor, etc.), optical sensor, encoder, resistance sensor, etc.

Figure 13:
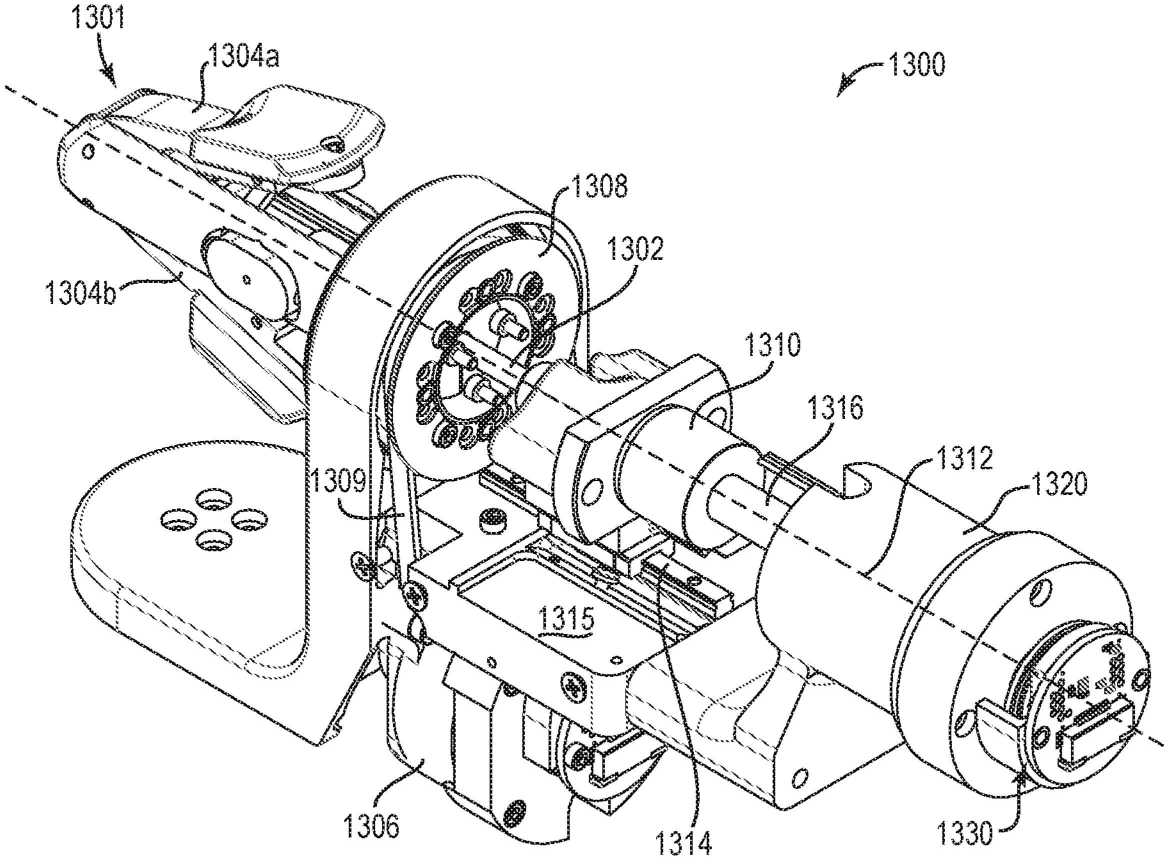
FIG. 13 is a perspective view of an example controller portion including a ballscrew transmission providing a linear force output from a rotary actuator, according to some implementations.

FIG. 13 is a perspective view of an example implementation of a controller portion 1300 including a ballscrew transmission coupled to a rotary actuator. In this example, a master controller handle 1301 can be similar to the master controller handle 402 described above with respect to FIGS. 4-7B, or a different handle can be used. Handle 1301 and controller portion 1300 can include one or more of the features described for handle 402 and other implementations described herein.

Controller portion 1300 can include a main shaft 1302 connected to and driving grip members 1304*a* and 1304*b* similarly to corresponding components in the implementations described above for FIGS. 4-7B. In some implementations, an actuator 1306 can be coupled to a pulley 1308 by a belt 1309 to provide rotation of the controller handle 1301 similarly as described above with reference to FIG. 6.

Main shaft 1302 can be connected to a ballscrew transmission, including a ballscrew nut 1310 and a ballscrew 1316. The main shaft 1302 is linearly coupled to the ballscrew nut 1310 along the lengthwise axis 1312 and is decoupled in rotation to the ballscrew nut 1310 so that the shaft 1302 can rotate about axis 1312 independently of the ballscrew nut 1310. In some implementations, the ballscrew nut 1310 can be constrained in its movement linearly along or parallel to the axis 1312 of the main shaft 1302 by a slot on the bottom of the ballscrew nut 1310 that engages a guide rail 1314 that is coupled to the link 1315, similarly as described above for the moving portion of the voice coil actuator 411 of FIGS. 4-6 and guide rail 1214 of FIG. 12. Ballscrew 1316 is a threaded member that engages a threaded aperture of ballscrew nut 1310. The ballscrew 1316 is rigidly coupled at its other end to the rotating shaft of a rotary actuator 1320.

The actuator 1320 can output a force on its rotatable shaft to cause the ballscrew 1316 to rotate. The rotation of the ballscrew 1316 causes the ballscrew nut 1310 to move linearly along the linear axis 1312 (e.g., longitudinal axis of the ballscrew 1316 and main shaft 1302) as constrained by rail 1314. The linear motion of the ballscrew nut 1310 moves the main shaft 1302 linearly, causing rotational force on the grip members 1304*a* and 1304*b*. The ballscrew transmission thus converts rotary force from rotary actuator 1320 to linear force applied to the main shaft 1302. In some implementations, actuator 1320 can be coupled to a sensor such as a rotary encoder 1330 that determines a rotational position of the actuator shaft and main shaft 1302.

Actuators 1306 and/or 1320 can be any of a variety of types of actuators similarly as described herein for other implementations. For example, active actuators can be used, e.g., motors (e.g., DC motors), voice coils, or other types of active actuators. Passive actuators (e.g., springs, brakes, etc.) can be used in some implementations to provide resistance in particular directions of the grip members, in rotation of the handle 1301 about axis 1312, etc.

Similarly as described in the other implementations herein, one or more sensors can be coupled to the handle 1301 and/or other components of the controller portion 1300 and can detect the positions of the grip members 1304*a* and 1304*b*. For example, in some implementations, in addition to or instead of rotary encoder 1330, a linear sensor can be coupled to the link 1315 to sense linear motion of the ballscrew nut 1310. Similarly, one or more sensors can be coupled to one or more components of the controller portion 1300 and can detect the roll position of the handle 1301 about axis 1312. For example, in some implementations, a rotary encoder can be included in the housing for actuator 1306 to detect rotation of the shaft of actuator 1306. The sensors can send signals describing sensed positions or motion to one or more control circuits of the teleoperated system 100. In some modes or implementations, the control circuits can provide control signals indicating sensed positions or motion to the slave manipulator device 104. The sensors can be any of a variety of types of sensors, e.g., a magnetic sensor (e.g., magnetic incremental linear position sensor, Hall Effect sensor, etc.), optical sensor, encoder, resistance sensor, etc.

Figure 14A:
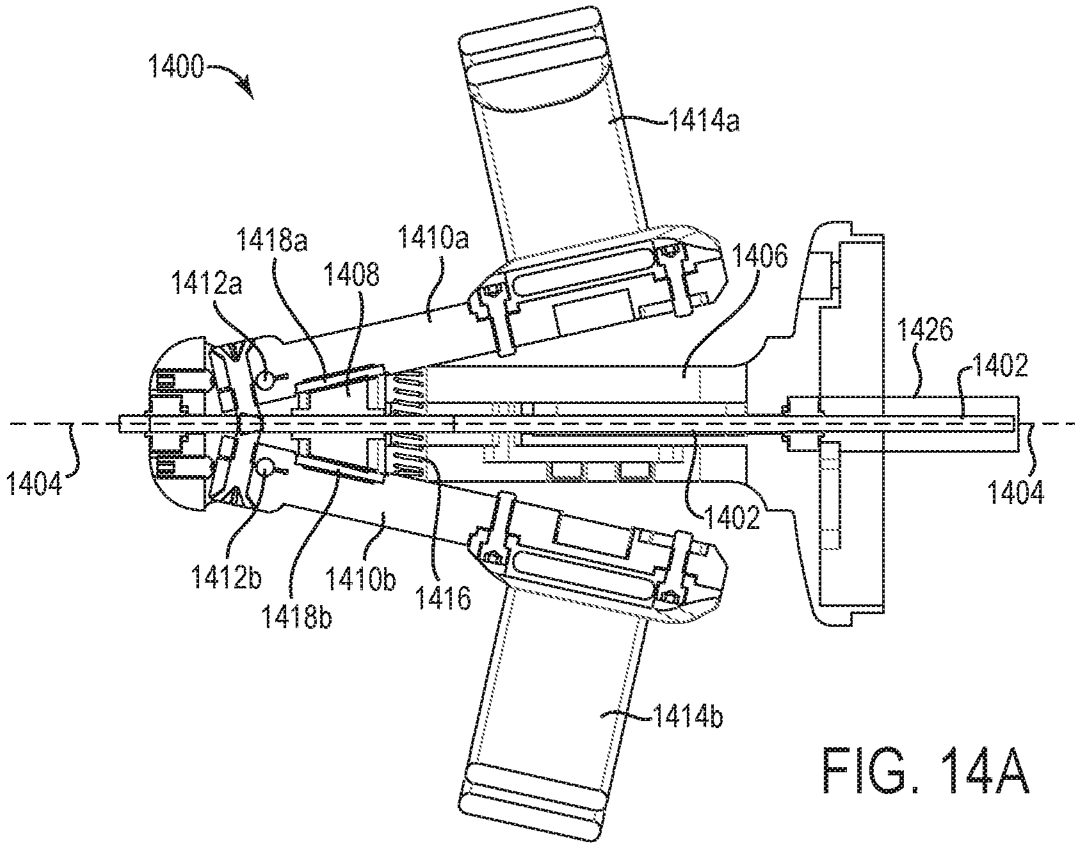
FIGS. 14A and 14B are a views of an example controller portion and cam mechanism to provide forces on controller grips, according to some implementations.

FIG. 14A is a side elevational view of an example implementation of a controller portion 1400 including a cam mechanism to provide forces on controller grips. In some implementations, the main shaft of the controller portion 1400 need not be moved or biased linearly along its lengthwise axis to provide force on the grip members of the handle, and is instead rotated to provide forces on the grip members. Controller portion 1400 can include one or more of the features and components described for handle 402 and other implementations described herein.

A main shaft 1402 can be coupled to an actuator (not shown) that rotates the shaft 1402 about its longitudinal axis 1404. For example, the main shaft 1402 can be rotated by a rotary actuator similarly to actuator 1320 of FIG. 13. In some implementations, an actuator that rotates the main shaft 1402 can be positioned directly in-line with the main shaft 1402, e.g., such that the rotated shaft of the actuator is aligned with axis 1404. The main shaft 1402 can be rotated by actuators in other configurations in other implementations, e.g., as described in various implementations herein.

Main shaft 1402 extends through a central portion 1406 of the handle 1400 and can be coupled to the front of the handle such that it is rotatable about axis 1404. The shaft 1402 is rigidly coupled to a cam 1408. Grip members 1410*a* and 1410*b* are coupled to the central portion 1406 at rotary couplings 1412*a* and 1412*b*, respectively. In some implementations, finger loops 1414*a* and 1414*b* can be attached to the grip members, e.g., to assist securing a user's fingers to the grip members when in use. Any of the implementations described herein can use similar finger loops for their grip members.

Grip members 1410*a* and 1410*b* are coupled to rollers 1418*a* and 1418*b*, respectively, which each rotate about their own lengthwise axes independently of the grip members. The rollers 1418*a* and 1418*b* contact the surface of the cam 1408, and a spring 1416 can be included to bias the rollers 1418*a* and 1418*b* against the cam surface as the cam is rotated. In the example of FIG. 14A, spring 1416 is shown as a helical spring that is coupled between the grip member 1410*a* and the grip member 1410*b*, and the spring is in tension in the position shown in FIG. 14A to bias the group members 1410*a* and 1410*b* against the surface of the cam 1408. In other implementations, other types of springs can be used for spring 1416, and/or the spring 1416 can be placed in different locations of the controller portion 1400. For example, one or more flat springs, leaf springs, or other types of springs can be used, e.g., coupled between the group members 1410*a* and 1410*b* or between each group member and the central portion 1406.

Figure 14B:
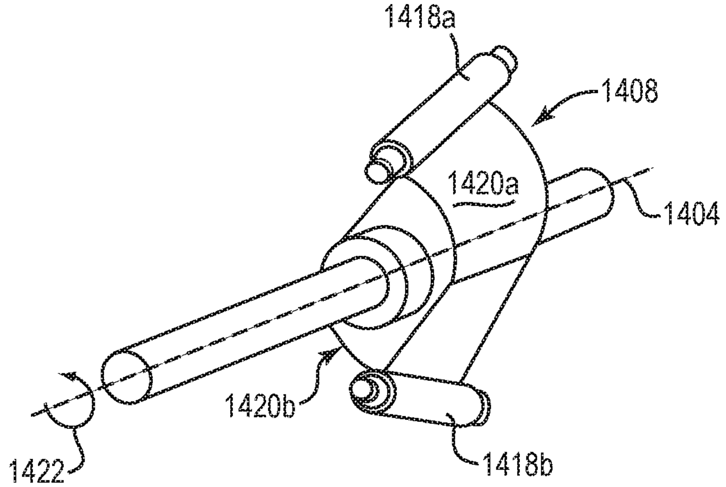

FIG. 14B is a perspective view of an example cam mechanism including cam 1408 and rollers 1418*a* and 1418*b* that can be used in an implementation described in FIG. 14A. Cam 1408 includes an outer surface including portions 1420*a* and 1420*b* having continuously different radii centered on the axis 1404 of rotation. As the cam 1408 rotates, the spring force from spring 1416 biases the rollers 1418 against the surface of the cam 1408, and the rollers 1418*a* and 1418*b* are moved further or closer to the axis

1404 depending on the particular portions of the cam surface that are contacting rollers 1418*a* and 1418*b* (e.g., depending on the angular position of the cam about axis 1404) and depending on the direction of rotation of the cam 1408. For example, if the cam 1408 is rotated in direction 1422 from the position shown, the roller 1418*a* and grip member 1410*a* are allowed to rotate about coupling 1412*a* closer to the axis 1404, since the cam surface 1420*a* curves closer to the axis 1404 as the cam is rotated. Similarly, the roller 1418*b* and grip member 1418*b* are allowed to rotate about coupling 1412*b* closer to the axis 1404 as cam surface 1420*b* curves closer to the axis 1404.

Referring to FIG. 14A, forces can be output in the rotary degrees of freedom of the grip members 1410*a* and 1410*b* by rotating the cam 1408. Handle implementation 1400 therefore does not translate the main shaft 1402 to provide forces to the grip members. In some implementations, a linear actuator and a transmission providing linear forces need not be used, and a rotary actuator can directly drive the main shaft 1402 or can drive the main shaft 1402 via a transmission mechanism.

Some implementations can also provide a second actuator to rotate the handle 1400 about the axis 1404, e.g., rotate the grip members 1410*a* and 1410*b* and the handle body 1406, similarly to actuators 414, 1206, or 1306 in the above implementations. In such examples, cam 1408 can also be rotated with the other portions of the handle 1400. In some implementations, such a second actuator can be positioned on the same axis as the first actuator providing rotation of cam 1408 that provides forces on grip members 1410*a* and 1410*b*. For example, the main shaft 1402 can be driven by the first actuator and positioned within a hollow shaft 1426 that is coupled to the handle body 1406 and to the rotating shaft of the second actuator.

Figure 15:
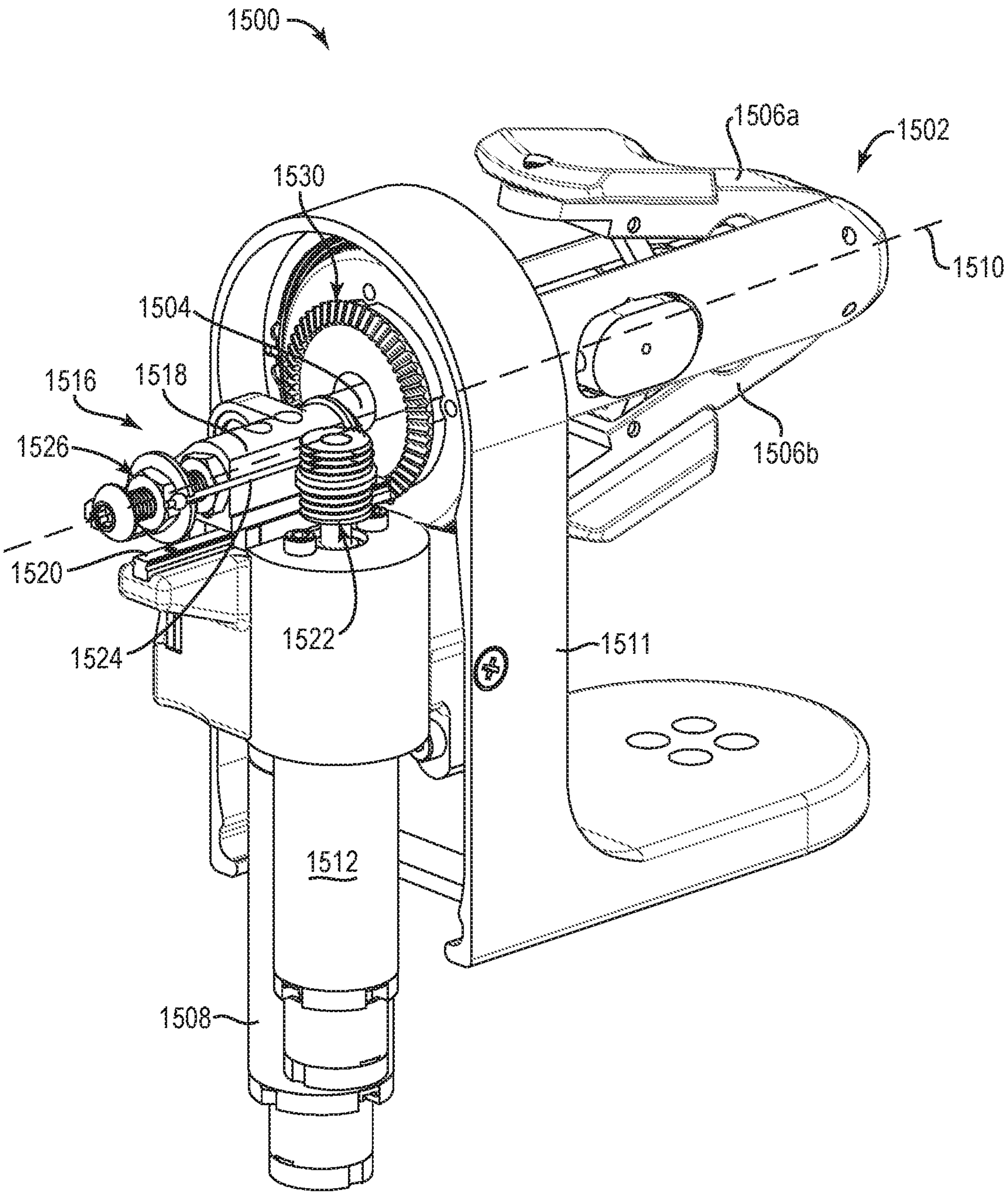
FIG. 15 is a perspective view of an example controller portion including a capstan mechanism to transmit force from an actuator, according to some implementations.

FIG. 15 is a perspective view of an example implementation of a controller portion 1500 including a capstan mechanism to transmit force from an actuator. In some implementations, a master controller handle 1502 of the controller portion 1500 can be similar to the master controller handle 402 described above with respect to FIGS. 4-7B, or a different handle can be used. Handle 1502 and controller portion 1500 can include one or more of the features described for controller portion 400 and other controller implementations described herein.

Controller portion 1500 can include a main shaft 1504 connected to and driving grip members 1506*a* and 1506*b*, similarly to corresponding components in the implementations described above for FIGS. 4-7B. In some implementations, an actuator 1508 (e.g., motor) can be rigidly mounted to the link 1511 and can be used to drive rotation of the handle 1502 similarly to actuator 414 of FIG. 4. As shown in FIG. 15, actuator 1508 can be oriented such that its rotating shaft rotates about an axis that is oriented perpendicular (90 degrees) to the longitudinal axis 1510 of the main shaft 1504, as described in greater detail below. In other implementations, actuator 1508 can be implemented and oriented similarly to actuator 414, e.g., such that its rotating shaft rotates about an axis that is parallel to the axis 1510 and, for example, its shaft is connected to a pulley by a belt to provide rotation of the controller handle 1502 similarly as described above with reference to FIG. 6.

An actuator 1512 can be provided to drive linear motion of the main shaft 1502 along axis 1510. In some implementations, actuator 1512 can be a rotary DC gear motor or other type of rotary actuator. In the implementation of FIG. 15, similarly to actuator 1508, actuator 1512 can be rigidly mounted to the link 1511 and oriented such that its rotating shaft rotates about an axis that is oriented perpendicular (90 degrees) to the axis 1510. Actuator 1512 can be oriented in other ways in other implementations.

Main shaft 1504 can be connected to a capstan mechanism 1516 provided between the main shaft 1504 and the actuator 1512. The capstan mechanism 1516 includes a linear carriage 1518 that is coupled to the main shaft 1504. The main shaft 1504 is decoupled in rotation from the linear carriage 1518 such that the main shaft can be rotated independently of the linear carriage 1518. The linear carriage 1518 can move linearly, e.g., slide, upon a linear rail 1520 that is rigidly coupled to the link 1511. The linear rail 1520 is aligned parallel to the main shaft to allow linear motion of the linear carriage 1518.

The capstan mechanism 1516 also includes a capstan drum 1522 having helical grooves, and which is rigidly coupled to the rotating shaft of actuator 1512. The capstan drum 1522 is coupled to the linear carriage 1518 by a cable 1524. For example, cable 1524 can be a high-stiffness metal cable in some implementations. A first end of cable 1524 can be attached to a groove (or via some other fastening mechanism) at a first portion of the linear carriage 1518, e.g., the end or a portion of the carriage 1518 that is closest to the handle 1502. The cable 1524 is wrapped a number of times around the capstan drum 1522, e.g., within the grooves of the capstan drum. The second end of the cable 1524 can be attached at a second portion of the linear carriage 1518, e.g., the end or a portion of the carriage 1518 that is further from the handle 1502 than the first portion of the carriage. In the example shown, the second end of the cable 1524 is attached to a nut 1526 on a threaded screw coupled at the second portion of the linear carriage 1518, where the nut 1526 and second end of the cable 1524 can be moved closer or further from the carriage 1518 along the screw to adjust the tension in the cable. Other mechanisms can be used to tension the cable in other implementations.

The driven rotation of the shaft of the actuator 1512 directly drives the constrained linear motion of the linear carriage 1518 and the main shaft 1504 via the cable 1524, thus causing forces on the grip members 1506*a* and 1506*b* to bias them toward open and closed positions in accordance with the linear motion of the main shaft 1504, similarly as described in other implementations herein. In some implementations, a benefit of the capstan mechanism is that it can provide a high-stiffness, low-backlash transmission for active forces on the grip members 1506*a* and 1506*b* and handle 1502 while allowing the actuator(s) to be mounted 90-degrees to the main shaft 1504. This can reduce the packaging size, mass, and inertia of the controller portion 1500.

Actuators 1508 and/or 1512 can be any of a variety of types of actuators similarly as described herein for the other implementations. For example, these actuators can be active actuators, e.g., motors (e.g., DC motors), voice coils, or other types of active actuators. Passive actuators (e.g., springs, brakes, etc.) can be used in some implementations to provide resistance in particular directions of the grip members, in rotation of the handle 1500 about axis 1510, etc.

Similarly as described in the other implementations herein, one or more sensors can be coupled to the handle 1502 and/or other components of the controller portion 1500 and can detect the positions of the grip members 1506*a* and 1506*b*. For example, in some implementations, a rotary encoder can be included in the housing of actuator 1512 to detect rotation of the shaft of actuator 1512. In some implementations, a linear sensor can be coupled to the link

Figure 16A:
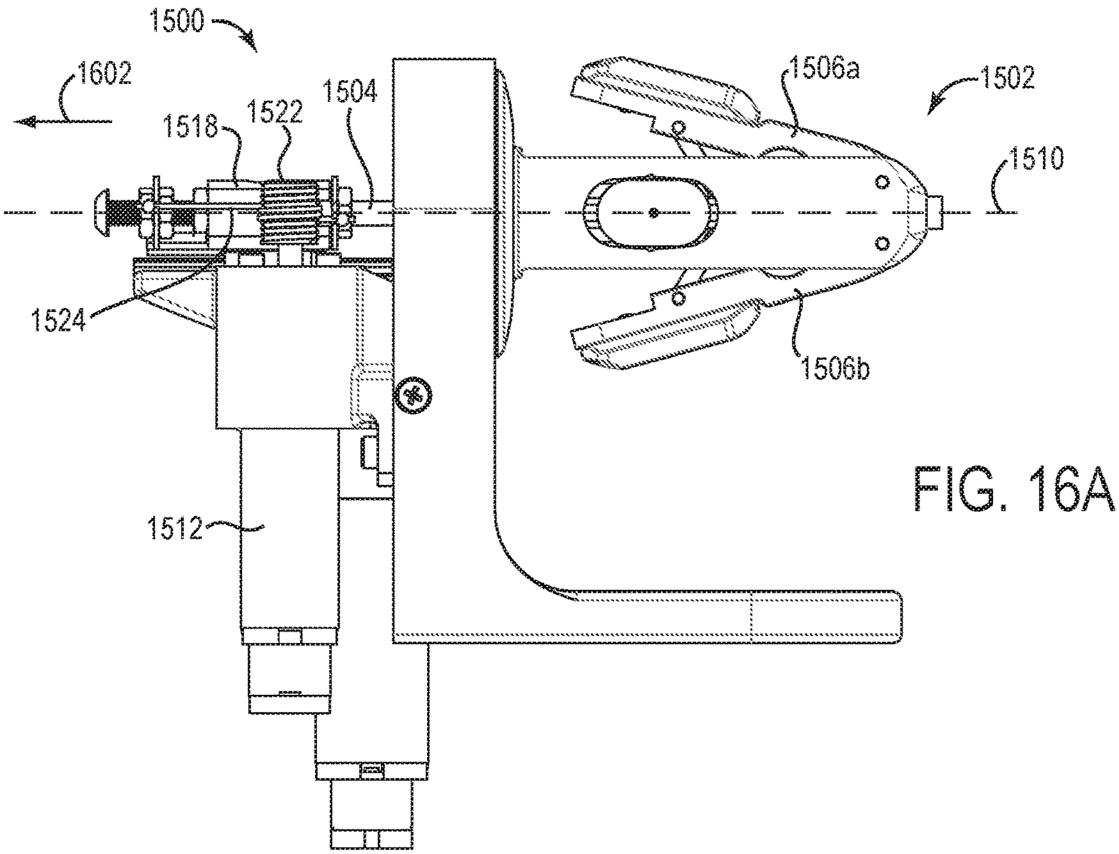
FIGS. 16A and 16B are side elevational views of the controller portion of FIG. 15, according to some implementations.
Figure 16B:
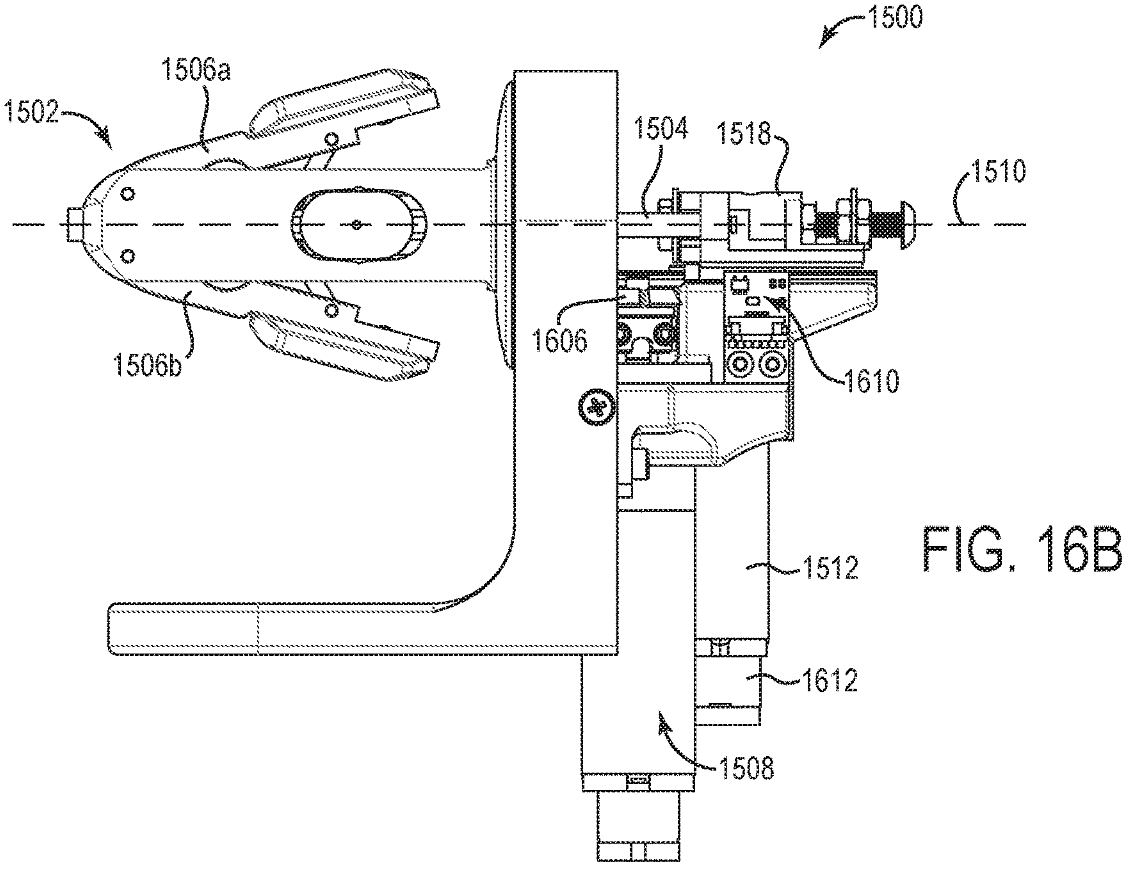

1511 to sense linear motion of the linear carriage 1518 (e.g., secondary sensor 1610 of FIG. 16B). Similarly, one or more sensors can be coupled to one or more components of the controller portion 1500 and can detect the roll position of the handle 1502 about axis 1510. For example, in some implementations, a rotary encoder can be included in the housing for actuator 1508 to detect rotation of the shaft of actuator 1508. The sensors can send signals describing sensed positions or motion to one or more control circuits of the teleoperated system 100. In some modes or implementations, the control circuits can provide control signals to the slave manipulator device 104. The sensors can be any of a variety of types of sensors, e.g., a magnetic sensor (e.g., magnetic incremental linear position sensor, Hall Effect sensor, etc.), optical sensor, encoder, resistance sensor, etc.

In some implementations, transmission mechanisms other than the capstan mechanism 1516 can be used. For example, a rack and pinion mechanism can be used, where a pinion gear can be used instead of the capstan drum 1522 and a rack gear can be provided on the linear carriage 1518 to engage the pinion gear. In another example, a drive wheel can be used instead of the capstan drum 1522, e.g., using friction to couple or engage the drive wheel to a linear surface of the linear carriage 1518 and move or force the carriage linearly when the drive wheel is rotated.

FIGS. 16A and 16B are side elevational views of the controller portion 1500 of FIG. 15, where FIG. 16A shows one side of the controller portion 1500 and FIG. 16B shows the opposite side.

In FIG. 16A, the grip members 1506*a* and 1506*b* are in an open position, e.g., the grip members are at a position in which their disconnected ends are furthest away from each other as allowed by the coupled mechanism. To cause this position from a position in which the links are closer to each other, the actuator 1512 causes a force in the direction 1602 away from the grip members 1506*a* and 1506*b*. For example, the capstan drum 1522 coupled to the actuator 1512 can be rotated in a rotational direction to move cable 1524 and cause forces on linear carriage 1518 that cause it to move in the direction 1602. Linear carriage 1518 is coupled to the main shaft 1504 and causes the main shaft 1504 to move in the same direction, thus transmitting force to the grip members 1506*a* and 1506*b* in directions toward their open positions. Similarly, the capstan drum 1522 can be rotated in the opposite rotational direction to move cable 1524 in the opposite direction and cause forces on linear carriage 1518 in the direction opposite to direction 1602, causing the main shaft 1504 to move and transmit force to the grip members 1506*a* and 1506*b* in directions toward their closed positions.

In FIG. 16B, actuator 1508 has a rotary shaft that is rigidly coupled to a roll bevel pinion 1606. The roll bevel pinion 1606 includes a number of teeth that engage a number of grooves/teeth of a roll gear (ring) 1530 (shown in FIG. 15). Rotation of the roll bevel pinion 1606 about the axis of rotation of the actuator shaft causes rotation of the roll bevel pinion 1606 about axis 1510 of the controller portion 1500. This causes rotational forces to the handle 1502, e.g., can cause the handle 1502 to rotate about axis 1510. The roll bevel pinion 1606 and roll gear 1530 thus can provide rotational forces to the handle 1502 similarly to the actuator 414, belt 620, and pulley 622 described with reference to FIGS. 4-6.

A sensor 1610 can be provided to sense linear motion of the linear carriage 1518 and main shaft 1504 along the axis 1510. In some implementations, sensor 1610 can be included in addition to a sensor (e.g., rotary encoder) 1612 that can sense the rotation of the shaft of actuator 1512 and capstan drum 1522 to thereby sense linear motion of the main shaft 1504.

Figure 17A:
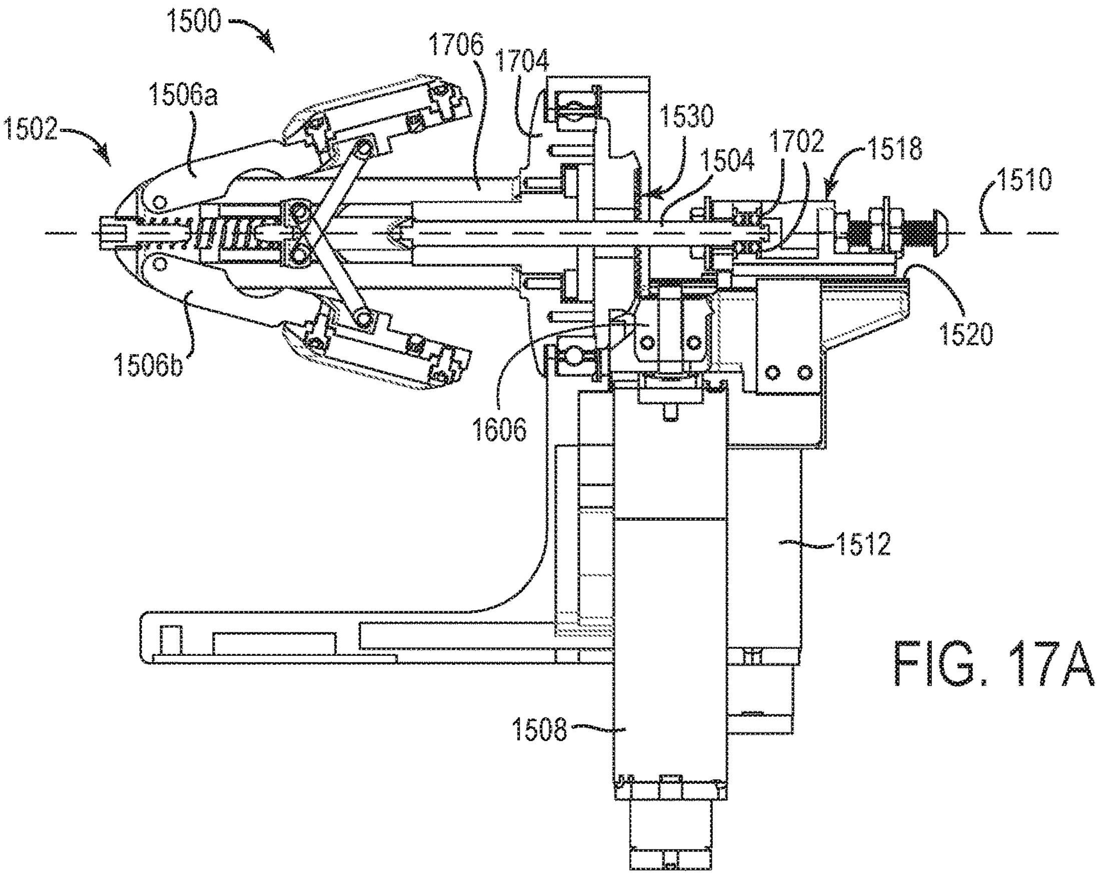
FIGS. 17A and 17B are side elevational, cross-sectional views of the controller portion of FIG. 15, according to some implementations.
Figure 17B:
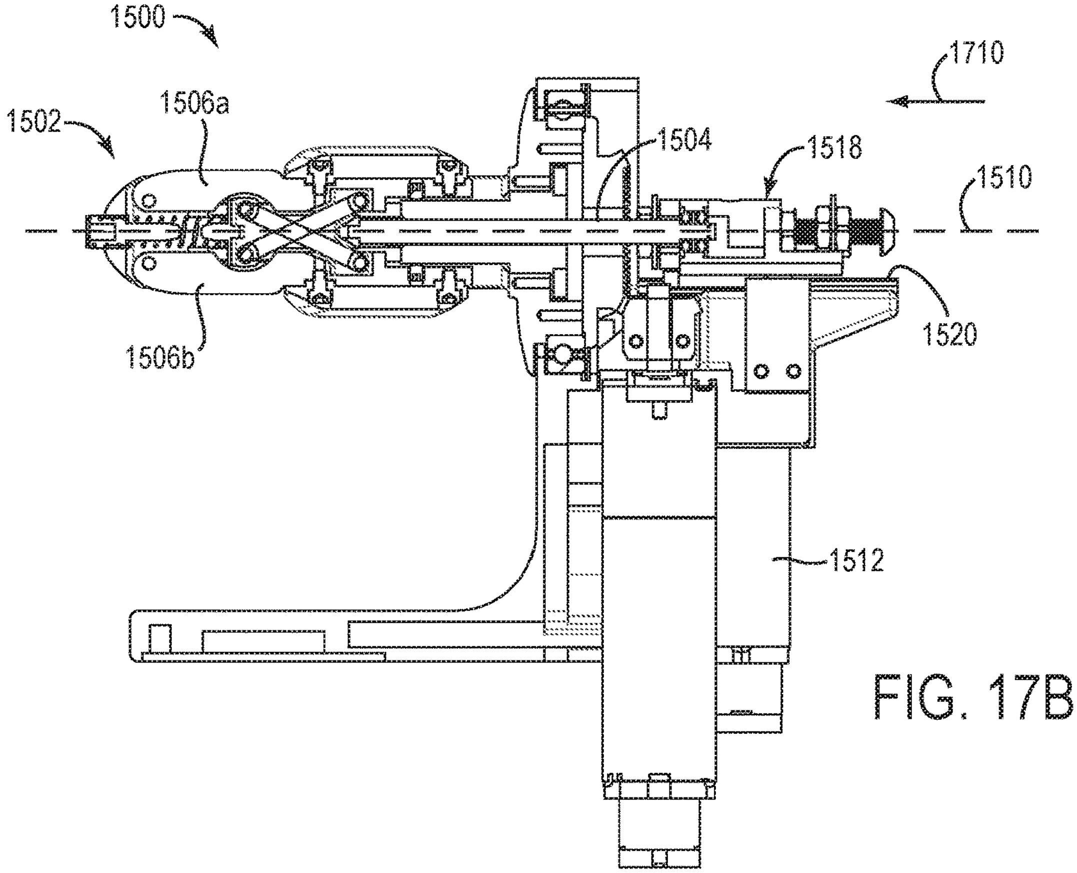

FIGS. 17A and 17B are side elevational, cross-sectional views of the interior of controller portion 1500 of FIG. 15 and show different positions of the grip members 1506*a* and 1506*b*.

FIG. 17A shows an open position of the grip members 1506*a* and 1506*b*. Main shaft 1504 is coupled to linear carriage 1518 such that when linear carriage 1518 moves linearly parallel to axis 1510, the main shaft 1504 is moved correspondingly along axis 1510. The main shaft 1504 is decoupled in rotation from the linear carriage 1518 such that the main shaft can be rotated independently of the linear carriage 1518. For example, one or more couplings 1702 (e.g., bearings) can couple the main shaft 1504 to the linear carriage 1518 along the linear directions of axis 1510, and can decouple the main shaft 1504 and linear carriage 1518 in the rotational directions around axis 1510 so that the main shaft 1504 can continuously rotate independently of the linear carriage 1518.

Roll bevel pinion 1606 is coupled to the rotating shaft of actuator 1508. The roll bevel pinion 1606 is engaged with roll gear 1530 to cause rotary forces about axis 1510 to the handle 1502. For example, the roll gear 1530 can be rigidly coupled to a member including a plate 1704 (similar to plate 430 shown in FIG. 4), where the member and plate are rigidly coupled to the central portion 1706 of the handle 1502 and rotate with the handle 1502. Thus, the roll gear 1530 can transmit rotational forces to the handle 1502 around axis 1510.

FIG. 17B shows a closed position of the grip members 1506*a* and 1506*b*. Linear carriage 1518 has been moved by actuator 1512 in a direction 1710 to linearly move the main shaft 1504 along the axis 1510 toward the handle 1502. In accordance with the movement of the main shaft 1504, the grip members 1506*a* and 1506*b* have been moved to a closed position by the linkages in handle 1502, which can be similar and operate similarly to the linkages shown in handle 402 in FIGS. 7A and 7B.

Other components and alternative implementations described herein for other implementations can also be used in the controller portion 1500.

Figure 18:
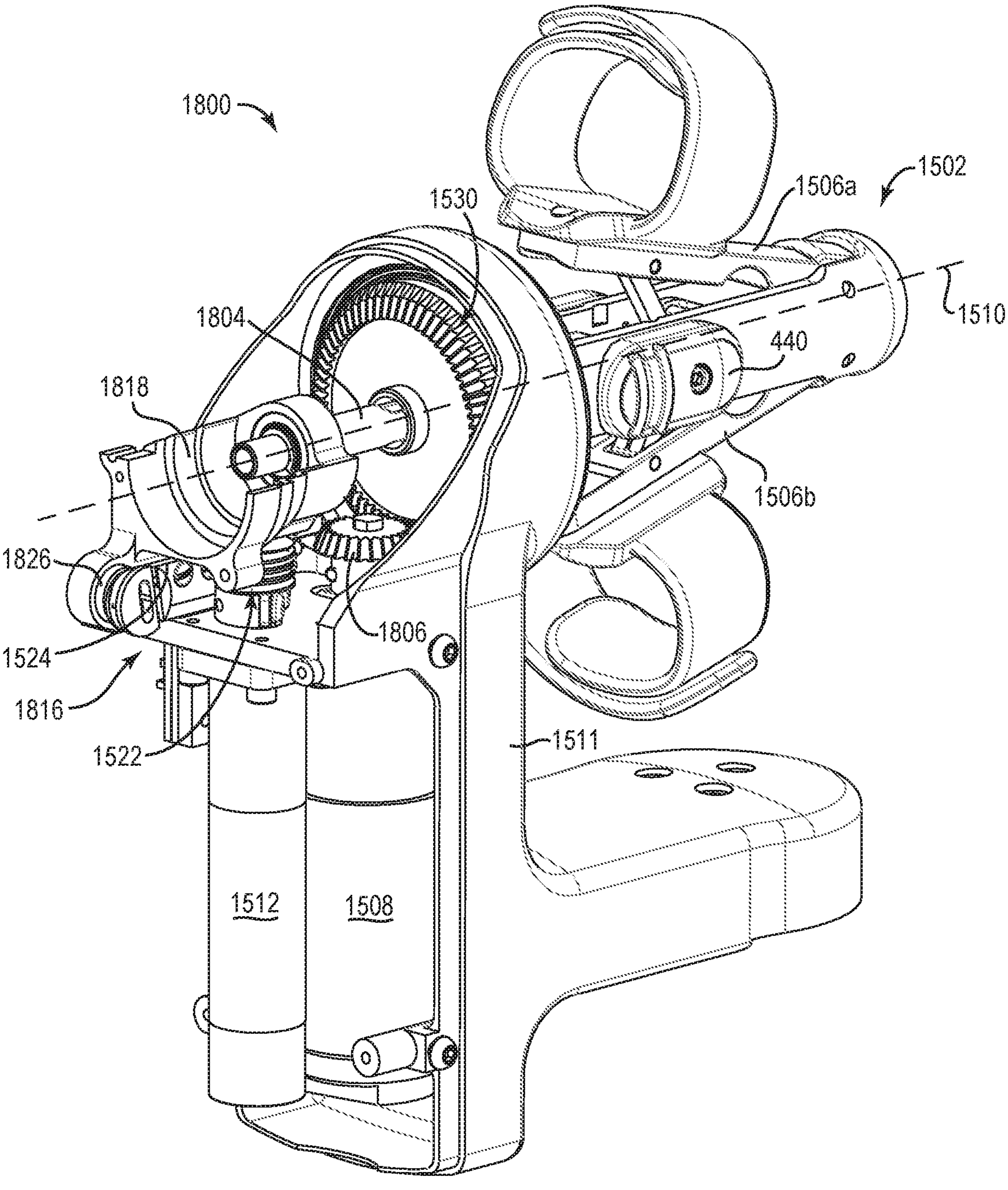
FIG. 18 is a perspective view of another example controller portion including a capstan mechanism to transmit force from an actuator, according to some implementations.

FIG. 18 is a perspective view of an example implementation of a controller portion 1800 including a capstan mechanism to transmit force from an actuator. Controller portion 1800 can include several components which operate similarly to corresponding components of the controller portion 1500, some of which are labelled in FIGS. 18-20B with the same reference numbers as shown in FIGS. 15-17B. Some differently-numbered components can also operate similarly to corresponding components of the controller portion 1500 described above.

Controller portion 1800 can include a main shaft 1804 connected to and driving grip members 1506*a* and 1506*b*, similarly to corresponding components in the implementations described above for FIGS. 4-7B and FIG. 15. In some implementations, actuator 1508 (e.g., motor) can be rigidly mounted to the link 1511 and can be used to drive rotation of the handle 1502. As shown in the implementation of FIG. 18, actuator 1508 can be oriented such that its rotating shaft rotates gear 1806 about an axis that is oriented perpendicular (90 degrees) to the longitudinal axis 1510 of the main shaft 1504, to engage roll gear (ring) 1530 and cause roll gear 1530 to rotate.

In the implementation of FIG. 18, actuator 1512 can be rigidly mounted to the link 1511 and is positioned such that the axis of rotation of the shaft of actuator 1512 is approximately perpendicular to longitudinal axis 1510. In some implementations, the axis of actuator 1512 can be positioned close to the linear rail 1904 (see FIG. 19B) to reduce force and friction on the rail 1904. In some implementations, the axis of rotation of the shaft of actuator 1512 extends such that it is positioned closer to axis 1510 (and/or closer to the center of the controller portion 1800) than the rotary axis of actuator 1512 shown in FIG. 15. Actuator 1512 in the configuration of FIG. 18 may thus provide less inertia to the rotation of the handle 1502 than in the configuration of FIG. 15.

Main shaft 1804 is connected to a capstan mechanism 1816 provided between the main shaft 1804 and the actuator 1512. The capstan mechanism 1816 includes a linear carriage 1818 that is coupled to the main shaft 1804 and which can move linearly, e.g., slide, upon a linear rail (see FIG. 19B) that is rigidly coupled to the link 1511, similarly to linear carriage 1518.

The capstan drum 1522 is coupled to the linear carriage 1818 by cable 1524 that is wrapped around capstan drum 1522 as described above. The first end of cable 1524 can be attached to a first portion of the linear carriage 1818, e.g., the end or portion of the carriage 1818 that is closest to the handle 1502. The second end of the cable 1524 can be attached at a second portion of the linear carriage 1818, e.g., the end or portion of the carriage 1818 that is further from the handle 1502 than the first portion of the carriage 1818. In the example shown, the second end of the cable 1524 is attached to a disc 1826 coupled at the second portion of the linear carriage 1518, where the disc 1826 can be rotated to move the second end of the cable 1524 closer or further from the capstan drum 1522 to adjust the tension in the cable.

The driven rotation of the shaft of the actuator 1512 directly drives the constrained linear motion of the linear carriage 1818 and the main shaft 1804 via the cable 1524, thus causing forces on the grip members 1506*a* and 1506*b* to bias them toward open and closed positions in accordance with the linear motion of the main shaft 1504, similarly as described in other implementations herein.

Actuator 1508 has a rotary shaft that is rigidly coupled to a roll bevel pinion 1806. The roll bevel pinion 1806 includes a number of teeth that engage a number of grooves/teeth of a roll gear 1530. Rotation of the roll bevel pinion 1806 about the axis of rotation of the shaft of actuator 1508 causes rotation of the roll bevel pinion 1806 about axis 1510. This causes rotational forces to the handle 1502 similarly as described above.

Figure 19A:
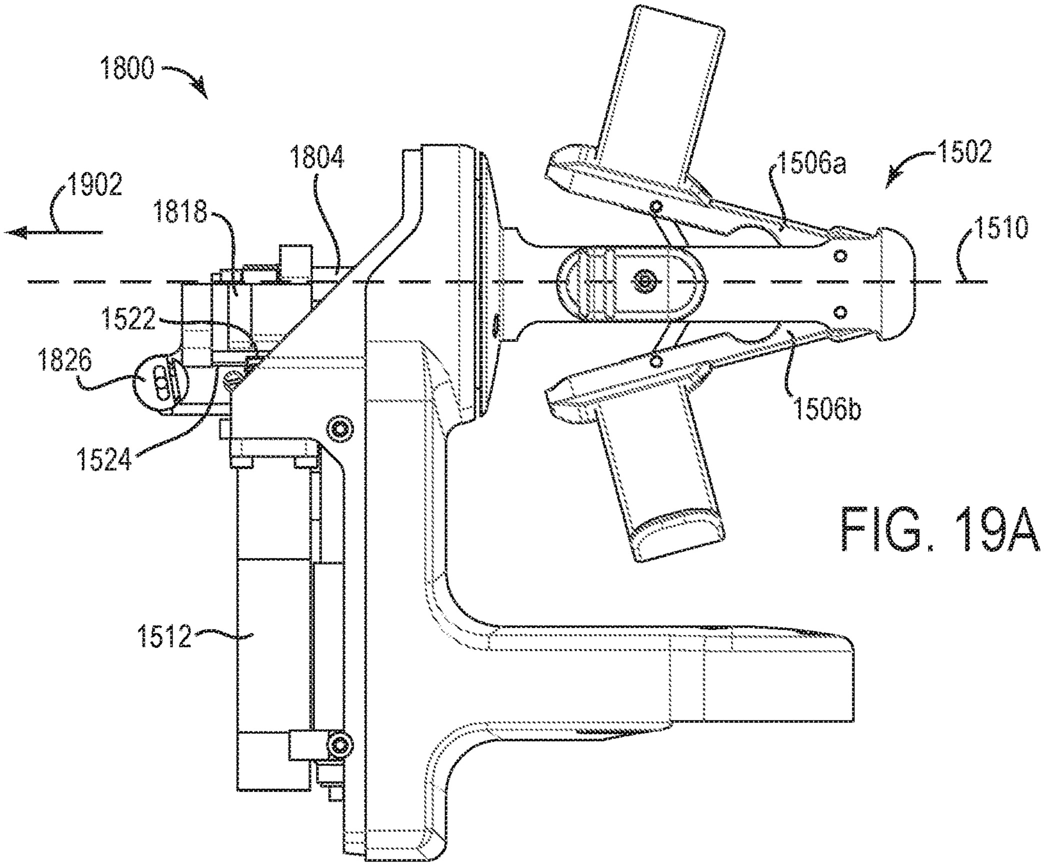
FIGS. 19A and 19B are side elevational views of the controller portion of FIG. 18, according to some implementations.
Figure 19B:
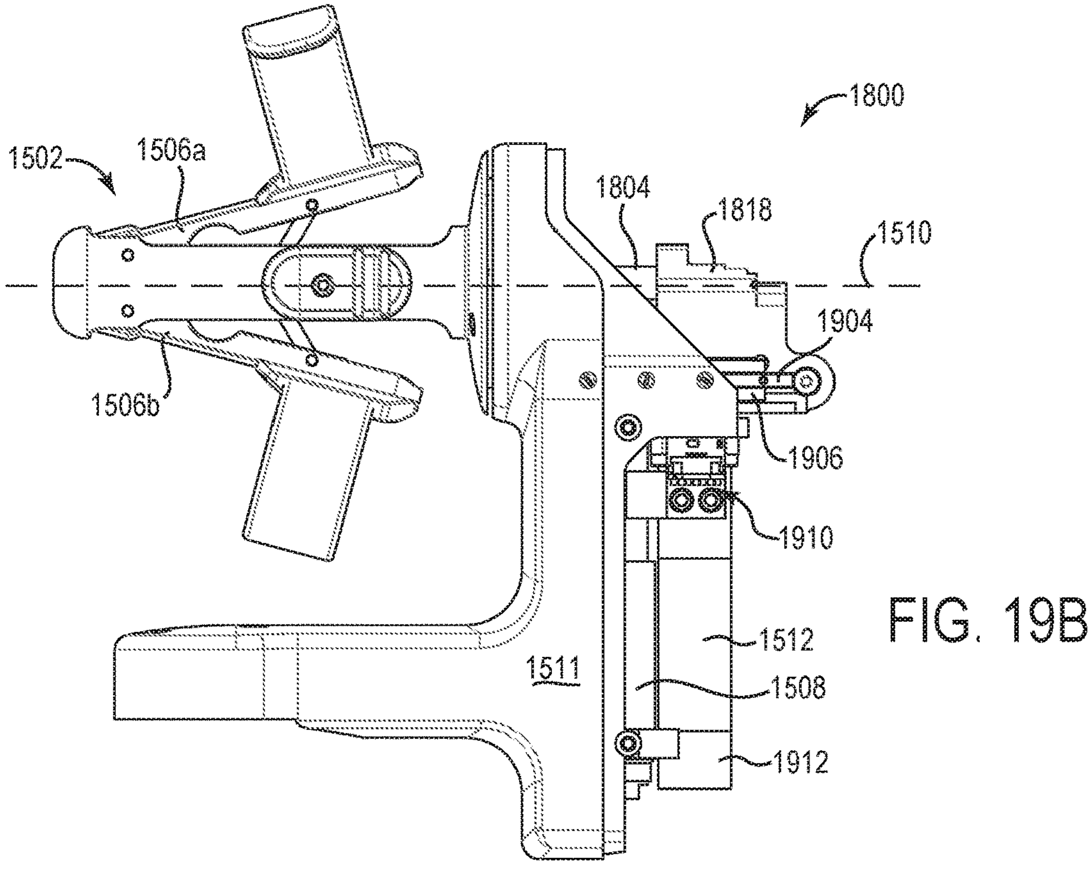

FIGS. 19A and 19B are side elevational views of the controller portion 1800 of FIG. 18, where FIG. 19A shows one side of the controller portion 1800 and FIG. 19B shows the opposite side. FIGS. 19A and 19B are similar to FIGS. 16A and 16B and some corresponding components are numbered the same.

In FIG. 19A, the grip members 1506*a* and 1506*b* are in an open position, e.g., the grip members are at a position in which their disconnected ends are furthest away from each other as allowed by the coupled mechanism. To cause this position from a position in which the links are closer to each other, the actuator 1512 causes a force on shaft 1804 in the direction 1902 away from the grip members 1506*a* and 1506*b*. For example, the capstan drum 1522 coupled to the actuator 1512 can be rotated in a rotational direction to move cable 1524 and cause forces on linear carriage 1818 that cause it to move in the direction 1902. Linear carriage 1818 is coupled to the main shaft 1804 and causes the main shaft 1804 to move in the same direction, thus transmitting force to the grip members 1506*a* and 1506*b* in directions toward their open positions. Similarly, the capstan drum 1522 can be rotated in the opposite rotational direction to move cable 1524 in the opposite direction and cause forces on linear carriage 1818 in the direction opposite to direction 1902, causing the main shaft 1804 to move and transmit force to the grip members 1506*a* and 1506*b* in directions toward their closed positions.

In FIG. 19B, the grip members 1506*a* and 1506*b* are in an open position. Guide rail 1904 is coupled to the link 1511, and the linear carriage 1818 includes a groove piece 1906 that slides along the guide rail 1904. The components operate similarly as corresponding components in implementations described above.

A linear sensor 1910 can be provided to sense linear motion of the linear carriage 1818 and main shaft 1804 along the axis 1510. In some implementations, sensor 1910 can be included in addition to a sensor (e.g., rotary encoder) 1912 that can sense the rotation of the shaft of actuator 1512 and capstan drum 1522 to thereby sense the linear motion of the main shaft 1804.

Figure 20A:
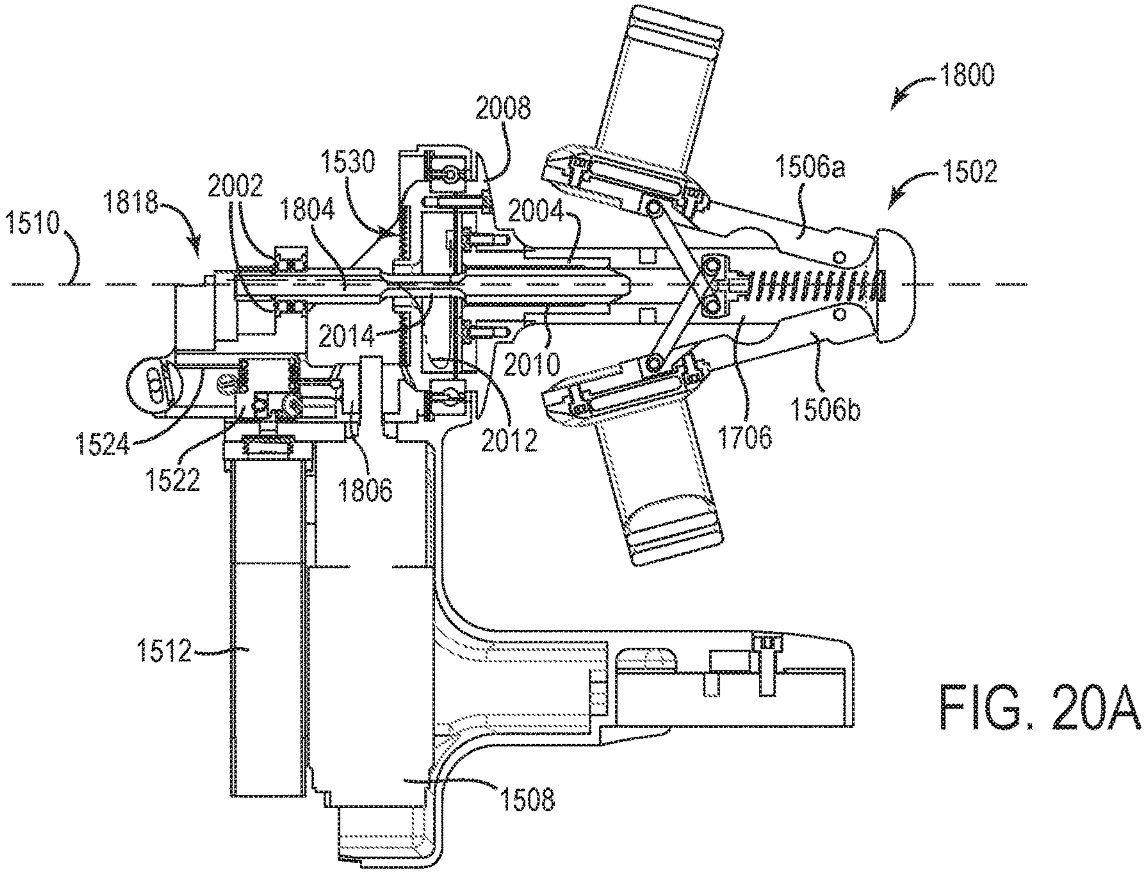
FIGS. 20A and 20B are side elevational, cross-sectional views of the controller portion of FIG. 18, according to some implementations.
Figure 20B:
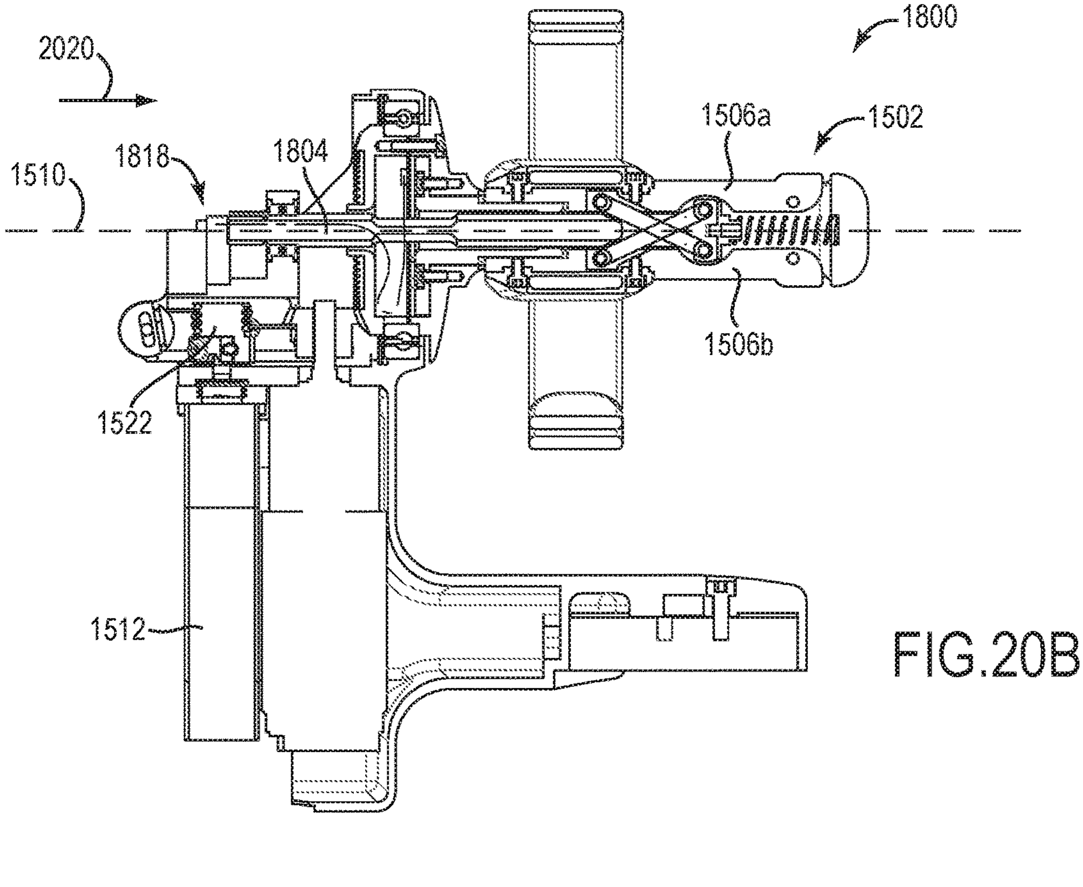

FIGS. 20A and 20B are side elevational, cross-sectional views of the interior of controller portion 1800 of FIG. 18 and show different positions of the grip members 1506*a* and 1506*b*.

FIG. 20A shows an open position of the grip members 1506*a* and 1506*b*. Main shaft 1804 is coupled to linear carriage 1818 such that when linear carriage 1818 moves linearly parallel to axis 1510, the main shaft 1804 is moved correspondingly along axis 1510. The main shaft 1804 is decoupled in rotation from the linear carriage 1818 such that the main shaft can be rotated independently of the linear carriage 1818. For example, one or more couplings 2002 (e.g., bearings) can couple the main shaft 1804 to the linear carriage 1818 along the linear directions of axis 1510, and can decouple the main shaft 1804 and linear carriage 1818 in the rotational directions around axis 1510.

Roll bevel pinion 1806 is engaged with roll gear 1530 to cause rotary forces about axis 1510 to the handle 1502. For example, the roll gear 1530 can be rigidly coupled to a member/plate 2008 (similar to plate 1704 and 430), where the member/plate is rigidly coupled to, or is an extension of, the central portion 1706 of the handle 1502 and rotates with the handle 1502. Thus, the roll gear 1530 can transmit rotational forces to the handle 1502 around axis 1510.

In this example implementation, a linear bushing 2004 is positioned around the main shaft 1804 and extends from the member 2008 toward the handle 1502. Linear bushing 2004 guides the main shaft 1804 such that it maintains its position along axis 1510. The bushing 2004 can provide a clearance or gap 2010 at a portion of the length of the bushing, e.g., a portion between the member/plate 2008 and a front portion of the bushing 2004 that contacts the main shaft 1804. The gap 2010 allows some lateral movement, e.g., angular tilt or play, of the rear portion of the shaft 1804 at linear carriage 1818, e.g., movement having component directions perpendicular to the axis 1510. This allowance for play can reduce binding of the main shaft 1804 against the bushing 2004, e.g., if there is misalignment of the shaft 1804 relative to axis 1510. In some examples, the bushing 2004 can be made of slippery material, e.g., plastic.

In some examples, such as the implementation shown, the main shaft 1804 can be made hollow to allow one or more components to be routed through the main shaft. For example, one or more cables can be routed through main shaft 1804. In some examples, cables that connect a button 440 (see FIG. 18) to a controller positioned at the rear of the controller portion 1800 can be routed through the main shaft 1804. In some implementations, the main shaft 1804 can include one or more notches or apertures that allow components such as cables to be routed within the housing of the controller portion 1800. For example, in FIG. 20A, dashed line 2012 represents a cable that can be routed from the rear portion of the shaft near carriage 1818, through the hollow main shaft 1804, and out of an aperture 2014 of the shaft 1804 into an interior space, in which the cable is coupled to an electrical contact that in turn electrically connects to the buttons 440. For example, the cable 2012 can be routed with slack or a loop as shown to allow the main shaft 1804 to be moved forward and back without over-stretching the cable.

FIG. 20B shows a closed position of the grip members 1506*a* and 1506*b*. Linear carriage 1818 has been moved by actuator 1512 in a direction 2020 to linearly move the main shaft 1504 along the axis 1510 toward the handle 1502. In accordance with the movement of the main shaft 1804, the grip members 1506*a* and 1506*b* have been moved to a closed position by the linkages in handle 1502, which can be similar to and operate similarly as described above.

Other components and alternative implementations described herein for other implementations can also be used in the controller portion 1800.

Figure 21:
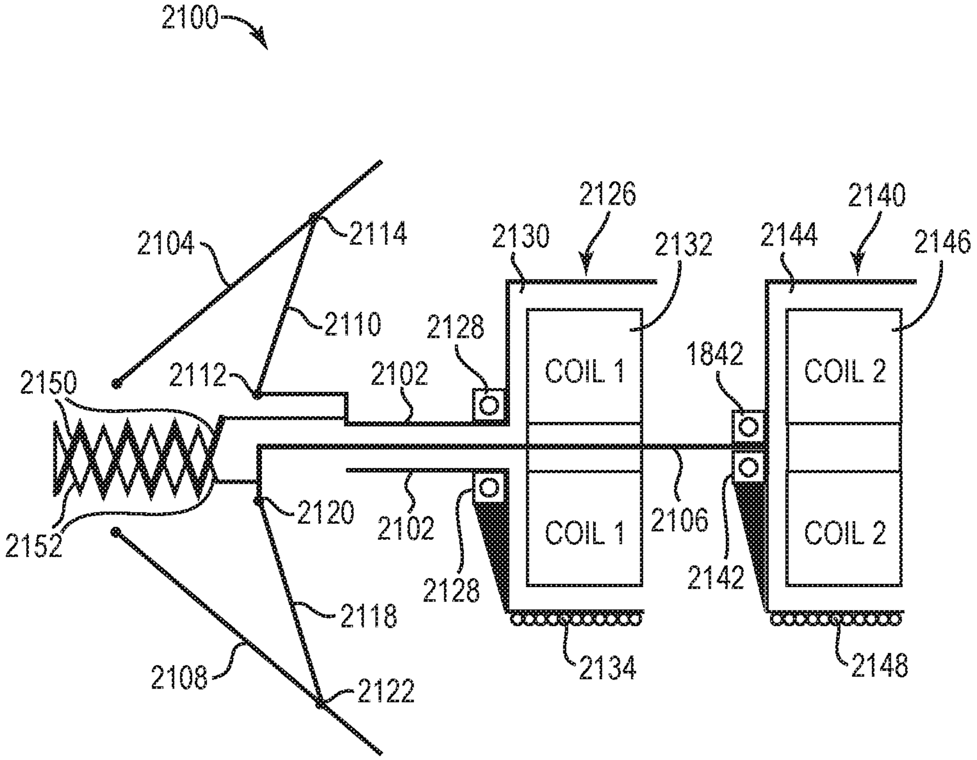
FIG. 21 is a diagrammatic illustration of an example implementation of a controller system including multiple independently-actuated grips, according to some implementations.

FIG. 21 is a diagrammatic illustration of an example implementation of a controller system 2100 including multiple independently-actuated grips. FIG. 21 is provided in an abstracted or schematic illustration. The mechanisms can be similar in implementation as in other example controller portions described herein.

Controller system 2100 includes a first shaft 2102 coupled to a first grip member 2104, and a second shaft 2106 coupled to a second grip member 2108. Grip members 2104 and 2108 can be similar to the grip members 406*a*, 406*b*, etc. described for other implementations herein. For example, the grip members 2104 and 2108 can each be rotated in a rotary degree of freedom and can be coupled to their respective shafts by an intermediate linkage. In some implementations, each grip member 2104 and 2108 can be rotated in its degree of freedom independently of the other grip member 2108 and 2104, respectively. In this example, the first shaft 2102 is coupled to an intermediate link 2110 by a rotational coupling 2112, and the intermediate link 2110 is coupled to grip member 2104 at its other end by a rotational coupling 2114. Similarly, the second shaft 2106 is coupled to an intermediate link 2118 by a rotational coupling 2120, and the intermediate link 2118 is coupled to grip member 2108 at its other end by a rotational coupling 2122.

First shaft 2102 is coupled to a first actuator 2126 at the shaft's end opposite to the intermediate link 2110. For example, the first shaft 2102 can be coupled to the first actuator 2126 by a rotary coupling 2128 that couples the first shaft 2102 to the first actuator 2126 in the linear degree of freedom along the shaft, and decouples in rotation the first shaft 2102 from the first actuator 2126 such that the first shaft can be rotated independently of the first actuator 2126. In some examples, first actuator 2126 can be a linear actuator outputting a linear force along the axis of first shaft 2102, e.g., a voice coil or other type of actuator. For example, a voice coil actuator 2126 can include a magnet 2130 and a coil 2132. In this example, the magnet 2128 is grounded to a linear rail 2134 that constrains the motion of the magnet 2128 along a linear axis of the first shaft 2102. Actuator 2126 can be similar to actuator 411 of FIGS. 4-7B. In some implementations, actuator 2126 can be a different type of actuator, e.g., a motor (e.g., rotary actuator).

In this example, second shaft 2106 extends through a hollow interior portion of the first shaft 2102 and extends through the first actuator 2126. Second shaft 2106 is coupled to a second actuator 2140 at the shaft's end opposite to the intermediate link 2118. For example, the second shaft 2106 can be coupled to the second actuator 2140 by a rotational coupling 2142 that couples the second shaft 2106 to the second actuator 2140 in the linear degree of freedom along the shaft, where the second shaft 2106 is decoupled in rotation from the second actuator 2140 such that the second shaft can be rotated independently of the second actuator 2140. In some examples, second actuator 2140 can be a linear actuator outputting a linear force along the axis of second shaft 2106, e.g., similarly to first actuator 2126 and first shaft 2102. Second actuator 2140 can be a voice coil or other type of actuator similarly to the first actuator 2126. For example, a voice coil actuator 2140 can include a magnet 2144 and a coil 2146. In this example, the magnet 2144 is grounded to a linear rail 2148 that constrains the motion of the magnet 2144 along a linear (e.g., longitudinal) axis of the second shaft 2106.

A first spring 2150 is coupled between the first shaft 2102 and a handle body or central portion of the controller, e.g., similarly to spring 708 shown in FIGS. 7A-7B. A second spring 2152 is coupled between the second shaft 2106 and the handle body of the controller. In some implementations, the second spring 2152 can extend within the helical diameter of the first spring 2150, such that the first and second springs are concentric along most of their lengths, e.g., centered along the same axis that is about parallel to the first and second shafts 2102 and 2106. In some other examples, the first spring 2150 can extend within the helical diameter of the second spring 2152, or the first and second springs can be approximately parallel to each other and not concentric.

In operation, the controller system 2100 can provide forces independently in the degrees of freedom of the grip members 2104 and 2108. For example, first actuator 2126 can output a linear force on first shaft 2102, and the force can be output on intermediate link 2110, which provides the force as a rotational force in the degree of freedom of grip member 2104. Second actuator 2140 can output a linear force on second shaft 2106 independently of the force output of the first actuator on first shaft 2102. The force on the second shaft can be output on intermediate link 2118, which provides the force as a rotational force in the degree of freedom of grip member 2108. In some implementations, a handle portion including the grip members 2104 and 2108, first and second shafts 2102 and 2106, and springs 2150 and 2152 can be rotated in unison in a rotary degree of freedom about the axis defined by the first and second shafts 2102 and 2106. For example, a third actuator (not shown) can transmit forces to this handle portion in this rotary degree of freedom, similarly to actuator 414 of FIGS. 4-6.

In some implementations, other components can be used in system 2100. For example, one or both of first actuator 2126 and second actuator 2140 can be replaced by a rotary actuator and a transmission mechanism for converting the rotary force output by the actuator to a linear force output on the first shaft 2102 and/or second shaft 2106 (e.g., using an implementation as shown in FIG. 12 and/or FIG. 13).

One or more features described herein can be used with other types of master controllers. For example, ungrounded master controllers can be used, which are free to move in space and disconnected from ground. In some examples, one or more handles similar to handle 402 and/or grip members 406*a* and 406*b* can be coupled to a mechanism worn on a user's hand and which is ungrounded, allowing the user to move grips freely in space. In some examples, the positions of the grips can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Some examples of ungrounded master controllers are described in U.S. Pat. Nos. 8,543,240 and 8,521,331, both incorporated herein by reference. The detection of user touch described herein can be used with ungrounded master controllers. For example, vibration can be applied to a handle (e.g., grip) by one or more actuators coupled to the handle, and this vibration can be sensed similarly as described herein to determine if the handle is contacted or grasped by the user.

Figure 22:
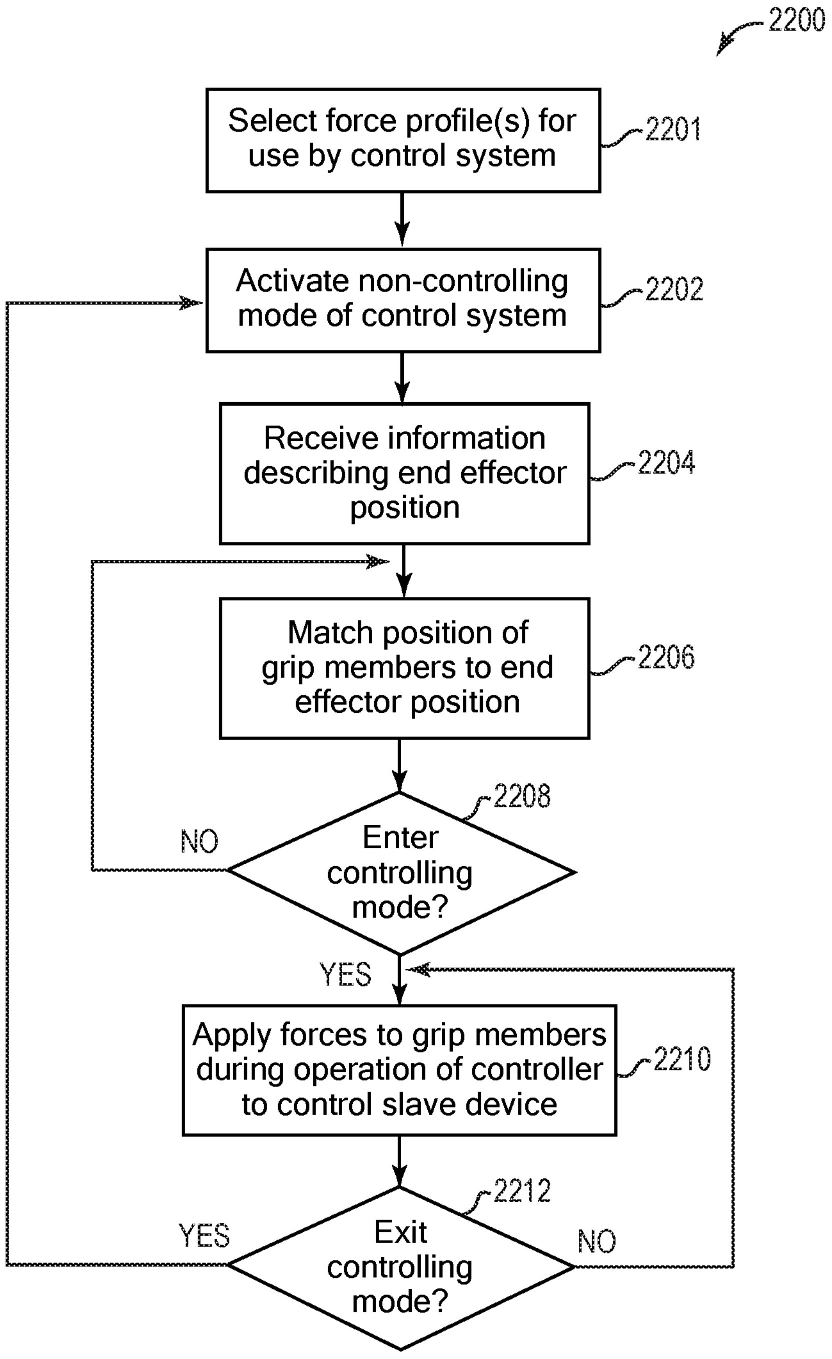
FIG. 22 is a flow diagram illustrating an example method to provide forces on a controller, according to some implementations.

FIG. 22 is a flow diagram illustrating an example method 2200 to provide forces on a controller. Method 2200 can, for example, be used with an example teleoperated system or other control system in which the controller is a master controller that controls a slave device. For example, in some implementations, the controller is a component of a workstation, e.g., master control workstation 102 of FIG. 1, and method 2200 can be performed by a control circuit component of the master control workstation 102. In some examples, the control circuit can include one or more processors, e.g., microprocessors or other control circuits, some examples of which are described below with reference to FIG. 23. A single master controller is referred to in method 2200 for explanatory purposes. The master controller can be, for example, any of the controller implementations described herein, and/or one of master controller 210 or 212 of FIG. 2. Multiple master controllers can be similarly processed as described in method 2200, e.g., each master controller 210 and 212 of FIG. 2. Other implementations can use a controller having one or more features described herein with other types of systems, e.g., non-teleoperated systems, a virtual environment (e.g., medical simulation) having no physical slave device and/or no physical subject interacting with a physical slave device, etc.

In block 2201, some implementations can select one or more particular force profiles for use by the control system, which designate particular forces to be output on the controller (e.g., to grip members of the controller based on grip member position). For example, the selection of force profiles can be based on the type of end effector currently controlled by the master controller. In some examples, multiple different force profiles can be available as described with reference to the examples of FIG. 10, and each of these force profiles can be associated with one or more types of end effectors usable with the slave device. The type of end effector currently connected to the slave device can be determined (e.g., via identifying information automatically read by the slave device or input manually by an operator) and a force profile associated with that type can be selected for use from storage (e.g., connected memory or storage device). The types of end effectors can be organized in various ways in different implementations. For example, types can be based on specific models of end effectors, where each difference in physical dimensions and/or operation of an end effector is defined as a different type (e.g., each particular model of forceps can be considered a different type). Alternatively, multiple end effector models can be grouped into one or more types, e.g., multiple models of forceps can be grouped into a single type despite the models having some physical differences. In some implementations, end effector types can be defined more broadly and a single type can include end effectors having similar operation. For example, grasping end effectors having jaws can be defined as an end effector type.

In some implementations, the selected force profile can be a set of force profiles, where one of the force profiles of the set is selected for use based on a current mode or other condition of operation of the teleoperated system or controller. For example, one profile in the set can be designated for use during non-controlling mode of the teleoperated system, and a different profile of the set can be designated for use during controlling mode of the teleoperated system. In some implementations in which multiple master controllers are provided for controlling multiple slave device end effectors (e.g., as in master control workstation 102 of FIG. 2), each master controller can be assigned its own force profile (or set of force profiles) based on the end effector it controls.

In block 2202, a non-controlling mode of the control system (e.g., teleoperated system 100) is activated. The non-controlling mode can also be considered a "safe mode" in which the master controller is not enabled to provide control signals to move a controlled device such as slave device 104, even if the master controller is manipulated by the user. Thus, for example, the controlled device is disconnected from the master controller for non-controlling mode, e.g., the controlled device is not being controlled by the master controller. For example, the master controllers 210 and 212 can be manipulated by a user in non-controlling mode but will not cause any controlled motion of the components of the manipulator slave device 104.

In block 2204, information is received describing a current position of one or more end effectors that can be controlled by the control system. In some implementations, this information can be received by a master controller system (e.g., master control workstation) from the slave device. The information can be derived from sensor information sensed by position sensors of the slave device and relayed to the master controller.

In some examples, the end effector can include one or more instruments, such as the surgical instrument 900 shown in FIG. 9 which is coupled to one or more arms of a slave arm device. For example, the slave arm joints and position can be controlled by the master controller. In addition, one or more components or portions of the instruments can be controlled by the master controller. For example, the jaws or pincher elements of forceps, scissors, graspers, dissectors, clamps, sealers, shears, staplers, clip appliers, needle drivers, and other instruments can be controlled by the master controller as described above with respect to FIG. 9. The information received in block 2204 can describe, for example, the positions of such jaws in their degrees of freedom (e.g., as angular information), and/or can describe the positions of the jaws relative to each other. In some implementations, the information can describe the current position of other types end effector (e.g., one or more components or portions of an instrument), e.g., such as portions of a retractor, cautery hook, spatula, or other component in a rotary degree of freedom of the end effector, a position in a linear degree of freedom, etc.

In block 2206, one or more of the grip members of the master controller are matched to the position of the end effector (or the grip members are otherwise positioned based on the end effector). For example, a control circuit coupled to the master controller can control one or more actuators to move the grip members to a position that corresponds to the position of one or more components of the end effector. In some implementations, the grip members can be moved to positions in their degrees of freedom that correspond to the current positions of associated components of the end effector in their degree of freedom. For example, each of two jaws of a forceps or similar surgical instrument can be associated with one of the grip members, and a grip member can be positioned within its degree of freedom to a position that is proportional to a position that the associated jaw is positioned within its degree of freedom. In one example, a jaw may have a position that is spaced away from one limit of the movement range by an angular amount that is 20% of the entire angular movement range of the jaw, and the associated grip member can be similarly positioned at a position that is 20% of its movement range away from a corresponding limit of its movement range. In another example, a clip applier instrument may be spaced so that the jaws of the clip applier are open and holding a clip, and the associated grip members can be similarly positioned to an open position in the degrees of freedom of the grip members.

In another example of positioning one or more of the grip members based on the end effector, one or more of the grip members of the master controller can be constrained or held to a single position if the end effector has a single moveable components or no moveable components. For example, each inactive grip member can be moved to a closed position of the grip member and maintained at that closed position while the associated end effector is being controlled. In some implementations, one grip member can be operated to control a component of the end effector such that it can be moved within its rotary degree of freedom within a designated movement range, receive forces from the actuator for a force profile, etc., while the other grip member is constrained, e.g., held to a closed position. For example, some end effectors such as a stapler instrument may have components that can be controlled with one moveable grip member. In some implementations, the positioning of the grip members in non-controlling mode can be determined based on a force profile selected in block 2201.

The alignment of position of the end effector and the controller grip members can allow the grip members to be controlled more accurately when a user first contacts the grip members. For example, if an instrument's jaws are in a fully open position but the grip members are in a half-closed position, then the full movement range of the grip members is not available. The grip members can therefore be fully opened to match the jaws of the end effector.

In block 2208, it is determined whether a controlling mode (e.g., "following mode") has been entered or activated by the control system. The controlling mode allows the master controller to control the movements of the slave device. For example, motion of grip members of the master controller can control corresponding motion of jaws of a surgical instrument of the slave device, and/or motion of the master controller in other degrees of freedom can control corresponding motions of the surgical instrument in space.

The activation of controlling mode can be initiated based on any of a variety of conditions. For example, some implementations can initiate the controlling mode in response to detecting the presence of a user at or near the master controller. For example, presence sensor 214 on the master control workstation 102, as described with respect to FIG. 2, can sense whether the head of a user has been detected in an operating position for the master controllers 210 and 212, such as in a viewing recess 211 of master control workstation 102. In some implementations, other sensors can be used to sense user presence. Some implementations can detect whether the user has grasped or otherwise contacted the master controller grip members, e.g., via contact sensors, optical sensors, motion sensors, sensing a change in an output force or vibration applied on the master controller, etc.

If controlling mode has not been entered, then the method returns to block 2206 to continue to match the position of the grip members to the end effector position. If controlling mode has been entered as determined in block 2208, then the method continues to block 2210, in which forces are applied to the grip members of the master controller during operation of the master controller to control the slave device. The forces can be output in the degrees of freedom of the grip members from one or more actuators as described in various implementations herein.

For example, the forces applied to the grip members can be based on one or more force profiles that indicate the force applied for each position of the grip members. For example, a force profiles selected in block 2201 can be used to provide particular forces for a particular type of end effector being controlled on the slave device, as described above.

In some implementations, the forces applied to the grip members can be based on one or more of a variety of states or conditions during the system operation. In some examples, if a controlled end effector encounters a physical object or surface, sensors of the slave device can relay this condition to the master control system, which then controls forces on the grip members to simulate or alert the user of the physical object or surface. For example, if jaws of the end effector pick or hold an object, forces can be output on the grip members at positions corresponding to the size of the held object in the movement range of the instrument jaws, making the grip members harder to close past corresponding positions. In another example, a vibration can be output on the grip members for a particular amount of time and with sufficiently high frequency to simulate the feel of a hard surface at particular positions of the grip members. Such a vibration can impart a sensation of initially impacting a hard surface.

The forces output on the grip members can be coordinated with conditions occurring within a simulation, e.g., a virtual environment created and responding to input provided by the master controller. For example, a simulation of a medical procedure (or other procedure) may allow the master controller to provide control signals to control a physical end effector within a virtual environment, e.g., a virtual operating site or virtual patient. The virtual environment can be displayed to the user on one or more display screens or other display devices, for example, which may also show the physical slave device in that environment (e.g., based on a camera capturing images of the physical slave device). If the physical end effector is determined by the simulation to interact with a virtual obstruction (e.g., a portion of a virtual patient), then forces can be controlled by the master control system to be output on the grip members to simulate interaction with a real environment. For example, a virtual object held by the physical instrument can provide forces on the grip members similarly as a physical object would, as described above. In another example, a simulation of a procedure may allow the master controller to provide control signals to control a virtual slave device within a virtual environment, e.g., a virtual slave device having a virtual end effector that interacts with a virtual operating site or virtual patient. The virtual slave device and environment can be displayed to the user on one or more display screens or other display devices, for example. Forces can be output on the grip members similarly as described above based on interaction of the virtual end effector with virtual objects or surfaces.

Some implementations can indicate to the user via forces output on the grip members of the master controller that the control system has activated a different mode of operation, e.g., the forces can indicate a change in the operating mode. Modes of operation can include the controlling mode and non-controlling mode described herein. In some implementations, additional modes of operation can be provided for a teleoperated system or other control system, and these modes can be indicated by different characteristics of force sensations such as vibrations, bumps (single force pulses), springs (increasing force in a direction of movement), etc. For example, a particular mode can provide control of a camera of the slave device 104 to the master controller instead of control of an end effector, or provide control over other slave device functions or master controller functions.

Various other conditions can cause force output on the grip members (and in other degrees of freedom of the master controller), e.g., alert forces to alert the user of a particular event or condition, forces to cause the user to provide a particular control signal (e.g., a resistance, when overcome, causes a selection of a user interface element or option in a displayed user interface), etc.

In block 2212, it is checked whether the control system exits the controlling mode. For example, controlling mode can be exited in response to the user physically leaving a position to use the master controller (e.g., the user's head or hand no longer sensed in proximity to the controller or controller workstation). In other examples, controlling mode can be exited in response to the procedure being completed, user input (e.g., the user selecting an input device or displayed element in a user interface, voice command, etc.), a condition in the procedure (e.g., an unsafe movement or position of the slave device occurs), etc.

If the control system has not exited the controlling mode, the method returns to block 2210 to continue outputting forces during the operation of the teleoperated system. If the control system has exited the controlling mode, the method returns to block 2202 to activate non-controlling mode.

Some implementations of method 2200 can output forces on the master controller, such as on the grip members of the controller, in non-controlling mode. For example, the master controller may be able to be used in a graphical interface control mode that is a non-controlling mode, where the master controller movement in one or more degrees of freedom can interface with elements of a user interface displayed on a display. In some implementations, forces can be output on the grip members to assist a user in interacting with displayed interface elements. For example, a pinching motion of the grip members can be used to control a zoom level of a view displayed by a display screen, and forces can be output on the grip members to indicate particular zoom levels (e.g., a force "bump" output at each different zoom level). Forces can also be used to indicate a limit to adjustment of a graphical element or parameter. For example, a ramping force similar to force profile 1040 of FIG. 10 can be output at or near a position in the grip members' degrees of freedom that correspond to a maximum parameter value in a graphical interface that can be set by controlling the grip members (e.g., a maximum or minimum zoom level, maximum scroll position of a menu, etc.).

In various implementations, forces output on the grip members can be disabled during a procedure, e.g., for safety reasons, to allow a particular form of control to the user, or for other reasons. All forces can be disabled to the grip members, and/or particular forces can be disabled, such as forces based on designated interactions of the slave device in the procedure (e.g., forces from objects held by controlled instruments, etc.).

The blocks described in the methods disclosed herein can be performed in a different order than shown and/or simultaneously (partially or completely) with other blocks, where appropriate. Some blocks can be performed for one portion of data and later performed again, e.g., for another portion of data. Not all of the described blocks need be performed in various implementations. In some implementations, blocks can be performed multiple times, in a different order, and/or at different times in the methods.

Figure 23:
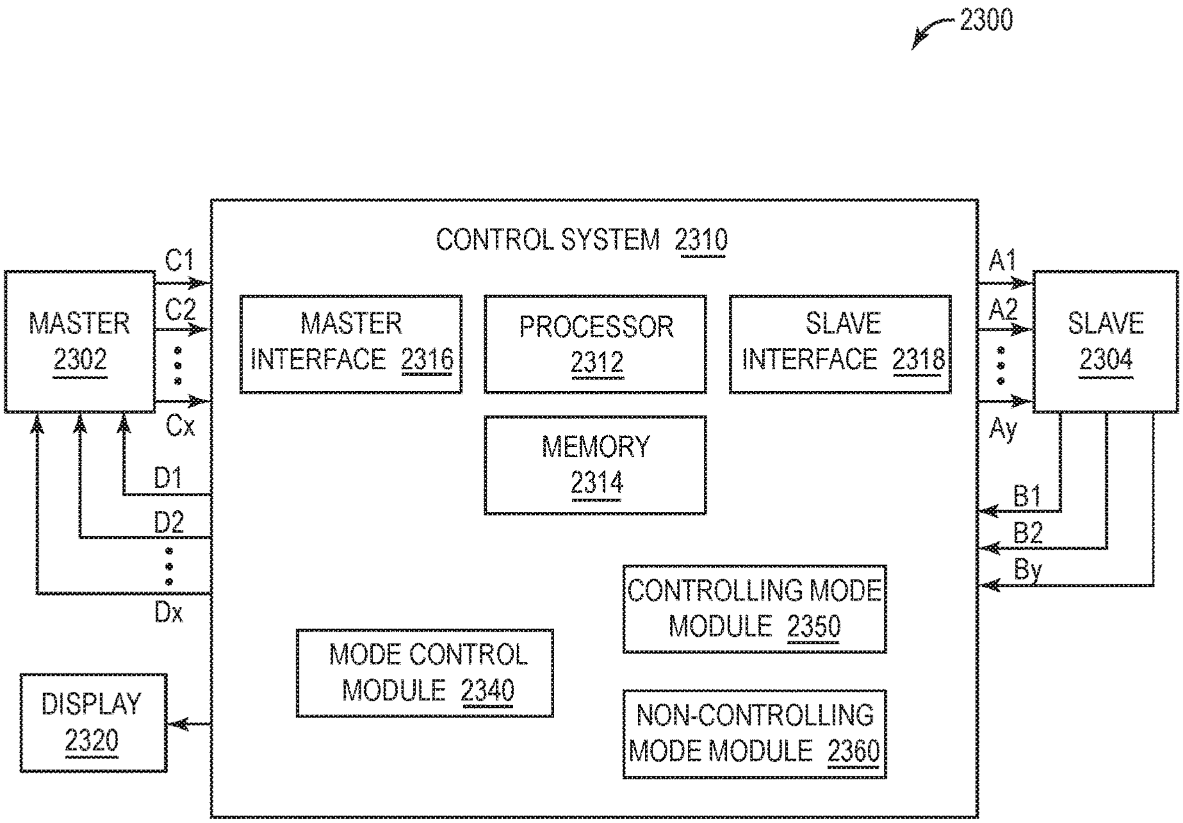
FIG. 23 is a block diagram of an example master-slave system which can be used for one or more implementations described herein.

FIG. 23 is a block diagram of an example master-slave system 2300 which can be used with one or more features described herein. System 2300 includes a master device 2302 that a user may manipulate in order to control a slave device 2304 in communication with the master device 2302. In some implementations, master device 2302 can be, or can be included in, master control workstation 102 of FIG. 1. More generally, master device 2302 can be any type of device providing a master controller that can be physically manipulated by a user. Master device 2302 generates control signals C1 to Cx indicating positions, states, and/or changes of one or more master controllers in their degrees of freedom. The master device 2302 can also generate control signals (not shown) indicating selection of physical buttons and other manipulations by the user.

A control system 2310 can be included in the master device 2302, in the slave device 2304, or in a separate device, e.g., an intermediary device between master device 2302 and slave device 2304. In some implementations, the control system 2310 can be distributed among multiple of these devices. Control system 2310 receives control signals C1 to Cx and generates actuation signals A1 to Ay, which are sent to slave device 2304. Control system 2310 can also receive sensor signals B1 to By from the slave device 2304 that indicate positions, states, and/or changes of various slave components (e.g., manipulator arm elements). Control system 2310 can include general components such as a processor 2312, memory 2314, and interface hardware 2316 and 2318 for communication with master device 2302 and slave device 2304, respectively. Processor 2312 can execute program code and control basic operations of the system 2300, and can include one or more processors of various types, including microprocessors, application specific integrated circuits (ASICs), and other electronic circuits. Memory 2314 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control system 2310, e.g., display(s) 2320 such as the viewer 213 of the master control workstation 102 and/or display 124 of FIG. 2.

In this example, control system 2310 includes a mode control module 2340, a controlling mode module 2350, and a non-controlling mode module 2360. Other implementations can use other modules, e.g., a force output control module, sensor input signal module, etc. As used herein, the term "module" can refer to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware. In some implementations, the modules 2340, 2350, and 2360 can be implemented using the processor 2312 and memory 2314, e.g., program instructions stored in memory 2314 and/or other memory or storage devices connected to control system 2310.

Mode control module 2340 can detect when a user initiates a controlling mode and a non-controlling mode of the system, e.g., by user selection of controls, sensing a presence of a user at a master control workstation or master controller, sensing required manipulation of a master controller, etc. The mode control module can set the controlling mode or a non-controlling mode of the control system 2310 based on one or more control signals C1 to Cx. For example, mode control module 2340 may activate controlling mode operation if user detection module 2330 detects that a user is in proper position for use of the master control and that signals (e.g., one or more signals C1 to Cx) indicate the user has contacted the master controller. The mode control module 2340 may disable controlling mode if no user touch is detected on the master controller and/or if a user is not in proper position for use of the master controller. For example, the mode control module 2340 can inform control system 2310 or send information directly to controlling mode module 2350 to prevent the controlling mode module 2350 from generating actuation signals A1 to An that move slave device 2304.

In some implementations, controlling mode module 2350 may be used to control a controlling mode of control system 2310. Controlling mode module 2350 can receive control signals C1 to Cx and can generate actuation signals A1 to Ay that control actuators of the slave device 2304 and cause it to follow the movement of master device 2302, e.g., so that the movements of slave device 2304 correspond to a mapping of the movements of master device 2302. Controlling mode module 2350 can be implemented using conventional techniques.

Controlling mode module 2350 can also be used to control forces on the master controller of the master device 2302 as described herein, e.g., forces output on one or more components of the master controller, e.g., grip members, using one or more control signals D1 to Dx output to actuator(s) used to apply forces to the components. For example, one or more of control signals D1 to Dx can be output to one or more actuators configured to output forces to the grip members of the master controller as described herein, and output to one or more other actuators of the master controller, e.g., actuators configured to output forces in a rotary degree of freedom of the controller, actuators configured to output forces on arm links coupled to the master controller, etc. In some examples, control signals D1 to Dx can be used to provide force feedback, gravity compensation, etc.

In some implementations, a non-controlling mode module 2360 may be used to control a non-controlling mode of system 2300. In the non-controlling mode, movement in one or more degrees of freedom of master device 2302, or other manipulations of master device 2302, has no effect on the movement of one or more components of slave 2304. In some examples, non-controlling mode may be used when a portion of slave 2304, e.g., a slave arm assembly, is not being controlled by master 2302, but rather is floating in space and may be manually moved. For non-controlling mode, non-controlling mode module 2360 may allow actuator systems in the slave 2304 to be freewheeling or may generate actuation signals A1 to An, for example, to allow motors in an arm to support the expected weight of the arm against gravity, where brakes in the arm are not engaged and permit manual movement of the arm. For example, in a medical procedure, non-controlling mode may allow a surgical side assistant to easily manipulate and reposition an arm or other slave component relative to a patient or directly make some other clinically appropriate adjustment of the arm or slave component.

In some implementations, non-controlling mode can include one or more other operating modes of the control system 2310. For example, a non-controlling mode can be a selection mode in which movement of the master controller in one or more of its degrees of freedom and/or selection of controls of the master controller (e.g., buttons 440 of FIG. 4) can control selection of displayed options, e.g., in a graphical user interface displayed by display 2320 and/or other display device. A viewing mode can allow movement of the master controller to control a display provided from cameras, or movement of cameras, that may not be included in the slave device 2304. Control signals C1 to Cx can be used by the non-controlling mode module 2360 to control such elements (e.g., cursor, views, etc.) and control signals D1 to Dx can be determined by the non-controlling mode module to cause output of forces on the master controller during such non-controlling modes, e.g., to indicate to the user interactions or events occurring during such modes.

Some implementations described herein, e.g., method 600, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the spirit and scope of the present disclosure. Accordingly, many modifications may be made by one of ordinary skill in the art without departing from the spirit and scope of the appended claims.

What is claimed is:

1. A controller comprising:

a central member having a central axis;

a grip member coupled to the central member, wherein the grip member is:

rotatable in a first degree of freedom about the central axis;

moveable in a second degree of freedom relative to the central member, wherein the second degree of freedom is different than the first degree of freedom;

a shaft coupled to the grip member; and an actuator coupled to the shaft and operative to output actuator forces to the shaft, wherein the actuator forces are output based on control signals received by the actuator and the actuator forces are transmitted via the shaft to the grip member in the second degree of freedom.

2. The controller of claim 1, wherein the shaft extends parallel to the central axis.

3. The controller of claim 1, wherein movement in the second degree of freedom includes movement of at least a portion of the grip member toward or away from the central member.

4. The controller of claim 1, wherein the first degree of freedom includes rotation of the grip member and the central member about a longitudinal axis of the shaft.

5. The controller of claim 1, wherein the actuator is a first actuator, and further comprising a second actuator coupled to the central member and operative to output second actuator forces to cause rotation of the grip member and the central member in the first degree of freedom, wherein the rotation in the first degree of freedom is decoupled in rotation from the first actuator.

6. The controller of claim 1, wherein the shaft is coupled to the grip member via at least one rotary coupling such that the grip member is rotatable relative to the shaft.

7. The controller of claim 1, wherein the actuator is a motor or a voice coil that outputs the actuator forces.

8. The controller of claim 1, wherein the actuator is a linear actuator and the actuator forces are linear forces output to the shaft along a longitudinal axis of the shaft.

9. The controller of claim 1, wherein the actuator is a rotary actuator and the actuator forces are rotational forces that are converted to linear forces applied along a longitudinal axis of the shaft.

10. The controller of claim 9, further comprising a transmission coupled between the rotary actuator and the shaft, wherein the transmission includes one of:

a ballscrew mechanism; or a crank and a linkage, the crank coupled to the actuator, the linkage including two rotatably linked members and coupled between the crank and the shaft.

11. The controller of claim 9, further comprising a transmission coupled between the rotary actuator and the shaft, wherein the transmission includes a capstan drum coupled to the actuator and a carriage coupled to the shaft, wherein the capstan drum is coupled to the carriage by a cable.

12. The controller of claim 1, wherein the grip member is a first grip member, and further comprising:

a second grip member coupled to the central member and to the shaft, wherein the second grip member is rotatable in a third degree of freedom relative to the central member, wherein the third degree of freedom is different than the first degree of freedom and different than the second degree of freedom.

13. The controller of claim 12, wherein the actuator forces are transmitted via the shaft to the first grip member in the second degree of freedom and to the second grip member in the third degree of freedom.

14. The controller of claim 12, wherein the first and second grip members are coupled to the shaft by one or more link members, and wherein the one or more link members are configured to cause the first and second grip members to simultaneously move in the second and third degrees of freedom, respectively, in directions toward each other or away from each other.

15. The controller of claim 14, wherein the one or more link members include:

a first link member having a first rotary coupling between a first end of the first link member and the shaft and having a second rotary coupling between a second end of the first link member and the first grip member, and a second link member having a first rotary coupling between a first end of the second link member and the shaft and having a second rotary coupling between a second end of the second link member and the second grip member.

16. The controller of claim 1, wherein the actuator is a first actuator, the shaft is a first shaft, the actuator forces are first actuator forces, the controller further comprising:

a second grip member coupled to the central member, wherein the second grip member is moveable in a third degree of freedom relative to the central member, wherein the third degree of freedom is different than the first degree of freedom and the second degree of freedom;

a second shaft coupled to the second grip member; and a second actuator coupled to the second shaft and operative to output second actuator forces to the second shaft, wherein the second actuator forces are transmitted via the second shaft to the second grip member in the third degree of freedom.

17. A method comprising:

sensing, with a first sensor, one or more positions of a grip member of a controller in a first rotary degree of freedom of the grip member about a central axis, the grip member rotatably coupled to a central member and to a shaft of the controller, the central member having the central axis, wherein the one or more positions are used to control first movement of an end effector of a device in communication with the controller;

sensing, with a second sensor, one or more positions of the grip member in a second rotary degree of freedom of the grip member relative to the central member; and applying forces to the grip member by controlling an actuator coupled to the shaft to output the actuator forces to the shaft, wherein the actuator forces are transmitted via the shaft to the grip member in the second rotary degree of freedom by sending control signals to the actuator.

18. The method of claim 17, wherein the shaft extends parallel to the central axis, and wherein the one or more positions of the grip member in the second rotary degree of freedom are included in movement of at least a portion of the grip member toward or away from the central member.

19. The method of claim 17, wherein the grip member is a first grip member, wherein the controller further includes a second grip member rotatably coupled to the central member and to the shaft, wherein the second grip member is rotatable in a third rotary degree of freedom different than the first rotary degree of freedom and the second rotary degree of freedom.

20. The method of claim 17, wherein the one or more positions are used to control movement of an end effector of a slave device in communication with the controller, wherein applying the forces causes movement of the grip member to at least one position in the second rotary degree of freedom to match a position of the end effector.

* * * * *